United States Patent
Rogelj et al.

(10) Patent No.: US 12,029,728 B2
(45) Date of Patent: Jul. 9, 2024

(54) SMALL MOLECULES WITH ANTI-PROTOZOAN ACTIVITY

(71) Applicant: New Mexico Tech University Research Park Corporation, Socorro, NM (US)

(72) Inventors: Snezna Rogelj, Socorro, NM (US); Danielle Nicole Turner, Socorro, NM (US); Ivy Hurwitz, Socorro, NM (US); Alexander Aksenov, Socorro, NM (US)

(73) Assignee: New Mexico Tech University Research Park Corporation, Socorro, NM (US)

( * ) Notice: Subject to any disclaimer, the term of this patent is extended or adjusted under 35 U.S.C. 154(b) by 0 days.

(21) Appl. No.: 17/286,599

(22) PCT Filed: Oct. 29, 2019

(86) PCT No.: PCT/US2019/058572
§ 371 (c)(1),
(2) Date: Apr. 19, 2021

(87) PCT Pub. No.: WO2020/092374
PCT Pub. Date: May 7, 2020

(65) Prior Publication Data
US 2021/0386707 A1    Dec. 16, 2021

Related U.S. Application Data

(60) Provisional application No. 62/752,548, filed on Oct. 30, 2018.

(51) Int. Cl.
*A61K 31/405* (2006.01)
*A61K 31/404* (2006.01)
*A61P 33/02* (2006.01)

(52) U.S. Cl.
CPC .......... *A61K 31/405* (2013.01); *A61K 31/404* (2013.01); *A61P 33/02* (2018.01)

(58) Field of Classification Search
CPC ...... A61K 31/405; A61K 31/404; A61P 33/02
See application file for complete search history.

(56) References Cited

U.S. PATENT DOCUMENTS

| 6,630,482 B1 | 10/2003 | Becq et al. |
| 9,206,124 B2 | 12/2015 | Akensov et al. |
| 2010/0183658 A1* | 7/2010 | Wucherpfennig ...... A61P 37/06 514/363 |
| 2018/0110861 A1* | 4/2018 | Panda ................... C07C 229/08 |

FOREIGN PATENT DOCUMENTS

| EP | 1783114 A1 | 5/2007 |
| WO | WO-2011156632 A2 | 12/2011 |
| WO | WO-2019088910 A1 | 5/2019 |

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995 (Year: 1995).*
Aksenov et al., Activity of 2-Aryl-2-(3-indolyl)acetohydroxamates Against Drug-Resistant Cancer Cells, J Med Chem, 2015, vol. 58 (5), p. 2206-2220.
PCT/US2019/058572 International Preliminary Report on Patentability dated May 14, 2021.
PCT/US2019/058572 International Search Report and Written Opinion dated Feb. 19, 2020.
PubChem CID 11958074, create date: Apr. 12, 2006.
PubChem CID 12644416, create date: Aug. 2, 2007.
PubChem CID 3920633, create date: Sep. 12, 2005.

* cited by examiner

*Primary Examiner* — Marcos L Sznaidman
(74) *Attorney, Agent, or Firm* — Wilson Sonsini Goodrich & Rosati

(57) ABSTRACT

The present disclosure describes a method of treating an infection, including a parasitic infection, using compounds of the invention. The compounds of the invention can selectively eradicate intracellular mammalian and human parasites.

11 Claims, 43 Drawing Sheets

A.

B.

A.

B.

A.

B.

Hoechst staining, with mask applied

1% DMSO

40 µM Compound 2

A.

B.

SMALL MOLECULES WITH ANTI-PROTOZOAN ACTIVITY

CROSS REFERENCE

This application is a 35 U.S.C. §371 U.S. National Stage Entry of International Application No. PCT/US/2019/058572, filed Oct. 29, 2019, which claims the benefit of U.S. Provisional Application No. 62/752,548, filed Oct. 30, 2018, each of which is incorporated herein by reference in its entirety.

GOVERNMENT RIGHTS

This invention was made with the support of the United States government under Grant number P20GM103451 by the National Institute of General Medical Sciences. The government has certain rights in the invention.

BACKGROUND

Protozoa are microscopic, one-celled organisms that are free-living or parasitic in nature. Protozoa can multiply in humans. Multiplication contributes to protozoa's survival and permits serious infections to develop from just a single organism. Parasitic infections exist in over 90 countries worldwide and have limited treatment options.

INCORPORATION BY REFERENCE

Each patent, publication, and non-patent literature cited in the application is hereby incorporated by reference in its entirety as if each was incorporated by reference individually.

SUMMARY

In one aspect, the invention describes a method of treating an infection, the method comprising: administering to a subject in need thereof a therapeutically-effective amount of a compound of the formula:

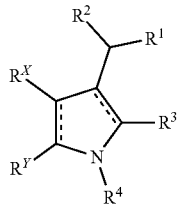

wherein:
each ≡≡≡ is independently a single bond or a double bond,
$R^1$ is cyano, an imine group, an acyl group, a carboxylic acid group, a carboxaldehyde group, an ester group, an amide group, a hydrazide group, a hydroxamic acid group, a hydroxamic acid ester group, a thioester group, or a thioacid group, any of which is substituted or unsubstituted;
each $R^2$ and $R^3$ is independently cyano, an imine group, an acyl group, alkyl, alkenyl, alkynyl, a carboxylic acid group, a carboxaldehyde group, an ester group, an amide group, a hydrazide group, a hydroxamic acid group, a hydroxamic acid ester group, a thioester group, a thioacid group, aryl, arylalkyl, heterocyclyl, cycloalkyl, cycloalkenyl, heterocyclyl, or heteroaryl, any of which is substituted or unsubstituted;
$R^4$ is an imine group, an acyl group, an acyloxy group, alkyl, alkenyl, alkynyl, an alkoxy group, an ether group, a carboxylic acid group, a carboxaldehyde group, an ester group, an amide group, a hydrazide group, a hydroxamic acid group, a hydroxamic acid ester group, a thioether group, a thioester group, a thioacid group, aryl, aryloxy, arylalkyl, arylalkoxy, heterocyclyl, cycloalkyl, cycloalkenyl, heterocyclyl, or heteroaryl, any of which is substituted or unsubstituted, or hydrogen; and
$R^X$ and $R^Y$ together with the atoms to which $R^X$ and $R^Y$ are bound form a ring that is substituted or unsubstituted, or a pharmaceutically-acceptable salt thereof.

BRIEF DESCRIPTION OF THE DRAWINGS

FIG. 1 PANEL B shows an image of HeLa cells 6 hours after treatment with Compound 2 and DAPI stain.
FIG. 1 PANEL C shows an image of HeLa cells 6 hours after treatment with MitoTracker Red and DAPI stain.
FIG. 1 PANEL D shows an overlay image of HeLa cells 6 hours after treatment with Compound 2.
FIG. 1 PANEL E shows an intensity quantification plot of the images of HeLa cells 6 hours after treatment with Compound 2.
FIG. 1 PANEL F shows a co-localization plot of HeLa cells 6 hours after treatment with Compound 2 and MitoTracker Red stain.
FIG. 1 PANEL G shows a phase contrast microscopy image of HeLa cells 48 hours after treatment with Compound 2.
FIG. 1 PANEL H shows an image of HeLa cells 48 hours after treatment with Compound 2 and DAPI stain.
FIG. 1 PANEL I shows an image of HeLa cells 48 hours after treatment with MitoTracker Red and DAPI stain.
FIG. 1 PANEL J shows an overlay image of HeLa cells 48 hours after treatment with Compound 2.
FIG. 1 PANEL K shows an intensity quantification plot of the images of HeLa cells 48 hours after treatment with Compound 2.
FIG. 1 PANEL L shows a co-localization plot of HeLa cells 48 hours after treatment with Compound 2 and MitoTracker Red stain.
FIG. 2 PANEL B shows a graph of Compound 2 dose-dependent changes in ATP production as measured by RLUs.
FIG. 7 PANEL B and PANEL C show images of *T. cruzi*-infected ARPE cells that did not receive treatment with Compound 2.
FIG. 7 PANEL D shows an image of non-infected ARPE cells treated with 5

μM Compound 2. FIG. 7 PANEL E and PANEL F show images of *T. cruzi*-infected ARPE cells treated with 5 μM Compound 2.

FIG. 8 PANEL B shows an image of uninfected ARPE cells treated with 1 μM Compound 2. FIG. 8 PANEL C shows an image of *T. cruzi*-infected ARPE cells that did not receive treatment with Compound 2. FIG. 8 PANEL D shows an image of *T. cruzi*-infected ARPE cells treated with 1 μM Compound 2.

FIG. 9 PANEL B shows an image of *T. cruzi*-infected ARPE cells that were treated with 1 μM Compound 2.

FIG. 10 PANEL B shows images of uninfected ARPE cells treated with 1 μM Compound 2. FIG. 10 PANEL C shows images of *T. cruzi*-infected ARPE cells that were not treated with Compound 2. FIG. 10 PANEL D shows images of *T. cruzi*-infected ARPE cells treated with 1 μM Compound 2.

FIG. 12 PANEL B shows images of uninfected ARPE cells treated with a single treatment of 1 μM Compound 2. FIG. 12 PANEL C shows images of uninfected ARPE cells treated three times with 1 μM Compound 2. FIG. 12 PANEL D shows images of *T. cruzi*-infected ARPE cells that were not treated with Compound 2. FIG. 12 PANEL E shows images of *T. cruzi*-infected ARPE cells that received a single treatment of 1 μM Compound 2. FIG. 12 PANEL F shows images of *T. cruzi*-infected ARPE cells after three treatments with 1 μM Compound 2.

FIG. 13 ROW B shows images of *T. cruzi*-infected ARPE cells that were used as a control. FIG. 13 ROW C shows images of uninfected ARPE cells treated with 2 μM Compound 2. FIG. 13 ROW D shows images of *T. cruzi*-infected ARPE cells treated with 2 μM Compound 2.

FIG. 14 ROW B shows images of uninfected cells treated with 5 μM Compound 2. FIG. 14 ROW C shows images of *T. cruzi*-infected cells that were not treated with Compound 2. FIG. 14 ROW D shows images of *T. cruzi*-infected cells that were treated with 5 μM Compound 2.

FIG. 16 PANEL B shows an image of infected cells treated with 10 μM Compound 2. FIG. 16 PANEL C shows an image of infected cells treated with 5 μM of Compound 2.

FIG. 17 ROW B shows images of *T. cruzi*-infected ARPE cells that received treatment with 5 μM Compound 2. FIG. 17 ROW C shows images of *T. cruzi*-infected ARPE cells that received treatment with 10 μM Compound 2.

FIG. 18 PANEL B shows images of ARPE cells upon the completion of 4 treatments with 2 μM Compound 2 over a period of 4 days, with 5 additional days of incubation without further treatment.

FIG. 21 ROW B shows images of *T. cruzi*-infected ARPE cells that did not receive treatment with Compound 2. FIG. 21 ROW C shows images of uninfected ARPE cells that received treatment with 2 μM Compound 2. FIG. 21 ROW D shows images of *T. cruzi*-infected ARPE cells that were treated with 2 μM Compound 2.

FIG. 22 PANEL B shows an image of uninfected ARPE cells treated with 2 μM Compound 2. FIG. 22 PANEL C shows an image of uninfected ARPE cells treated with 2 μM Compound 7. FIG. 22 PANEL D shows an image of *T. cruzi*-infected ARPE cells that did not receive treatment with Compound 2 or Compound 7. FIG. 22 PANEL E shows an image of *T. cruzi*-infected ARPE cells treated with 2 μM Compound 2. FIG. 22 PANEL F shows an image of *T. cruzi*-infected ARPE cells treated with 2 μM Compound 7.

FIG. 23 ROW B shows images of uninfected ARPE cells that were not treated with Compound 2 or Compound 7. FIG. 23 ROW C shows images of uninfected ARPE cells that were treated with 2 μM Compound 2. FIG. 23 ROW D shows images of uninfected ARPE cells that were treated with 2 μM Compound 7. FIG. 23 ROW E shows images of *T. cruzi*-infected ARPE cells that were treated with 2 μM Compound 2. FIG. 23 ROW F shows images of *T. cruzi*-infected ARPE cells that were treated with 2 μM Compound 7.

FIG. 24 ROW B shows images of *T. cruzi*-infected ARPE cells that were treated with 5 μM Compound 7. FIG. 24 ROW C shows images of *T. cruzi*-infected ARPE cells that were treated with 2.5 μM Compound 7. FIG. 24 ROW D shows images of *T. cruzi*-infected ARPE cells that were treated with 1 μM Compound 7.

FIG. 25 ROW B shows images of *T. cruzi*-infected ARPE cells that were treated with 10 μM Compound 1. FIG. 25 ROW C shows images of *T. cruzi*-infected ARPE cells that were untreated and used as controls. FIG. 25 ROW D shows images of *T. cruzi*-infected ARPE cells that were treated with 10 μM Compound 1.

FIG. 26 ROW B shows images of *T. cruzi*-infected VERO cells that were treated with 5 μM Compound 2. FIG. 26 ROW C shows images of *T. cruzi*-infected VERO cells that were treated with 5 μM Compound 7. FIG. 26 ROW D shows images of uninfected VERO cells that were not treated with Compound 2 or Compound 7. FIG. 26 ROW E shows images of uninfected VERO cells that were treated with 5 µM Compound 2. FIG. 26 ROW F shows images of uninfected VERO cells that were treated with 5 µM Compound 7.

FIG. 27 PANEL B shows the effect of nifurtimox on *T. cruzi* amastigotes. FIG. 27 PANEL C shows the effect of nifurtimox on *T. cruzi* trypomastigotes.

FIG. 28 PANEL B shows the effect of benznidazole on *T. cruzi* amastigotes. FIG. 28 PANEL C shows the effect of benznidazole on *T. cruzi* trypomastigotes.

FIG. 29 PANEL B shows *T. cruzi*-infected ARPE cells used as a control. FIG. 29 PANEL C shows uninfected ARPE cells treated with 2 µM benznidazole. FIG. 29 PANEL D shows *T. cruzi*-infected ARPE cells treated with 2 µM benznidazole.

FIG. 30 ROW B shows *T. gondii*-infected ARPE cells treated with 1 µM Compound 2. FIG. 30 ROW C shows *T. gondii*-infected ARPE cells treated with 2 µM Compound 2. FIG. 30 ROW D shows *T. gondii*-infected ARPE cells treated with 5 µM Compound 2.

FIG. 31 PANEL B shows images of uninfected ARPE cells that were treated with 5 µM Compound 2 for 3 days. FIG. 31 PANEL C shows images of *T. gondii*-infected ARPE cells that were treated with DMSO for 3 days. FIG. 31 PANEL D shows images of *T. gondii*-infected ARPE cells that were treated with 5 µM Compound 2 for 3 days.

FIG. 32 ROW B shows images of *T. gondii*-infected ARPE cells that were treated with 5 µM Compound 2 for 5 days.

FIG. 38 PANEL B shows a micrograph image of *L. major*-infected PBMC cells treated with 1% DMSO and treated with Hoechst staining. FIG. 38 PANEL C shows a micrograph image of *L. major*-infected PBMC cells treated with 40 µM Compound 2. FIG. 38 PANEL D shows a micrograph image of *L. major*-infected PBMC cells treated with 40 µM Compound 2 and Hoechst staining.

FIG. 39 PANEL B shows a magnified image of *L. major*-infected PBMC cells treated with 40 µM Compound 2 and Hoechst staining.

FIG. 40. PANEL B shows the outcome of a double treatment.

FIG. 41 PANEL B shows images of uninfected THP-1 cells treated with 2 µM Compound 2. FIG. 41 PANEL C shows images of *T. cruzi*-infected THP-1 cells that were untreated. FIG. 41 PANEL D shows images of *T. cruzi*-infected THP-1 cells that were treated with 2 µM Compound 2.

DETAILED DESCRIPTION OF THE INVENTION

Figure 1:
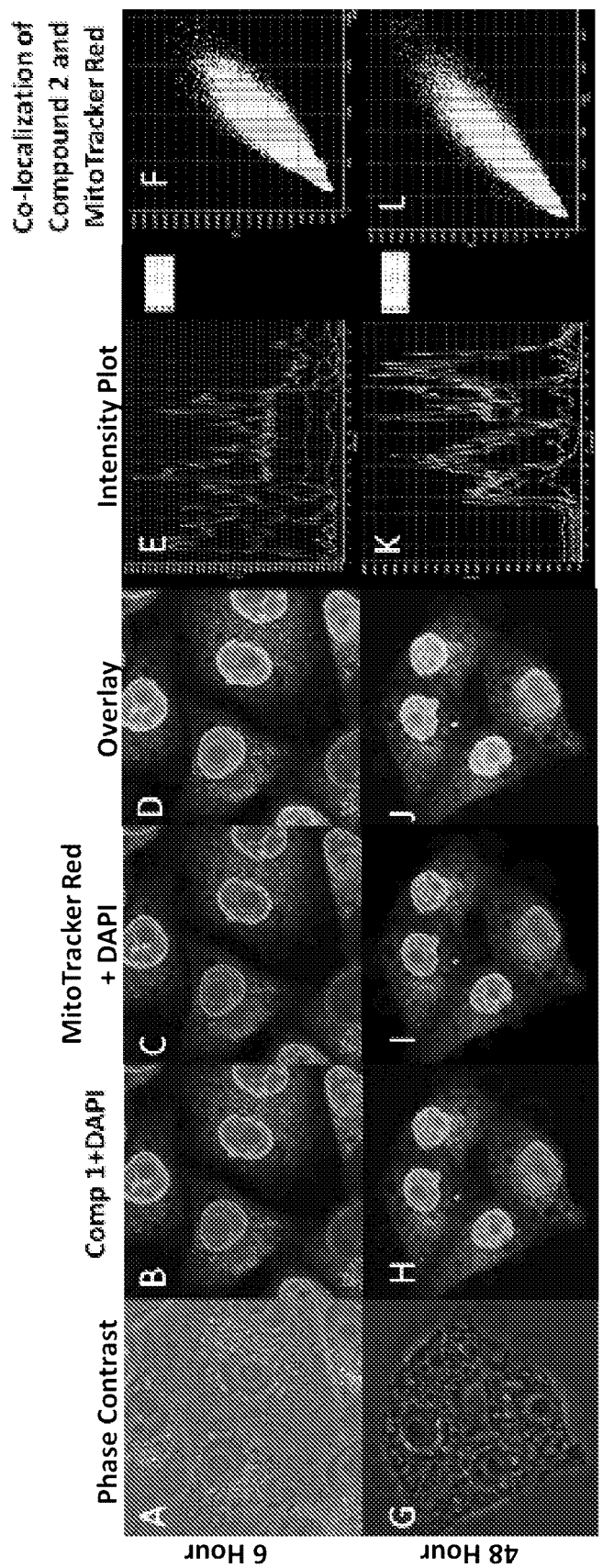
FIG. 1 PANEL A shows a phase contrast microscopy image of HeLa cells 6 hours after treatment with Compound 2.

Parasitic Infections.

A parasite is an organism that lives on or in a host organism and feeds from or at the expense of the host organism. The three main classes of parasites that can cause disease in humans are: protozoa, helminths, and ectoparasites.

Protozoa are microscopic, one-celled organisms that are free-living or parasitic in nature. Protozoa can multiply in humans. Multiplication contributes to their survival and permits serious infections to develop from a single organism. Transmission of protozoa that live in a human's intestines to another human typically occurs through a fecal-oral route (e.g., contaminated food, water, or person-to-person contact). Protozoa that live in the blood or tissue of humans are transmitted to other humans by an arthropod vector (e.g., bite of a mosquito or sand fly).

Protozoa that are infectious to humans can be classified into four groups based on the protozoa's mode of movement: 1) Sarcodina—the ameba (e.g., *Entamoeba*); 2) *Mastigophora*—the flagellates (e.g., *Giardia*, *Leishmania*); 3) *Ciliophora*—the ciliates (e.g., *Balantidium*); and 4) Sporozoa—organisms whose adult stage is not motile (e.g., *Plasmodium*, *Cryptosporidium*).

Trypanosomatida is a group of kinetoplastic excavates distinguished by having only a single flagellum. All members of trypanosomatida are exclusively parasitic and are found primarily in insects. Some trypanosomatids occupy a single host, while many others are heteroxenous and live in more than one host species over their life cycle. The three major human diseases caused by trypanosomatids are African trypanosomiasis, South American trypanosomiasis (Chagas disease), and leishmaniasis.

Different morphological forms appear in the life cycles of trypanosomatids, distinguished mainly by the position, length, and the cell body attachment of the flagellum. The kinetoplast is found closely associated with the basal body at the base of the flagellum. All species of trypanosomatid have a single nucleus. Amastigotes (leishmanial) are a common morphology during an intracellular lifecycle stage in a mammalian host. The promastigote (leptomond) form is a common morphology in an insect host. The flagellum is found anterior of the nucleus, and the flagellum is not attached to the cell body. Epimastigotes (crithidial) are a common form in insect hosts. The flagellum exits the cell interior of the nucleus and is partially connected to the cell body by an undulating membrane. Trypomastigotes (trypanosomal) are characteristic of the genus *Trypanosoma* in the mammalian host bloodstream and infective metacyclic stages in fly vectors. Opisthomastigotes (herpetomonad) are a rarer morphology where the flagellum is posterior of the nucleus, passing through a long groove in the cell.

Chagas disease (CD) is caused by the parasite *Trypanosoma cruzi* (*T. cruzi*), which is transmitted to animals and people by insect vectors that are found mainly in rural areas of Latin America. CD is also called American trypanosomiasis. As many as 8 million people in Mexico, Central America, and South America have CD.

CD has acute and chronic phases. If untreated, infections are lifelong and can be life threatening. Acute CD occurs immediately after infection and can last up to a few weeks or months. During the acute phase, parasites can be found in circulating blood. The acute phase of infection is usually mild or asymptomatic. The host can have a fever or swelling around the site of inoculation (i.e., where the parasite entered the skin or mucous membrane). Rarely, an acute infection can result in severe inflammation of the heart muscle or the brain and lining around the brain. Following the acute phase, most infected people enter a prolonged asymptomatic form of the disease called "chronic indeterminate", during which no parasites are found in the blood.

Many people remain asymptomatic for life and never develop CD-related symptoms. An estimated 20-30% of infected people develop severe and sometimes life-threatening medical problems, including heart rhythm abnormalities that can cause sudden death, a dilated heart that does not pump blood well, or a dilated esophagus or colon that leads to difficulties with eating or passing stool.

Leishmaniasis is caused by protozoan parasites of the genus *Leishmania*, which is transmitted to humans through the bite of infected female Phlebotomous sandflies. Forms of leishmaniasis include cutaneous leishmaniasis, visceral leishmaniasis, and mucosal leishmaniasis. The most common form of leishmaniasis is cutaneous leishmaniasis, which causes skin sores. The sores can start out as papules (bumps) or nodules (lumps) and can form ulcers. The other main form of leishmaniasis is visceral leishmaniasis, caused by *Leishmania donovani*. This form affects internal organs (e.g., spleen, liver, and bone marrow), causes kala-azar ("black fever"), and exhibits a mortality rate of 75%-95%. Affected people usually have a fever, weight loss, enlargement of the spleen and liver, and low blood counts (i.e., anemia, leukopenia, and thrombocytopenia). Mucosal leishmaniasis is less common than cutaneous or visceral leishmaniasis are, and can cause sores in the mucous membranes of the nose, mouth, or throat.

*Leishmania major* (*L. major*) is a species of parasites found in the genus *Leishmania* and is associated with zoonic cutaneous leishmaniasis (also known as Aleppo boil, Baghdad boil, Bay sore, Biskra button, Chiclero ulcer, Dehli boil, Kandahar sore, Lahore sore, Oriental sore, Pian bois, and Uta). *L. major* is an intracellular pathogen that infects the macrophages and dendritic cells of the immune system.

CD and leishmaniasis are collectively called kinetoplastic diseases. Drugs used in treating CD include benznidazole and nifurtimox. However, neither agent reliably and eliminates *T. cruzi* from the body, and benznidazole and nifurtimox are toxic. Pentavalent antimonies and miltefosine are used to treat leishmaniasis. Drug-resistant strains of parasites have arisen, leaving limited options for treatment.

*Toxoplasma gondii* (*T. gondii*) is an obligate intracellular parasitic one-celled eukaryote that causes the infectious disease toxoplasmosis. *T. gondii* is capable of infecting virtually all warm-blooded animals. Mild, flu-like symptoms occasionally occur during the first few weeks following exposure, and infection with *T. gondii* generally produces no readily observable symptoms in healthy human adults. An asymptomatic state of infection is called a latent infection, and is associated with subtle, adverse or pathological behavioral alterations in humans. In infants, HIV/AIDS patients, and others with weakened immunity, infection can cause the serious and occasionally fatal illness, toxoplasmosis.

*Plasmodium falciparum* (*P. falciparum*) is a unicellular protozoan parasite of humans. *P. falciparum* is the deadliest species of *Plasmodium* that causes malaria in humans. The parasite is transmitted through the bite of a female *Anopheles* mosquito, and causes *falciparum* malaria, which is responsible for around 50% of all malaria cases. *P. falciparum* is also associated with the development of blood cancer (Burkitt's lymphoma) and is classified as a Group 2A carcinogen.

Compounds of the Disclosure

The present disclosure describes compounds with antiprotozoan activity. The compounds of the disclosure can inhibit the proliferation of protozoa, including *L. major, T. cruzi*, and *P. falciparum*.

Non-limiting examples of compounds of the disclosure include compounds of any of the following formulae:

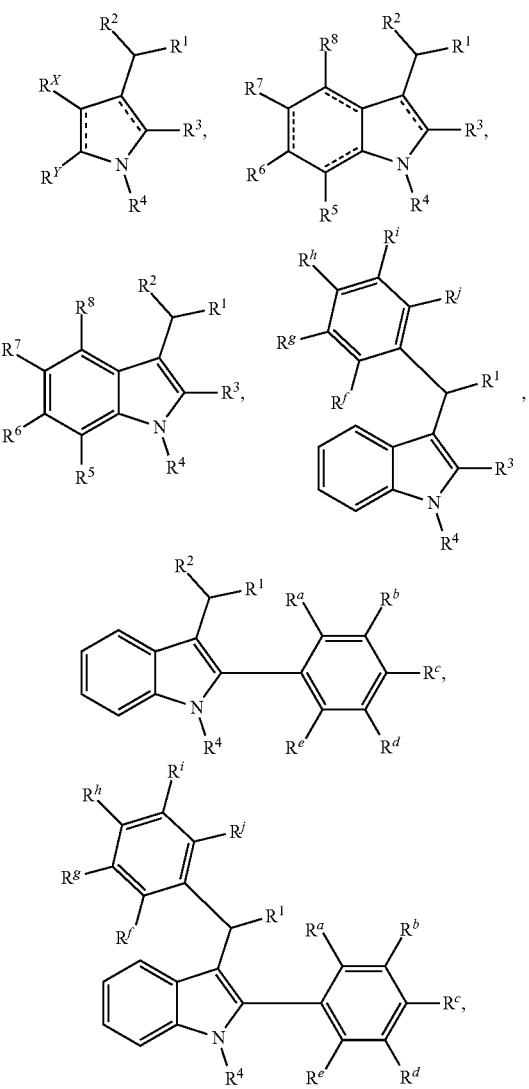

-continued

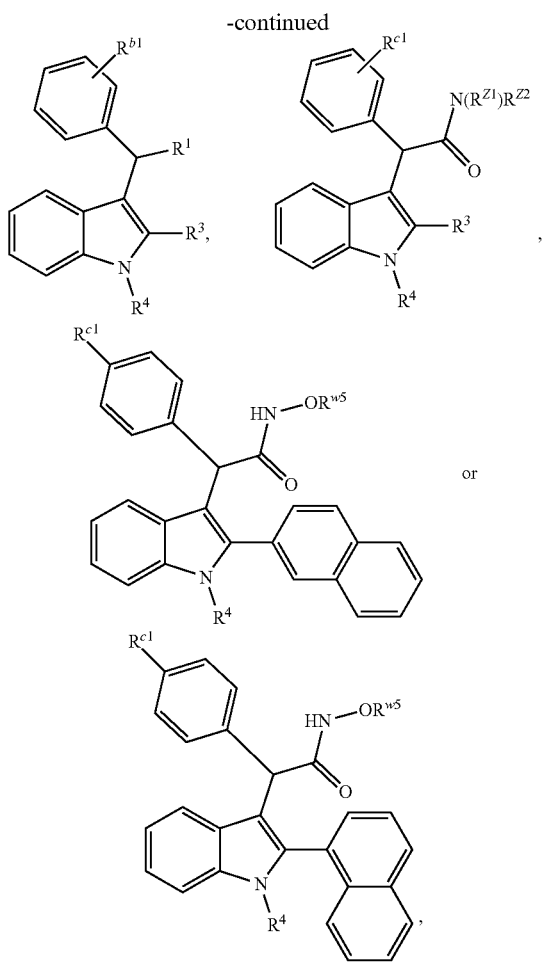

or a pharmaceutically-acceptable salt thereof.

Compounds of the disclosure include compounds of any of the following formulae:

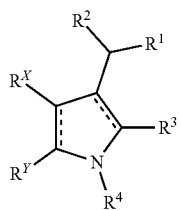

wherein:
  each ==== is independently a single bond or a double bond,
  $R^1$ is cyano, an imine group, an acyl group, an acyloxy group, a carboxylic acid group, a carboxaldehyde group, an ester group, an amide group, a hydrazide group, a hydroxamic acid group, a hydroxamic acid ester group, a thioester group, or a thioacid group, any of which is substituted or unsubstituted;
  each $R^2$ and $R^3$ is independently cyano, an imine group, an acyl group, an acyloxy group, alkyl, alkenyl, alkynyl, an alkoxy group, a carboxylic acid group, a carboxaldehyde group, an ester group, an amide group, a hydrazide group, a hydroxamic acid group, a hydroxamic acid ester group, a thioester group, a thioacid group, aryl, aryloxy, arylalkyl, arylalkoxy, heterocyclyl, cycloalkyl, cycloalkenyl, heterocyclyl, or heteroaryl, any of which is substituted or unsubstituted;
  $R^4$ is an imine group, an acyl group, an acyloxy group, alkyl, alkenyl, alkynyl, an alkoxy group, an ether group, a carboxylic acid group, a carboxaldehyde group, an ester group, an amide group, a hydrazide group, a hydroxamic acid group, a hydroxamic acid ester group, a thioether group, a thioester group, a thioacid group, aryl, aryloxy, arylalkyl, arylalkoxy, heterocyclyl, cycloalkyl, cycloalkenyl, heterocyclyl, or heteroaryl, any of which is substituted or unsubstituted, or hydrogen; and
  $R^X$ and $R^Y$ together with the atoms to which $R^X$ and $R^Y$ are bound form a ring that is substituted or unsubstituted, or a pharmaceutically-acceptable salt thereof.

In some embodiments, $R^1$ is cyano, an imine group, an acyl group, a carboxylic acid group, a carboxaldehyde group, an ester group, an amide group, a hydrazide group, a hydroxamic acid group, a hydroxamic acid ester group, a thioester group, or a thioacid group, any of which is substituted or unsubstituted.

In some embodiments, each $R^2$ and $R^3$ is independently cyano, an imine group, an acyl group, alkyl, alkenyl, alkynyl, a carboxylic acid group, a carboxaldehyde group, an ester group, an amide group, a hydrazide group, a hydroxamic acid group, a hydroxamic acid ester group, a thioester group, a thioacid group, aryl, arylalkyl, heterocyclyl, cycloalkyl, cycloalkenyl, or heteroaryl, any of which is substituted or unsubstituted.

In some embodiments, $R^X$ and $R^Y$ together with the atoms to which $R^X$ and $R^Y$ are bound form a 6-membered or 7-membered ring that is substituted or unsubstituted. In some embodiments, $R^X$ and $R^Y$ together with the atoms to which $R^X$ and $R^Y$ are bound form a 6-membered ring that is unsubstituted. In some embodiments, $R^X$ and $R^Y$ together with the atoms to which $R^X$ and $R^Y$ are bound form a 6-membered ring that is substituted. In some embodiments, $R^X$ and $R^Y$ together with the atoms to which $R^X$ and $R^Y$ are bound form a 6-membered aromatic ring that is unsubstituted. In some embodiments, $R^X$ and $R^Y$ together with the atoms to which $R^X$ and $R^Y$ are bound form a 6-membered aromatic ring that is substituted. In some embodiments, $R^X$ and $R^Y$ together with the atoms to which $R^X$ and $R^Y$ are bound form a benzo ring or a naphtho ring, any of which is substituted or unsubstituted. In some embodiments, $R^X$ and $R^Y$ together with the atoms to which $R^X$ and $R^Y$ are bound form a benzo ring, a [2,1]naphtho ring, a [3,2]naphtho ring, or a [4,3]naphtho ring, any of which is substituted or unsubstituted. In some embodiments, $R^X$ and $R^Y$ together with the atoms to which $R^X$ and $R^Y$ are bound form a naphtho ring that is substituted or unsubstituted. In some embodiments, $R^X$ and $R^Y$ together with the atoms to which $R^X$ and $R^Y$ are bound form a naphtho ring that is substituted. In some embodiments, $R^X$ and $R^Y$ together with the atoms to which $R^X$ and $R^Y$ are bound form a naphtho ring that is unsubstituted. In some embodiments, $R^X$ and $R^Y$ together with the atoms to which $R^X$ and $R^Y$ are bound form a [2,1]naphtho ring that is substituted. In some embodiments, $R^X$ and $R^Y$ together with the atoms to which $R^X$ and $R^Y$ are bound form a [2,1]naphtho ring that is unsubstituted. In some embodiments, $R^X$ and $R^Y$ together with the atoms to which $R^X$ and $R^Y$ are bound form a [3,2]naphtho ring that is substituted. In some embodiments, $R^X$ and $R^Y$ together with the atoms to which $R^X$ and $R^Y$ are bound form a [3,2]naphtho ring that is unsubstituted. In some embodiments, $R^X$ and $R^Y$ together with the atoms to which $R^X$ and $R^Y$ are bound form a

[4,3]naphtho ring that is substituted. In some embodiments, $R^X$ and $R^Y$ together with the atoms to which $R^X$ and $R^Y$ are bound form a [4,3]naphtho ring that is unsubstituted. In some embodiments, $R^X$ and $R^Y$ together with the atoms to which $R^X$ and $R^Y$ are bound form a benzo ring that is substituted. In some embodiments, $R^X$ and $R^Y$ together with the atoms to which $R^X$ and $R^Y$ are bound form a benzo ring that is unsubstituted.

In some embodiments, $R^1$ is cyano, an amide group, a hydrazide group, a hydroxamic acid group, or a hydroxamic acid ester group, any of which is substituted or unsubstituted. In some embodiments, $R^1$ is a hydroxamic acid or a hydroxamic acid ester group. In some embodiments, $R^1$ is a hydroxamic acid.

In some embodiments, each $R^2$ and $R^3$ is independently alkyl, aryl, aryloxy, arylalkyl, arylalkoxy, heterocyclyl, cycloalkyl, cycloalkenyl, or heteroaryl, any of which is substituted or unsubstituted. In some embodiments, each $R^2$ and $R^3$ is independently alkyl, aryl, aryloxy, arylalkyl, or arylalkoxyl, any of which is substituted or unsubstituted.

In some embodiments, $R^1$ is a substituted or unsubstituted hydroxamic acid or hydroxamic acid ester, and $R^2$ is substituted or unsubstituted aryl. In some embodiments, $R^1$ is a substituted or unsubstituted hydroxamic acid or hydroxamic acid ester, and $R^3$ is substituted or unsubstituted aryl or unsubstituted alkyl. In some embodiments, each $R^2$ and $R^3$ is independently substituted or unsubstituted aryl. In some embodiments, $R^1$ is a substituted or unsubstituted hydroxamic acid or hydroxamic acid ester, and each $R^2$ and $R^3$ is independently substituted or unsubstituted aryl.

In some embodiments, $R^1$ is a substituted or unsubstituted hydroxamic acid or hydroxamic acid ester, each $R^2$ and $R^3$ is independently substituted or unsubstituted aryl, and $R^X$ and $R^Y$ together with the atoms to which $R^X$ and $R^Y$ are bound form a 6-membered ring that is substituted or unsubstituted.

In some embodiments, $R^4$ is hydrogen or alkyl that is substituted or unsubstituted. In some embodiments, $R^4$ is hydrogen. In some embodiments, $R^4$ is alkyl that is substituted or unsubstituted. In some embodiments, $R^4$ is alkyl that is unsubstituted. In some embodiments, $R^4$ is methyl, ethyl, n-propyl, or n-butyl or hydrogen.

In some embodiments, the compound is of the formula:

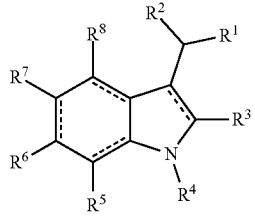

wherein:
each ==== is independently a single bond or a double bond;
$R^1$ is cyano, an imine group, an acyl group, a carboxylic acid group, a carboxaldehyde group, an ester group, an amide group, a hydrazide group, a hydroxamic acid group, a hydroxamic acid ester group, a thioester group, or a thioacid group, any of which is substituted or unsubstituted;
each $R^2$ and $R^3$ is independently cyano, an imine group, an acyl group, alkyl, alkenyl, alkynyl, a carboxylic acid group, a carboxaldehyde group, an ester group, an amide group, a hydrazide group, a hydroxamic acid group, a hydroxamic acid ester group, a thioester group, a thioacid group, aryl, arylalkyl, cycloalkyl, cycloalkenyl, heterocyclyl, or heteroaryl, any of which is substituted or unsubstituted;
$R^4$ is an imine group, an acyl group, alkyl, alkenyl, alkynyl, aryl, arylalkyl, cycloalkyl, cycloalkenyl, heterocyclyl, or heteroaryl, any of which is substituted or unsubstituted, or hydrogen;
each $R^5$, $R^6$, $R^7$, and $R^8$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, or heteroaryl, any of which is substituted or unsubstituted, or halogen or hydrogen; or each $R^5$ and $R^6$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, or heteroaryl, any of which is substituted or unsubstituted, or halogen or hydrogen, and $R^7$ and $R^8$ together with the atoms to which $R^7$ and $R^8$ are bound form a 6-membered ring that is substituted or unsubstituted; or each $R^5$ and $R^8$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, or heteroaryl, any of which is substituted or unsubstituted, or halogen or hydrogen, and $R^6$ and $R^7$ together with the atoms to which $R^6$ and $R^7$ are bound form a 6-membered ring that is substituted or unsubstituted; or each $R^7$ and $R^8$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, or heteroaryl, any of which is substituted or unsubstituted, or halogen or hydrogen, and $R^5$ and $R^6$ together with the atoms to which $R^5$ and $R^6$ are bound form a 6-membered ring that is substituted or unsubstituted.

In some embodiments, $R^1$ is cyano, an amide group, a hydrazide group, a hydroxamic acid group, or a hydroxamic acid ester group, any of which is substituted or unsubstituted. In some embodiments, $R^1$ is cyano, an amide group, a hydroxamic acid group, or a hydroxamic acid ester group.

In some embodiments, each $R^2$ and $R^3$ is independently alkyl, aryl, arylalkyl, cycloalkyl, cycloalkenyl, heterocyclylalkyl, heterocyclylalkenyl, heteroaryl, or heteroarylalkyl, any of which is substituted or unsubstituted. In some embodiments, each $R^2$ and $R^3$ is independently alkyl, aryl, arylalkyl, cycloalkyl, cycloalkenyl, heterocyclylalkyl, heterocyclylalkenyl, heteroaryl, or heteroarylalkyl, any of which is substituted or unsubstituted. In some embodiments, each $R^2$ and $R^3$ is independently alkyl, aryl, or arylalkyl, any of which is substituted or unsubstituted.

In some embodiments, $R^2$ is aryl or arylalkyl, any of which is substituted or unsubstituted; and $R^3$ is independently alkyl, aryl, or arylalkyl, any of which is substituted or unsubstituted. In some embodiments, $R^2$ is unsubstituted aryl or unsubstituted arylalkyl; and $R^3$ is unsubstituted alkyl, unsubstituted aryl, or unsubstituted arylalkyl. In some embodiments, $R^2$ is phenyl that is unsubstituted or substituted; and $R^3$ is alkyl, phenyl, or naphthalenyl.

In some embodiments, $R^1$ is a substituted or unsubstituted hydroxamic acid or hydroxamic acid ester, and $R^2$ is substituted or unsubstituted aryl. In some embodiments, $R^1$ is an unsubstituted hydroxamic acid, and $R^2$ is unsubstituted phenyl. In some embodiments, $R^1$ is an unsubstituted hydroxamic acid, and $R^2$ is substituted phenyl. In some embodiments, $R^1$ is a substituted or unsubstituted hydroxamic acid or hydroxamic acid ester, and $R^3$ is substituted or unsubstituted aryl or unsubstituted alkyl. In some embodiments, each $R^2$ and $R^3$ is independently substituted or unsubstituted aryl. In some embodiments, $R^1$ is a substituted or unsubstituted hydroxamic acid or hydroxamic acid ester, and each $R^2$ and $R^3$ is independently substituted or unsubstituted aryl. In some embodiments, $R^1$ is an unsubstituted hydroxamic acid, $R^2$ is unsubstituted or substituted aryl, and $R^3$ is unsubstituted phenyl or napthalenyl.

In some embodiments, $R^4$ is alkyl that is substituted or unsubstituted, or hydrogen. In some embodiments, $R^4$ is hydrogen. In some embodiments, $R^4$ is alkyl that is substituted or unsubstituted. In some embodiments, $R^4$ is alkyl that is unsubstituted. In some embodiments, $R^4$ is methyl, ethyl, propyl, or butyl. In some embodiments, $R^4$ is methyl, ethyl, n-propyl, or n-butyl.

In some embodiments, each $R^5$, $R^6$, $R^7$, and $R^8$ is independently hydroxyl, sulfhydryl, nitro, cyano, alkyl, alkenyl, alkynyl, an alkoxy group, an alkylamino group, an ether group, or an amine group, any of which is substituted or unsubstituted, or halogen or hydrogen. In some embodiments, each $R^5$, $R^6$, $R^7$, and $R^8$ is hydrogen. In some embodiments, each $R^7$ and $R^8$ is independently hydroxyl, sulfhydryl, nitro, cyano, alkyl, alkenyl, alkynyl, an alkoxy group, an alkylamino group, an ether group, or an amine group, any of which is substituted or unsubstituted, or halogen or hydrogen, and $R^5$ and $R^6$ together with the atoms to which $R^5$ and $R^6$ are bound form a 6-membered ring that is substituted or unsubstituted. In some embodiments, each $R^7$ and $R^8$ are hydrogen, and $R^5$ and $R^6$ together with the atoms to which $R^5$ and $R^6$ are bound form a 6-membered ring that is unsubstituted.

In some embodiments, the compound is of the formula:

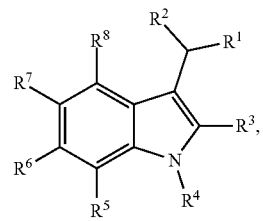

wherein the variables are as defined above.

In some embodiments, $R^1$ is —CN, —C(=O)N($R^{w1}$)O$R^{w2}$, or —C(=O)N($R^{w1}$)($R^{w2}$); wherein each $R^{w1}$ and $R^{w2}$ is independently alkyl, alkenyl, alkynyl, an alkoxy group, aryl, aryloxy, arylalkyl, cycloalkyl, cycloalkenyl, heterocyclylalkyl, heterocyclylalkenyl, heteroaryl, or heteroarylalkyl, any of which is substituted or unsubstituted, or hydrogen. In some embodiments, $R^1$ is —CN, —C(=O)N($R^{w1}$)O$R^{w2}$, or —C(=O)N($R^{w1}$)($R^{w2}$), wherein each $R^{w1}$ and $R^{w2}$ is independently hydrogen or alkyl. In some embodiments, $R^1$ is —CN, —C(=O)NHOH, —C(=O)NHOMe, or —C(=O)NH$_2$.

In some embodiments, $R^2$ is alkyl, alkenyl, alkynyl, aryl, arylalkyl, cycloalkyl, cycloalkenyl, heterocyclylalkyl, heterocyclylalkenyl, heteroaryl, or heteroarylalkyl, any of which is substituted or unsubstituted. In some embodiments, $R^2$ is substituted or unsubstituted aryl. In some embodiments, $R^2$ is substituted or unsubstituted phenyl. In some embodiments, $R^2$ is phenyl substituted with an alkoxy group, a halogen group, an alkylamino group, or an alkyl group. In some embodiments, $R^2$ is 4-substituted phenyl. In some embodiments, $R^2$ is unsubstituted phenyl.

In some embodiments, $R^3$ is alkyl, alkenyl, alkynyl, aryl, arylalkyl, cycloalkyl, cycloalkenyl, heterocyclylalkyl, heterocyclylalkenyl, heteroaryl, or heteroarylalkyl, any of which is substituted or unsubstituted. In some embodiments, $R^3$ is substituted or unsubstituted aryl or substituted or unsubstituted alkyl. In some embodiments, $R^3$ is naphthalenyl. In some embodiments, $R^3$ is methyl, naphthalen-1-yl, naphthalen-2-yl or phenyl. In some embodiments, $R^3$ is naphthalen-1-yl, naphthalen-2-yl or phenyl. In some embodiments, $R^3$ is naphthalen-1-yl or naphthalen-2-yl. In some embodiments, $R^3$ is substituted phenyl. In some embodiments, $R^3$ is unsubstituted phenyl. In some embodiments, $R^3$ is methyl. In some embodiments, $R^3$ is naphthalen-1-yl. In some embodiments, $R^3$ is naphthalen-2-yl.

In some embodiments, each $R^2$ and $R^3$ is independently alkyl, alkenyl, alkynyl, aryl, arylalkyl, cycloalkyl, cycloalkenyl, heterocyclylalkyl, heterocyclylalkenyl, heteroaryl, or heteroarylalkyl, any of which is substituted or unsubstituted. In some embodiments, $R^2$ is unsubstituted or substituted phenyl, and $R^3$ is unsubstituted alkyl or unsubstituted or substituted aryl. In some embodiments, $R^2$ is unsubstituted phenyl, and $R^3$ is methyl or naphthalenyl.

In some embodiments, $R^4$ is alkyl that is substituted or unsubstituted, or hydrogen. In some embodiments, $R^4$ is hydrogen. In some embodiments, $R^4$ is alkyl that is unsubstituted. In some embodiments, $R^4$ is methyl, ethyl, propyl, or butyl. In some embodiments, $R^4$ is n-propyl.

In some embodiments, $R^1$ is —CN, —C(=O)N($R^{w1}$)O$R^{w2}$, or —C(=O)N($R^{w1}$)($R^{w2}$), wherein each $R^{w1}$ and $R^{w2}$ is independently hydrogen or alkyl; $R^2$ is substituted or unsubstituted aryl; and $R^3$ is naphthalen-1-yl, naphthalen-2-yl, or phenyl. In some embodiments, $R^1$ is —CN, —C(=O)N($R^{w1}$)O$R^{w2}$, or —C(=O)N($R^{w1}$)($R^{w2}$), wherein each $R^{w1}$ and $R^{w2}$ is independently hydrogen or alkyl; $R^2$ is phenyl;

and R³ is substituted or unsubstituted aryl. In some embodiments, R¹ is —C(=O)N(R$^{w1}$)OR$^{w2}$, wherein R$^{w1}$ and R$^{w2}$ are hydrogen; and R³ is naphthalen-1-yl, naphthalen-2-yl, or phenyl. In some embodiments, R¹ is —C(=O)N(R$^{w1}$)(R$^{w2}$), wherein R$^{w1}$ and R$^{w2}$ are hydrogen; and R³ is naphthalen-1-yl or naphthalen-2-yl.

In some embodiments, each R⁵, R⁶, R⁷, and R⁸ is hydrogen. In some embodiments, R⁴ is hydrogen or alkyl that is substituted or unsubstituted. In some embodiments, each R⁵, R⁶, R⁷, and R⁸ is hydrogen, and R⁴ is hydrogen or alkyl that is substituted or unsubstituted. In some embodiments, each R⁵, R⁶, R⁷, and R⁸ is hydrogen, and R⁴ is hydrogen or alkyl that is unsubstituted.

In some embodiments, the compound is of the formula:

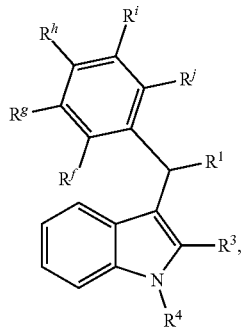

wherein:
R$^f$ is hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclylalkyl, heterocyclylalkenyl, heteroaryl, or heteroarylalkyl, any of which is substituted or unsubstituted, or halogen or hydrogen;

each R$^g$ and R$^h$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclylalkyl, heterocyclylalkenyl, heteroaryl, or heteroarylalkyl, any of which is substituted or unsubstituted, or halogen or hydrogen, or R$^g$ and R$^h$ together with the atoms to which R$^g$ and R$^h$ are bound form a 6-membered ring that is substituted or unsubstituted; and each R$^i$ and R$^j$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclylalkyl, heterocyclylalkenyl, heteroaryl, or heteroarylalkyl, any of which is substituted or unsubstituted, or halogen or hydrogen, or R$^i$ and R$^j$ together with the atoms to which R$^i$ and R$^j$ are bound form a 6-membered ring that is substituted or unsubstituted.

In some embodiments, R³ is alkyl, cycloalkyl, heterocyclylalkyl, aryl, or heteroaryl; any of which is substituted or unsubstituted. In some embodiments, R³ is alkyl or aryl; each of which is substituted or unsubstituted. In some embodiments, R³ is methyl, phenyl, naphthalen-1-yl or naphthalen-2-yl. In some embodiments, R¹ is —CN, —C(=O)NHOH, —C(=O)NHOMe, or —C(=O)NH₂. In some embodiments, R¹ is —CN, —C(=O)NHOH, —C(=O)NHOMe, or —C(=O)NH₂; and R³ is alkyl or aryl. In some embodiments, R¹ is —CN, —C(=O)NHOH, —C(=O)NHOMe, or —C(=O)NH₂; and R³ is methyl, phenyl, naphthalen-1-yl or naphthalen-2-yl.

In some embodiments, each R$^f$, R$^g$, R$^h$, R$^i$, and R$^j$ is independently hydroxyl, sulfhydryl, nitro, cyano, alkyl, alkenyl, alkynyl, an alkoxy group, an alkylamino group, an ether group, or an amine group, any of which is substituted or unsubstituted, or halogen or hydrogen.

In some embodiments, the compound is of the formula:

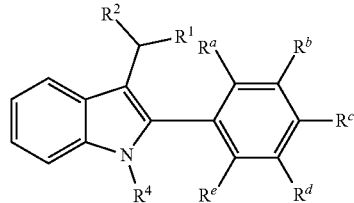

wherein R¹, R², and R⁴ are as defined above, and
R$^a$ is hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclylalkyl, heterocyclylalkenyl, heteroaryl, or heteroarylalkyl, any of which is substituted or unsubstituted, or halogen or hydrogen;

each R$^b$ and R$^c$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclylalkyl, heterocyclylalkenyl, heteroaryl, or heteroarylalkyl, any of which is substituted or unsubstituted, or halogen or hydrogen, or R$^b$ and R$^c$ together with the atoms to which R$^b$ and R$^c$ are bound form a 6-membered ring that is substituted or unsubstituted; and each R$^d$ and R$^e$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclylalkyl, heterocyclylalkenyl, heteroaryl, or heteroarylalkyl, any of which is substituted or unsubstituted, or halogen or hydrogen, or R$^d$ and R$^e$ together with the atoms to which R$^d$ and R$^e$ are bound form a 6-membered ring that is substituted or unsubstituted.

In some embodiments, each R$^a$, R$^b$, R$^c$, R$^d$, and R$^e$ is independently hydroxyl, sulfhydryl, nitro, cyano, alkyl, alkenyl, alkynyl, an alkoxy group, an alkylamino group, an ether group, or an amine group, any of which is substituted or unsubstituted, or halogen or hydrogen.

In some embodiments, R$^d$ and R$^e$ together with the atoms to which R$^d$ and R$^e$ are bound form a 6-membered ring that is substituted or unsubstituted. In some embodiments, R$^d$ and R$^e$ together with the atoms to which R$^d$ and R$^e$ are bound form a 6-membered aromatic ring. In some embodiments, R$^d$ and R$^e$ together with the atoms to which R$^d$ and R$^e$ are bound form a benzo ring. In some embodiments, R$^b$ and R$^c$ together with the atoms to which R$^b$ and R$^c$ are bound form a 6-membered ring that is substituted or unsubstituted. In some embodiments, R$^b$ and R$^c$ together with the atoms to which R$^b$ and R$^c$ are bound form a 6-membered aromatic ring. In some embodiments, R$^b$ and R$^c$ together with the atoms to which R$^b$ and R$^c$ are bound form a benzo ring.

In some embodiments, R$^1$ is —CN, —C(=O)N(R$^{w1}$)OR$^{w2}$, or —C(=O)N(R$^{w1}$)R$^{w2}$, wherein each R$^{w1}$ and R$^{w2}$ is independently alkyl, alkenyl, alkynyl, aryl, arylalkyl, cycloalkyl, cycloalkenyl, heterocyclyl, or heteroaryl, any of which is substituted or unsubstituted, or hydrogen.

In some embodiments, R$^2$ is alkyl, alkenyl, alkynyl, aryl, arylalkyl, cycloalkyl, cycloalkenyl, heterocyclylalkyl, heterocyclylalkenyl, heteroaryl, or heteroarylalkyl. In some embodiments, R$^2$ is aryl or heteroaryl. In some embodiments, R$^2$ is aryl. In some embodiments, R$^2$ is phenyl. In some embodiments, R$^2$ is phenyl substituted with alkyl, alkoxy, alkylamino, or halogen. In some embodiments, R$^2$ is unsubstituted phenyl. In some embodiments, R$^2$ is phenyl substituted at the 4-position with alkyl, alkoxy, alkylamino, or halogen. In some embodiments, R$^2$ is phenyl substituted at the 4-position with methyl, ethyl, isopropyl, methoxy, dimethylamino, fluoro, chloro, or bromo.

In some embodiments, R$^2$ is methyl, phenyl, or naphthalenyl, any of which is substituted or unsubstituted; and IV and R$^b$ together with the atoms to which IV and R$^b$ are bound form 6-membered aromatic ring. In some embodiments, R$^2$ is methyl, phenyl, or naphthalenyl, any of which is substituted or unsubstituted; and R$^c$ and R$^d$ together with the atoms to which R$^c$ and R$^d$ are bound form a 6-membered aromatic ring.

In some embodiments, R$^1$ is —CN, —C(=O)NHOH, —C(=O)NHOMe, or —C(=O)NH$_2$. In some embodiments, R$^1$ is —CN, —C(=O)NHOH, —C(=O)NHOMe, or —C(=O)NH$_2$; and R$^2$ is aryl. In some embodiments, R$^1$ is —CN, —C(=O)NHOH, —C(=O)NHOMe, or —C(=O)NH$_2$; R$^2$ is phenyl; and IV and R$^b$ together with the atoms to which IV and R$^b$ are bound form a 6-membered ring that is substituted or unsubstituted, or R$^c$ and R$^d$ together with the atoms to which R$^c$ and R$^d$ are bound form a 6-membered ring that is substituted or unsubstituted.

In some embodiments, the compound is of the formula:

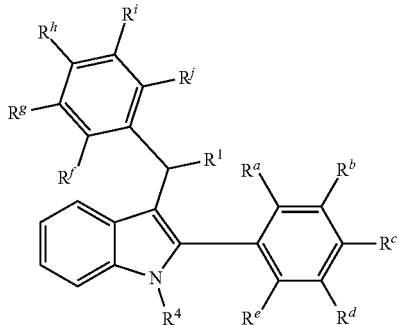

wherein:
each R$^a$ and R$^f$ is hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclylalkyl, heterocyclylalkenyl, heteroaryl, or heteroarylalkyl, any of which is substituted or unsubstituted, or halogen or hydrogen;

each R$^b$ and R$^c$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclylalkyl, heterocyclylalkenyl, heteroaryl, or heteroarylalkyl, any of which is substituted or unsubstituted, or halogen or hydrogen, or R$^b$ and R$^c$ together with the atoms to which R$^b$ and R$^c$ are bound form a 6-membered ring that is substituted or unsubstituted;

each R$^d$ and R$^e$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclylalkyl, heterocyclylalkenyl, heteroaryl, or heteroarylalkyl, any of which is substituted or unsubstituted, or halogen or hydrogen, or R$^d$ and R$^e$ together with the atoms to which R$^d$ and R$^e$ are bound form a 6-membered ring that is substituted or unsubstituted;

each R$^g$ and R$^h$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclylalkyl, heterocyclylalkenyl, heteroaryl, or heteroarylalkyl, any of which is substituted or unsubstituted, or halogen or hydrogen, or R$^g$ and R$^h$ together with the atoms to which R$^g$ and R$^h$ are bound form a 6-membered ring that is substituted or unsubstituted; and each R$^i$ and R$^j$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclylalkyl, heterocyclylalkenyl, heteroaryl, or heteroarylalkyl, any of which is substituted or unsubstituted, or halogen or hydrogen, or R$^i$ and R$^j$ together with the atoms to which R$^i$ and R$^j$ are bound form a 6-membered ring that is substituted or unsubstituted.

In some embodiments, each R$^a$, R$^b$, R$^c$, R$^d$, R$^e$ R$^f$, R$^g$, R$^h$, R$^i$, and R$^j$ is independently hydroxyl, sulfhydryl, nitro, cyano, alkyl, alkenyl, alkynyl, an alkoxy group, an ether group, or an amine group, any of which is substituted or unsubstituted, or halogen or hydrogen.

In some embodiments, each R$^a$, R$^b$, R$^e$, R$^f$, R$^g$, R$^h$, R$^i$, and R$^j$ is independently hydroxyl, sulfhydryl, nitro, cyano, alkyl, alkenyl, alkynyl, an alkoxy group, an ether group, or an amine group, any of which is substituted or unsubstituted, or halogen or hydrogen, and R$^d$ and R$^e$ together with the atoms to which R$^d$ and R$^e$ are bound form a 6-membered ring that is substituted or unsubstituted.

In some embodiments, each R$^a$ R$^d$, R$^e$ R$^f$, R$^g$, R$^h$, R$^i$, and R$^j$ is independently hydroxyl, sulfhydryl, nitro, cyano, alkyl, alkenyl, alkynyl, an alkoxy group, an ether group, or an amine group, any of which is substituted or unsubstituted, or halogen or hydrogen, and R$^b$ and R$^e$ together with the atoms to which R$^b$ and R$^e$ are bound form a 6-membered ring that is substituted or unsubstituted.

In some embodiments, the compound is of the formula:

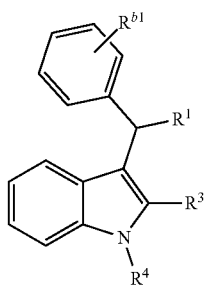

wherein:
R$^3$ is

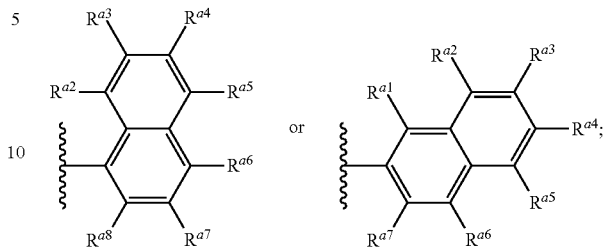

wherein each R$^{b1}$, R$^{a1}$, R$^{a2}$, R$^{a3}$, R$^{a4}$, R$^{a5}$, R$^{a6}$, R$^{a7}$ and R$^{a8}$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, or heteroaryl any of which is substituted or unsubstituted, or halogen or hydrogen.

In some embodiments, each R$^{b1}$, R$^{a1}$, R$^{a2}$, R$^{a3}$, R$^{a4}$, R$^{a5}$, R$^{a6}$, R$^{a7}$ and R$^{a8}$ is independently hydroxyl, sulfhydryl, nitro, cyano, alkyl, alkenyl, alkynyl, an alkoxy group, an alkylamino group, an ether group, or an amine group, any of which is substituted or unsubstituted, or halogen or hydrogen. In some embodiments, each R$^{b1}$, R$^{a1}$, R$^{a2}$, R$^{a3}$, R$^{a4}$, R$^{a5}$, R$^{a6}$, R$^{a7}$ and R$^{a8}$ is hydrogen.

In some embodiments, each R$^{b1}$, R$^{a1}$, R$^{a2}$, R$^{a3}$, R$^{a4}$, R$^{a5}$, R$^{a6}$, R$^{a7}$ and R$^{a8}$ is hydrogen, and R$^4$ is alkyl or hydrogen. In some embodiments, each R$^{b1}$, R$^{a1}$, R$^{a2}$, R$^{a3}$, R$^{a4}$, R$^{a5}$, R$^{a6}$, R$^{a7}$ and R$^{a8}$ is hydrogen; R$^3$ is aryl; and R$^4$ is alkyl or hydrogen. In some embodiments, each R$^{b1}$, R$^{a1}$, R$^{a2}$, R$^{a3}$, R$^{a4}$, R$^{a5}$, R$^{a6}$, R$^{a7}$ and R$^{a8}$ is hydrogen; R$^1$ is an amide group, a cyano group, a hydroxamic acid group, or a hydroxamic acid ester group; R$^3$ is aryl or alkyl; and R$^4$ is alkyl or hydrogen. In some embodiments each R$^{b1}$, R$^{a1}$, R$^{a2}$, R$^{a3}$, R$^{a4}$, R$^{a5}$, R$^{a6}$, R$^{a7}$ and R$^{a8}$ is hydrogen; R$^1$ is —CN, —C(=O)NHOH, —C(=O)NHOMe, or —C(=O)NH$_2$; R$^3$ is methyl, phenyl, naphthalen-1-yl, or naphthalen-2-yl; and R$^4$ is methyl, ethyl, n-propyl, n-butyl, or hydrogen.

In some embodiments, the compound is of the formula:

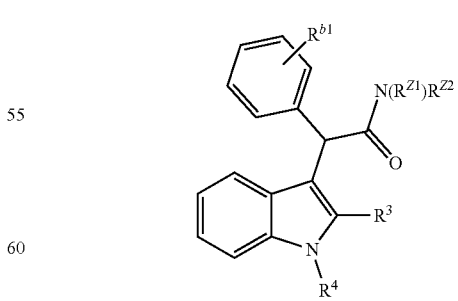

wherein:
each R$^{Z1}$ and R$^{Z2}$ is independently hydroxyl, an acyl group, an acyloxy group, alkyl, alkenyl, alkynyl, an alkoxy group, an ether group, a carboxylic acid group, a carboxaldehyde group, an ester group, an amine group, an amide group, aryl, aryloxy, arylalkyl, arylalkoxy, heterocyclyl, cycloalkyl, cycloalkenyl, or heteroaryl, any of which is substituted or unsubstituted, or hydrogen;

$R^{c1}$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclylalkyl, heterocyclylalkenyl, heteroaryl, or heteroarylalkyl, any of which is substituted or unsubstituted, or halogen or hydrogen.

In some embodiments, each $R^{Z1}$ and $R^{Z2}$ is independently hydroxyl, alkyl, alkenyl, alkynyl, an alkoxy group, an ether group, an amine group, aryl, aryloxy, arylalkyl, arylalkoxy, heterocyclyl, cycloalkyl, cycloalkenyl, or heteroaryl, any of which is substituted or unsubstituted, or hydrogen.

In some embodiments, each $R^{Z1}$ and $R^{Z2}$ is independently hydrogen, hydroxyl, alkyl, or an alkoxy group. In some embodiments, $R^{Z1}$ is hydrogen, and $R^{Z2}$ is hydrogen, hydroxyl, alkyl, or an alkoxy group. In some embodiments, $R^{Z1}$ is hydrogen, $R^{Z2}$ is hydrogen, hydroxyl, alkyl, or an alkoxy group, $R^3$ is alkyl or aryl, and $R^4$ is alkyl or hydrogen.

In some embodiments, $R^{c1}$ and $R^{Z1}$ are hydrogen; and $R^{Z2}$ is hydroxyl. In some embodiments, $R^{c1}$ and $R^{Z1}$ are hydrogen, and $R^{Z2}$ is methoxy. In some embodiments, $R^{c1}$ and $R^{Z1}$ are hydrogen; and $R^{Z2}$ is methyl. In some embodiments, $R^{c1}$, $R^{Z1}$, and $R^{Z2}$ are hydrogen.

In some embodiments, the compound is of the formula:

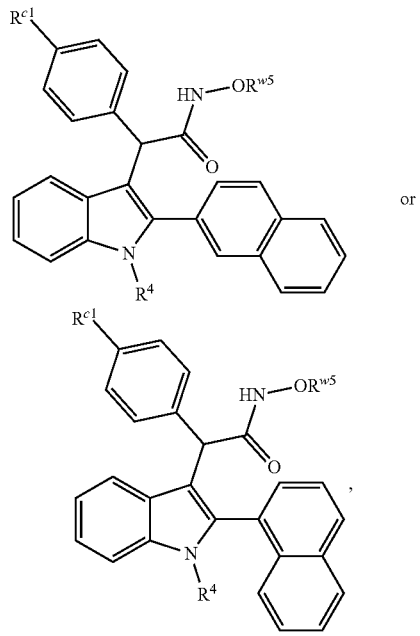

or wherein:
$R^{w5}$ is hydrogen or alkyl;
$R^{c1}$ is hydrogen, alkyl, alkylamino, or alkoxy; and
$R^4$ is hydrogen or alkyl.

In some embodiments, $R^{w5}$ is hydrogen or methyl.

In some embodiments, $R^{c1}$ is hydrogen, methyl, isopropyl, —NMe$_2$, or —OMe. In some embodiments, $R^{c1}$ is hydrogen.

In some embodiments, $R^4$ is hydrogen, methyl, ethyl, propyl, or butyl. In some embodiments, $R^4$ is hydrogen. In some embodiments, $R^4$ is n-propyl.

In some embodiments, $R^{w5}$, $R^{c1}$, and $R^4$ are hydrogen. In some embodiments, $R^{w5}$ and $R^{c1}$ are hydrogen, and $R^4$ is methyl.

In some embodiments, a compound of the disclosure is one of the following:

N-hydroxy-2-phenyl-2-(2-phenyl-1H-indol-3-yl)acetamide;

N-hydroxy-2-(2-methyl-1H-indol-3-yl)-2-phenylacetamide;

N-hydroxy-2-(4-isopropylphenyl)-2-(2-(naphthalen-2-yl)-1H-indol-3-yl)acetamide;

N-hydroxy-2-(1-methyl-2-(naphthalen-2-yl)-1H-indol-3-yl)-2-phenylacetamide;

2-(2-(naphthalen-2-yl)-1H-indol-3-yl)-2-phenylacetonitrile;

2-(4-(dimethylamino)phenyl)-N-hydroxy-2-(2-(naphthalen-2-yl)-1H-indol-3-yl)acetamide;

N-hydroxy-2-(2-(naphthalen-2-yl)-1H-indol-3-yl)-2-phenylacetamide;

N-hydroxy-2-(2-(naphthalen-1-yl)-1H-benzo[g]indol-3-yl)-2-phenylacetamide;

N-hydroxy-2-(4-methoxyphenyl)-2-(2-(naphthalen-2-yl)-1H-indol-3-yl)acetamide;

2-(2-(naphthalen-2-yl)-1H-indol-3-yl)-2-phenylacetamide; or 2-(1-butyl-2-(naphthalen-2-yl)-1H-indol-3-yl)-N-hydroxy-2-phenylacetamide.

In some embodiments, a compound of the disclosure is one of the following:

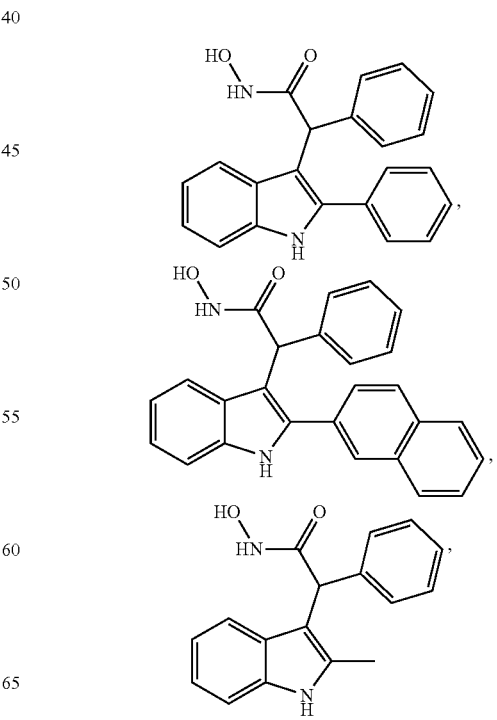

23

-continued

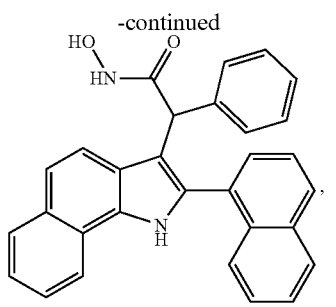

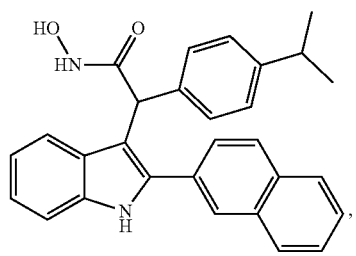

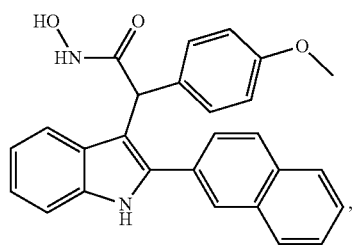

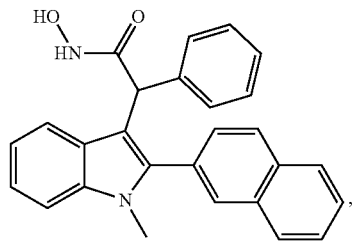

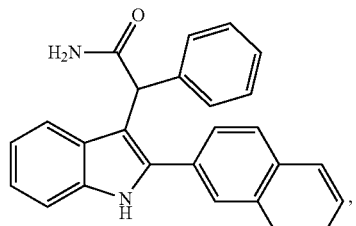

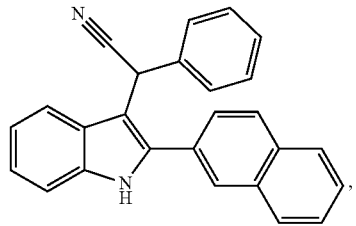

24

-continued

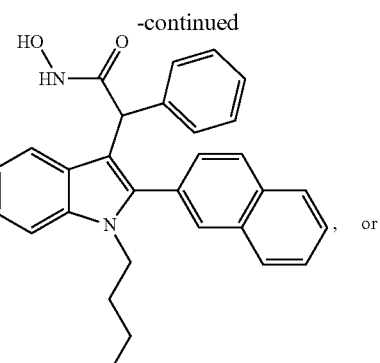

, or

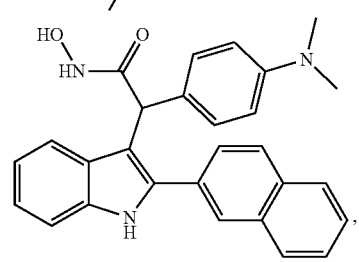

, or a pharmaceutically-acceptable salt thereof.

Compounds herein can include all stereoisomers, enantiomers, diastereomers, mixtures, racemates, atropisomers, and tautomers thereof.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, ureido groups, epoxy groups, and ester groups.

Non-limiting examples of alkyl and alkylene groups include straight, branched, and cyclic alkyl and alkylene groups. An alkyl or alkylene group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of substituted alkyl groups includes hydroxymethyl, chloromethyl, trifluoromethyl, aminomethyl, 1-chloroethyl, 2-hydroxyethyl, 1,2-difluoroethyl, and 3-carboxypropyl.

Non-limiting examples of cyclic alkyl groups include cyclopropyl, cyclobutyl, cyclopentyl, cyclohexyl, cycloheptlyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups. Non-limiting examples of cyclic alkyl groups include cyclopropyl, 2-methyl-cycloprop-1-yl, cycloprop-2- en-1-yl, cyclobutyl, 2,3-dihydroxycyclobut-1-yl, cyclobut-2-en-1-yl, cyclopentyl, cyclopent-2-en-1-yl, cyclopenta-2,4-dien-1-yl, cyclohexyl, cyclohex-2-en-1-yl, cycloheptyl, cyclooctanyl, 2,5-dimethylcyclopent-1-yl, 3,5-dichlorocyclohex-1-yl, 4-hydroxycyclohex-1-yl, 3,3,5-trimethylcyclohex-1-yl, octahydropentalenyl, octahydro-1H-indenyl, 3a,4,5,6,7,7a-hexahydro-3H-inden-4-yl, decahydroazulenyl, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkenyl and alkenylene groups include ethenyl, prop-1-en-1-yl, isopropenyl, but-1-en-4-yl; 2-chloroethenyl, 4-hydroxybuten-1-yl, 7-hydroxy-7-methyloct-4-en-2-yl, and 7-hydroxy-7-methyloct-3,5-dien-2-yl.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkynyl or alkynylene groups include ethynyl, prop-2-yn-1-yl, prop-1-yn-1-yl, and 2-methyl-hex-4-yn-1-yl; 5-hydroxy-5-methylhex-3-yn-1-yl, 6-hydroxy-6-methylhept-3-yn-2-yl, and 5-hydroxy-5-ethylhept-3-yn-1-yl.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl. Non-limiting examples of substituted aryl groups include 3,4-dimethylphenyl, 4-tert-butylphenyl, 4-cyclopropylphenyl, 4-diethylaminophenyl, 4-(trifluoromethyl)phenyl, 4-(difluoromethoxy)-phenyl, 4-(trifluoromethoxy)phenyl, 3-chlorophenyl, 4-chlorophenyl, 3,4-dichlorophenyl, 2-fluorophenyl, 2-chlorophenyl, 2-iodophenyl, 3-iodophenyl, 4-iodophenyl, 2-methylphenyl, 3-fluorophenyl, 3-methylphenyl, 3-methoxyphenyl, 4-fluorophenyl, 4-methylphenyl, 4-methoxyphenyl, 2,3-difluorophenyl, 3,4-difluorophenyl, 3,5-difluorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, 3,5-dimethoxyphenyl, 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, 2,4,6-trichlorophenyl, 2,3-dimethylphenyl, 2,4-dimethylphenyl, 2,5-dimethylphenyl, 2,6-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethylphenyl, 4-ethylphenyl, 2,3-di ethylphenyl, 2,4-diethylphenyl, 2,5-diethylphenyl, 2,6-diethylphenyl, 3,4-diethylphenyl, 2,3,4-tri ethylphenyl, 2,3,5-triethylphenyl, 2,3,6-triethylphenyl, 2,4,5-triethylphenyl, 2,4,6-triethylphenyl, 2-isopropylphenyl, 3-isopropylphenyl, and 4-isopropylphenyl.

Non-limiting examples of substituted aryl groups include 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino)phenyl, 3-(N,N-dimethylamino)phenyl, 3-(N-ethylamino)phenyl, 3-(N,N-diethylamino)phenyl, 4-aminophenyl, 4-(N-methylamino)phenyl, 4-(N,N-dimethylamino)phenyl, 4-(N-ethylamino)phenyl, and 4-(N,N-diethylamino)phenyl.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

Non-limiting examples of heterocycles include: heterocyclic units having a single ring containing one or more heteroatoms, non-limiting examples of which include, diazirinyl, aziridinyl, azetidinyl, pyrazolidinyl, imidazolidinyl, oxazolidinyl, isoxazolinyl, thiazolidinyl, isothiazolinyl, oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl, 2,3,4,5-tetrahydro-1H-azepinyl, 2,3-dihydro-1H-indole, and 1,2,3,4-tetrahydroquinoline; and ii) heterocyclic units having 2 or more rings one of which is a heterocyclic ring, non-limiting examples of which include hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, and decahydro-1H-cycloocta[b]pyrrolyl.

Non-limiting examples of heteroaryl include: i) heteroaryl rings containing a single ring, non-limiting examples of which include, 1,2,3,4-tetrazolyl, [1,2,3]triazolyl, [1,2,4]triazolyl, triazinyl, thiazolyl, 1H-imidazolyl, oxazolyl, isoxazolyl, isothiazolyl, furanyl, thiophenyl, pyrimidinyl, 2-phenylpyrimidinyl, pyridinyl, 3-methylpyridinyl, and 4-dimethylaminopyridinyl; and ii) heteroaryl rings containing 2 or more fused rings one of which is a heteroaryl ring, non-limiting examples of which include: 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 4,5,6,7-tetrahydro-1-H-indolyl, quinoxalinyl, quinazolinyl, quinolinyl, 8-hydroxy-quinolinyl, and isoquinolinyl.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

In some embodiments, the compounds of the invention show non-lethal toxicity.

Pharmaceutically-Acceptable Salts.

The invention provides the use of pharmaceutically-acceptable salts of any therapeutic compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Pharmaceutical Compositions of the Invention.

A pharmaceutical composition of the invention can be used, for example, before, during, or after treatment of a subject with, for example, another pharmaceutical agent.

Subjects can be, for example, elderly adults, adults, adolescents, pre-adolescents, children, toddlers, infants, neonates, and non-human animals. In some embodiments, a subject is a patient.

A pharmaceutical composition of the invention can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active compounds with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N,N'-bis(2-ethanesulfonic acid) buffer (PIPES), and saline sodium citrate buffer (SSC). Non-limiting examples of co-solvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compounds of the invention can be applied topically to the skin, or a body cavity, for example, oral, vaginal, bladder, cranial, spinal, thoracic, or pelvic cavity of a subject. The compounds of the invention can be applied to an accessible body cavity.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, can be melted.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulations can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include liquid, powder, gel, nanosuspension, nanoparticle, microgel, aqueous or oily suspensions, emulsion, and any combination thereof.

Non-limiting examples of pharmaceutically-acceptable excipients suitable for use in the invention include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Multiple therapeutic agents can be administered in any order or simultaneously. In some embodiments, a compound of the invention is administered in combination with, before, or after treatment with another therapeutic agent. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein.

A compound can be administered as soon as is practical after the onset of a disease or condition is detected or suspected, and for a length of time necessary for the treatment of the disease, such as, for example, from about 1 month to about 3 months. In some embodiments, the length of time a compound can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anticholinergics/antispasmotics, antidiabetic agents, antihypertensive agents, antineoplastics, cardiovascular agents, central nervous system agents, coagulation modifiers, hormones, immunologic agents, immunosuppressive agents, and ophthalmic preparations.

Compounds can be delivered via liposomal technology. The use of liposomes as drug carriers can increase the therapeutic index of the compounds. Liposomes are composed of natural phospholipids and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells.

Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a dose can be expressed in terms of an amount of the drug divided by the mass of the subject, for example, milligrams of drug per kilograms of subject body mass. In some embodiments, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg.

Diseases.

In some embodiments, compounds of the invention can be used to treat a parasitic infection in a subject. A compound of the invention can, for example, eradicate intracellular mammalian and human parasites.

Non-limiting examples of parasitic infections that can be treated by a compound of the disclosure include: Acanthamoeba infection, Acanthamoeba keratitis infection, African sleeping sickness (African trypanosomiasis), Alveolar Echinococcosis (Echinococcosis, Hydatid disease), Amebiasis (*Entamoeba histolytica* infection), American trypanosomiasis (Chagas disease), Ancylostomiasis (hookworm), Angiostrongyliasis (*Angiostrongylus* infection), Anisakiasis (*Anisakis* infection, *pseudoterranova* infection), Ascariasis (*Ascaris* infection, intestinal roundworms), Babesiosis (*Babesia* infection), Balantidiasis (*Balantidium* infection), *Balamuthia*, Baylisascariasis (*Baylisascaris* infection, raccoon roundworm), bed bugs, *Bilharzia* (Schistosomiasis), *Blastocystis hominis* infection, body lice infestation (pediculosis), Capillariasis (*Capillaria* infection), Cercarial Dermatitis (Swimmer's itch), *Chilomastix mesnili* infection, (nonpathogenic intestinal protozoa), Clonorchiasis (*Clonorchis* infection), Cutaneous larva migrans (Ancylostomiasis, hookworm), pubic lice, Cryptosporidiosis (*Cryptosporidium* infection), Cyclosporiasis (*Cyclospora* infection), Cysticercosis (neurocysticercosis), Cystoisospora infection (cystoisosporiasis, formerly *Isospora* infection), *Dientamoeba fragilis* infection, Diphyllobothriasis (*Diphyllobothrium* infection), *Dipylidium caninum* infection (dog or cat tapeworm infection), Dirofilariasis (*Dirofilaria* infection), DPDx, Dracunculiasis (Guinea Worm Disease), Echinococcosis (Cystic, Alveolar Hydatid Disease), Elephantiasis (Filariasis, Lymphatic Filariasis), *Endolimax nana* infection (Nonpathogenic intestinal Protozoa), *Entamoeba coli* infection (Nonpathogenic Intestinal Protozoa), *Entamoeba dispar* infection (Nonpathogenic Intestinal Protozoa), *Entamoeba hartmanni* infection (Nonpathogenic Intestinal Protozoa), *Entamoeba histolytica* infection (Amebiasis), *Entamoeba polecki*, Enterobiasis (Pinworm infection), Fascioliasis (*Fasciola* infection), Fasciolopsiasis (*Fasciolopsis* infection), Filariasis (Lymphatic Filariasis, Elephantiasis), Giardiasis (*Giardia* infection), Gnathostomiasis (*Gnathostoma* infection), head lice infestation (Pediculosis), Heterophyiasis (*Heterophyes* infection), Hydatid Disease (Cystic, Alveolar Echinococcosis), Hymenolepiasis (*Hymenolepis* Infection), Intestinal Roundworms (Ascariasis, *Ascaris* infection), *Iodamoeba buetschlii* infection (Nonpathogenic Intestinal Protozoa), Kala-azar (Leishmaniasis, *Leishmania* infection), Liver Flukes (Clonorchiasis, Opisthorchiasis, Fascioliasis), Loiasis (*Loa loa* infection), Malaria (*Plasmodium* infection), Microsporidiosis (microsporidia infection), Mite Infestation (Scabies), Myiasis, *Naegleria* infection, Neurocysticercosis (Cysticercosis), nonpathogenic intestinal protozoa, Ocular Larva Migrans (Toxocariasis, *Toxocara* infection, Visceral Larva Migrans), Onchocerciasis (River Blindness), Opisthorchiasis (*Opisthorchis* infection), Paragonimiasis (*Paragonimus* infection), pediculosis, Pthiriasis (Pubic Lice infestation), *Pneumocystis jirovecii* Pneumonia, Sappinia, Sarcocystosis (Sarcocystosis infection), scabies, Schistosomiasis (*Bilharzia*), Soil-transmitted Helminths, Strongyloidiasis (*Strongyloides* infection), Taeniasis (*Taenia* infection, Tapeworm Infection), Toxoplasmosis (*Toxoplasma* infection), Trichinellosis (Trichinosis), Trichomoniasis (*Trichomonas* infection), and Trichuriasis (Whipworm Infection, *Trichuris* infection).

Subjects can be, for example, elderly adults, adults, adolescents, pre-adolescents, children, toddlers, infants, and non-human animals. In some embodiments, a subject is a patient. Non-human animal subjects can be, for example, a mouse, a rat, a chicken, a rabbit, a dog, a cat, or a cow.

EXAMPLES

Example 1: Compounds Tested for Efficacy in Treating Parasitic Infections

TABLE 1 shows compounds that were tested for efficacy in treating parasitic infections.

TABLE 1

| Compound Number | Compound Structure | IUPAC |
| --- | --- | --- |
| 1 | 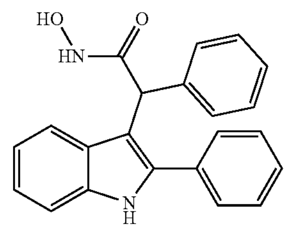 [SMILES: O=C(NO)C(c1ccccc1)c1c(-c2ccccc2)[nH]c2ccccc12] | N-hydroxy-2-phenyl-2-(2-phenyl-1H-indol-3-yl)acetamide |
| 2 | 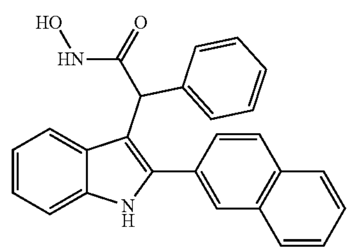 | N-hydroxy-2-(2-(naphthalen-2-yl)-1H-indol-3-yl)-2-phenylacetamide |
| 3 | 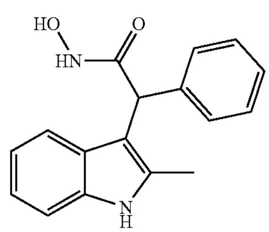 [SMILES: Cc1[nH]c2ccccc2c1C(C(=O)NO)c1ccccc1] | N-hydroxy-2-(2-methyl-1H-indol-3-yl)-2-phenylacetamide |
| 4 | 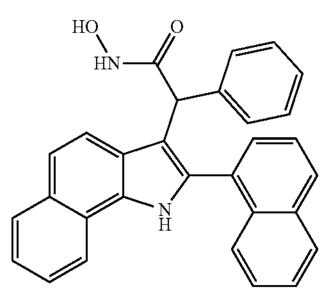 [SMILES: O=C(NO)C(c1ccccc1)c1c(-c2cccc3ccccc23)[nH]c2c1ccc1ccccc12] | N-hydroxy-2-(2-(naphthalen-1-yl)-1H-benzo[g]indol-3-yl)-2-phenylacetamide |

TABLE 1-continued

| Compound Number | Compound Structure | IUPAC |
|---|---|---|
| 5 | 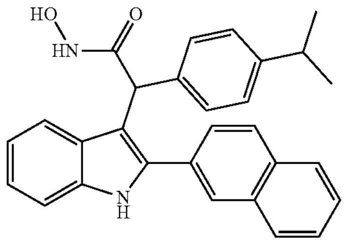 [SMILES: CC(C)c1ccc(C(C(=O)NO)c2c(-c3ccc4ccccc4c3)[nH]c3ccccc23)cc1] | N-hydroxy-2-(4-isopropylphenyl)-2-(2-(naphthalen-2-yl)-1H-indol-3-yl)-acetamide |
| 6 | 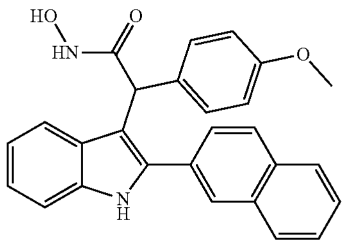 [SMILES: COc1ccc(C(C(=O)NO)c2c(-c3ccc4ccccc4c3)[nH]c3ccccc23)cc1] | N-hydroxy-2-(4-methoxyphenyl)-2-(2-(naphthalen-2-yl)-1H-indol-3-yl)-acetamide |
| 7 | 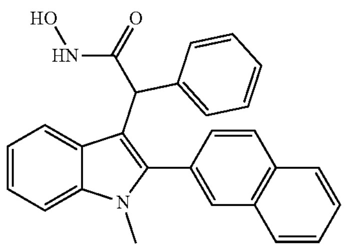 [SMILES: Cn1c(-c2ccc3ccccc3c2)c(C(C(=O)NO)c2ccccc2)c2ccccc21] | N-hydroxy-2-(1-methyl-2-(naphthalen-2-yl)-1H-indol-3-yl)-2-phenylacetamide |
| 8 | 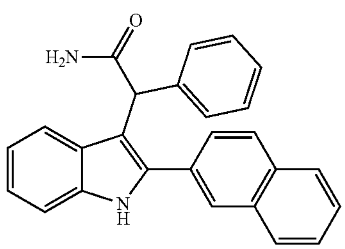 [SMILES: NC(=O)C(c1ccccc1)c1c(-c2ccc3ccccc3c2)[nH]c2ccccc12] | 2-(2-(naphthalen-2-yl)-1H-indol-3-yl)-2-phenylacetamide |
| 9 | 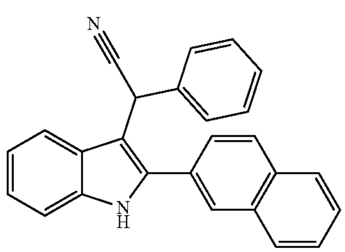 [SMILES: N#CC(c1ccccc1)c1c(-c2ccc3ccccc3c2)[nH]c2ccccc12] | 2-(2-(naphthalen-2-yl)-1H-indol-3-yl)-2-phenylacetonitrile |
| 10 | 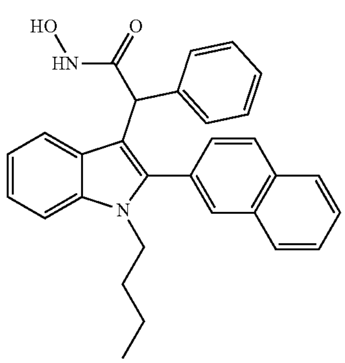 [SMILES: CCCCn1c(-c2ccc3ccccc3c2)c(C(C(=O)NO)c2ccccc2)c2ccccc21] | 2-(1-butyl-2-(naphthalen-2-yl)-1H-indol-3-yl)-N-hydroxy-2-phenyl-acetamide |

TABLE 1-continued

| Compound Number | Compound Structure | IUPAC |
|---|---|---|
| 11 | (structure) | 2-(4-(dimethylamino)-phenyl)-N-hydroxy-2-(2-(naphthalen-2-yl)-1H-indol-3-yl)-acetamide |

Example 2: Sub-Cellular Localization of Compound 2

HeLa cells were cultured and incubated with 15 μM Compound 2, MitoTracker Red to stain mitochondria, and 4′,6-diamidino-2-phenylindole (DAPI) to stain cell nuclei. Images were then taken of cultured cells 6 hours and 48 hours after the cells were treated with Compound 2. The data show that Compound 2 colocalized to the mitochondria of HeLa cells.

FIG. 1 PANEL A shows a phase contrast microscopy image of HeLa cells 6 hours after treatment with Compound 2. FIG. 1 PANEL B shows an image of HeLa cells 6 hours after treatment with Compound 2 and DAPI stain. FIG. 1 PANEL C shows an image of HeLa cells 6 hours after treatment with MitoTracker Red and DAPI stain. FIG. 1 PANEL D shows an overlay image of HeLa cells 6 hours after treatment with Compound 2. FIG. 1 PANEL E shows an intensity quantification plot of the images of HeLa cells 6 hours after treatment with Compound 2. FIG. 1 PANEL F shows a co-localization plot of HeLa cells 6 hours after treatment with Compound 2 and MitoTracker Red stain.

FIG. 1 PANEL G shows a phase contrast microscopy image of HeLa cells 48 hours after treatment with Compound 2. FIG. 1 PANEL H shows an image of HeLa cells 48 hours after treatment with Compound 2 and DAPI stain. FIG. 1 PANEL I shows an image of HeLa cells 48 hours after treatment with MitoTracker Red and DAPI stain. FIG. 1 PANEL J shows an overlay image of HeLa cells 48 hours after treatment with Compound 2. FIG. 1 PANEL K shows an intensity quantification plot of the images of HeLa cells 48 hours after treatment with Compound 2. FIG. 1 PANEL L shows a co-localization plot of HeLa cells 48 hours after treatment with Compound 2 and MitoTracker Red stain.

Jurkat cells were used to test the ability of Compound 2 to change the voltage-dependent uptake of MitTracker Red stain and to affect ATP production. $10^5$ Jurkat cells/mL were treated with 0 μM, 10 μM, 20 μM, 30 μM, and 40 μM Compound 2 for 0.5 hr, 1 hr, 2 hr, 3 hr, 6 hr, and 8 hr. The cells were then stained with MitoTracker Red stain and analyzed by flow cytometry to measure the voltage-dependent uptake of MitoTracker Red stain. $10^5$ Jurkat cells/mL were also treated with 0 μM, 5 μM, 15 μM, and 25 μM Compound 2 for 2 hr, 4 hr, and 6 hr. The cells were treated with MitoTracker Red stain and analyzed for relative light units (RLUs) to determine changes in ATP production.

Figure 2:
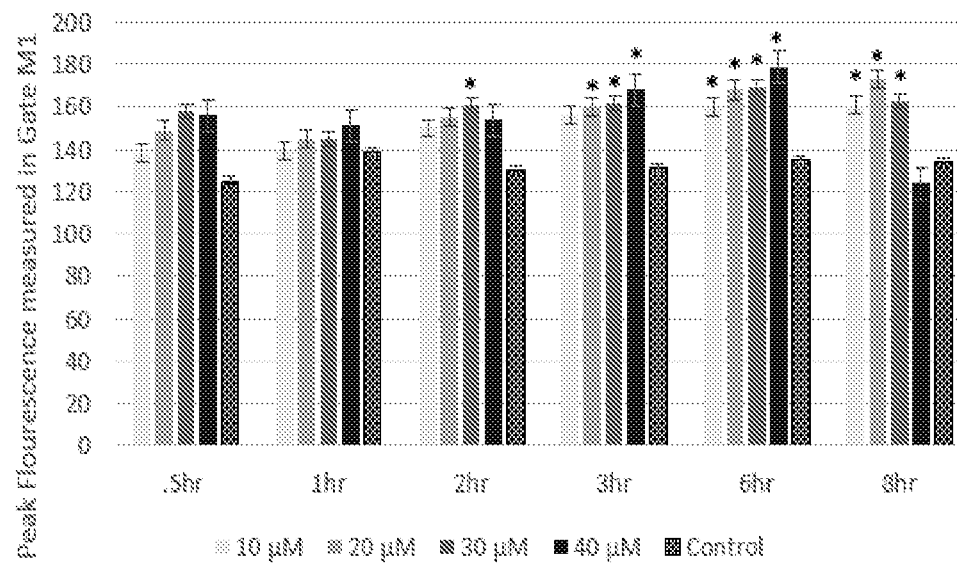
FIG. 2 PANEL A shows a graph of Compound 2 dose-dependent changes in the uptake of MitoTracker Red in Jurkat cells as measured by peak fluorescence.
Figure 2:
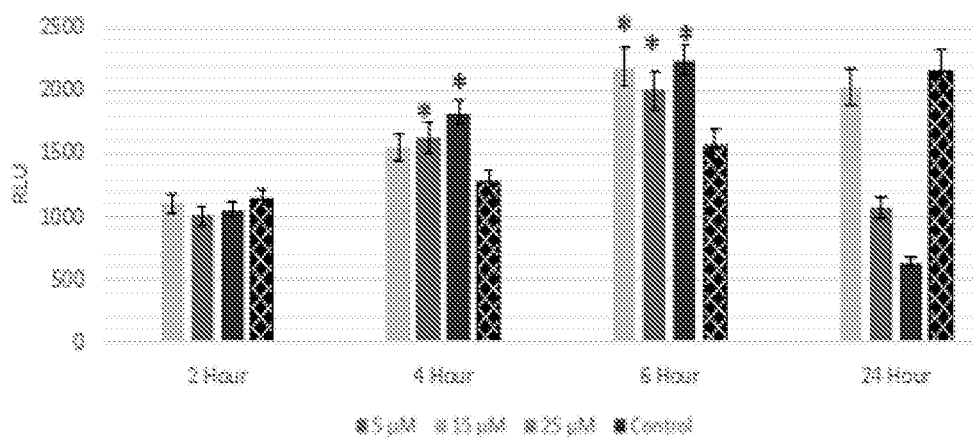

FIG. 2 PANEL A shows a graph of Compound 2 dose-dependent changes in the uptake of MitoTracker Red in Jurkat cells as measured by peak fluorescence. FIG. 2 PANEL B shows a graph of Compound 2 dose-dependent changes in ATP production as measured by RLUs.

Example 3: Compound Toxicity Toward T. cruzi Epimastigotes

A 1:20 working dilution of T. cruzi epimastigotes was prepared in LIT1029 medium from a saturated (~4×10$^6$ cells/mL) culture. 100 μL of the 1:20 working dilution was plated, and the epimastigotes were incubated with a compound of the disclosure at varying concentrations for 48 hours at 30° C. Following T. cruzi epimastigote treatment with a compound of the disclosure, the toxicity of compounds towards T. cruzi epimastigotes was visually assessed. T. cruzi death was determined to have occurred if a lack of cells or a lack of motility was seen in the T. cruzi culture.

TABLE 2 shows the compounds of the disclosure tested and indicates the toxicity of each compound towards T. cruzi at 100 μM. TABLE 3 shows the concentration for the compounds of the disclosure at which T. cruzi epimastigote death was greater than or equal to ~99%.

TABLE 2

| Compound | T. cruzi death @ 100 μM |
|---|---|
| Compound 1 | 100% |
| Compound 3 | 0% |
| Compound 4 | 0% |
| Compound 6 | 0% |
| Compound 7 | 100% |
| Compound 8 | 100% |
| Compound 9 | 100% |
| Compound 10 | >50% |
| Compound 11 | 100% |

TABLE 3

| Compound | Concentration at which T. cruzi epimastigote death is greater than or equal to ~99% |
|---|---|
| Compound 1 | 100 μM |
| Compound 2 | 6 μM |
| Compound 7 | ≥100 μM |
| Compound 8 | 50 μM |
| Compound 9 | ≥100 μM |
| Compound 10 | 25 μM |
| Compound 11 | 100 μM |

Figure 3:
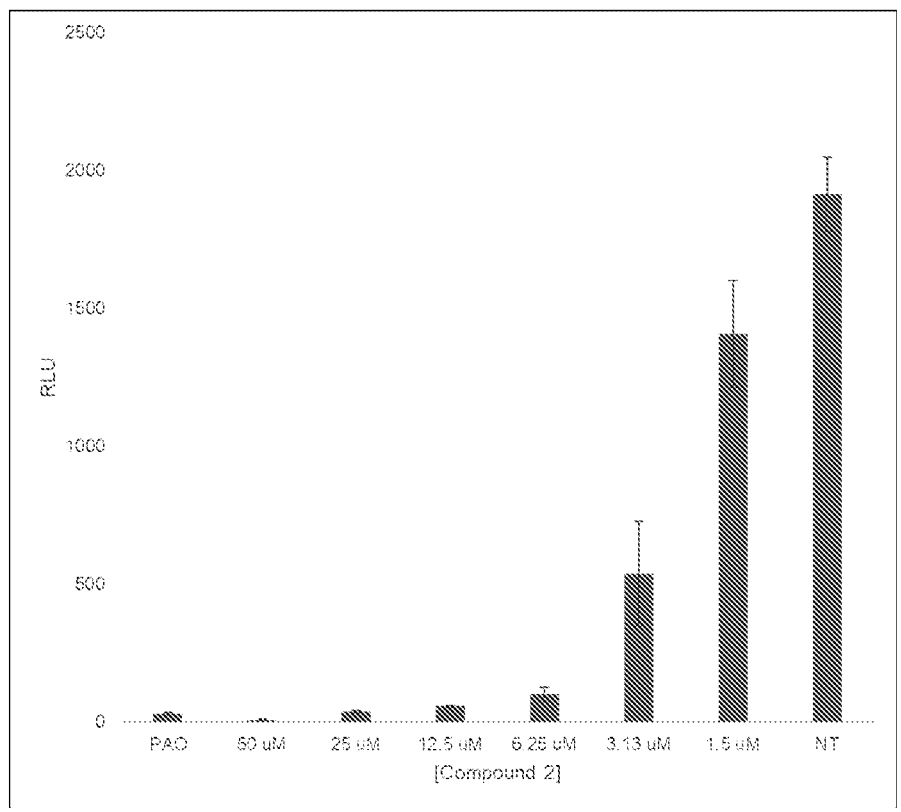
FIG. 3 shows that the MIC of Compound 2 was about 6 μM. An increase in relative light units (RLU) indicates the presence of ATP and viable cells. Phenylarsine oxide (PAO) was used as a control.

Example 4: Minimum Inhibitory Concentration (MIC) of Compound 2 Against *T. cruzi* Epimastigotes A 1:20 working dilution of *T. cruzi* epimastigotes was prepared in LIT1029 medium from a saturated (~4×10$^6$ cells/mL) culture. 100 μL of the 1:20 working dilution was plated, and the epimastigotes were incubated with 50 μM, 25 μM, 12.5 μM, 6.25 μM, 3.13 μM, 1.5 μM, or 0 μM Compound 2 for 48 hours at 30° C. After incubation with Compound 2, *T. cruzi* viability was assessed via an ATP assay. FIG. 3 shows that the MIC of Compound 2 was about 6 μM. An increase in relative light units (RLU) indicates the presence of ATP and viable cells. Phenylarsine oxide (PAO) was used as a control.

Example 5: Determining the MICs of Compounds of the Disclosure Against *T. cruzi* Amastigotes and Trypomastigotes The MICs of compounds of the disclosure against a mixture of *T. cruzi* amastigotes and trypomastigotes were determined. Adult retinal pigment epithelial (ARPE) cells were infected with epimastigotes expressing the red fluorescent protein tdTomato for about 10 days. The infection resulted in release of amastigotes and trypomastigotes into cell media.

Figure 4:
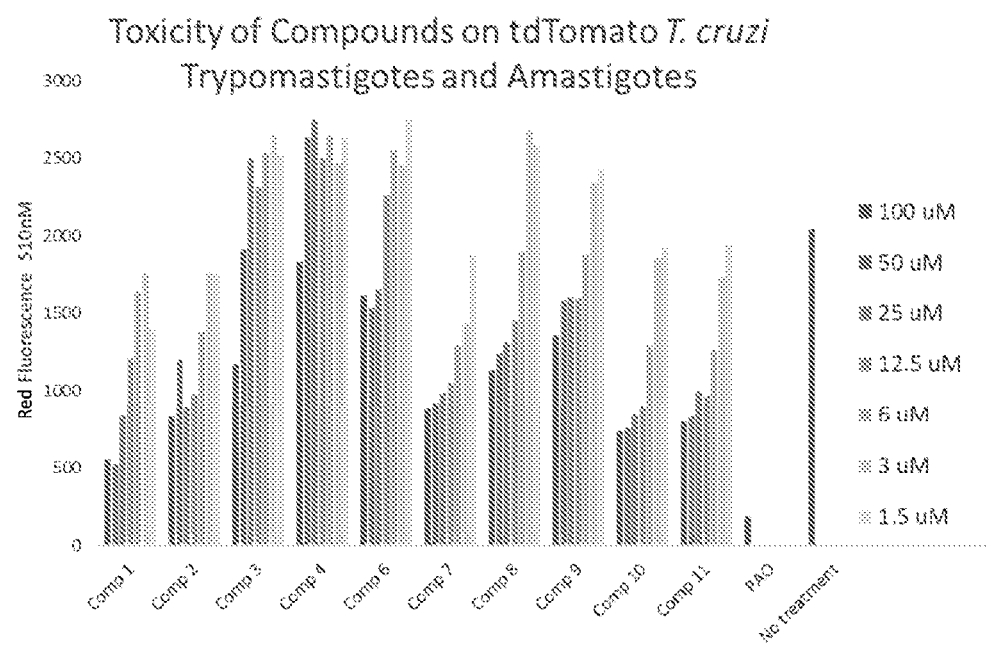
FIG. 4 shows Red fluorescence (510 nm) readings of human ARPEs infected and propagated with *T. cruzi* before treatment with compounds of the disclosure.

The mixture of amastigotes and trypomastigotes was plated at ~2×10$^4$ parasites/100 μL in 96-well plates. Wells were incubated with 100 μM, 50 μM, 25 μM, 12.5 μM, 6 μM, 3 μM, 1.5 μM, or 0 μM of a compound for 48 hours at 37° C. After the incubation period, the viability of amastigotes and trypomastigotes was assessed by measuring the fluorescence intensity at 510-590 nm using a Tecan plate reader, where the presence of fluorescence indicative of viable amastigotes/trypomastigotes. FIG. 4 shows Red fluorescence (510 nm) readings of human ARPEs infected and propagated with *T. cruzi* before treatment with compounds of the disclosure.

Figure 5:
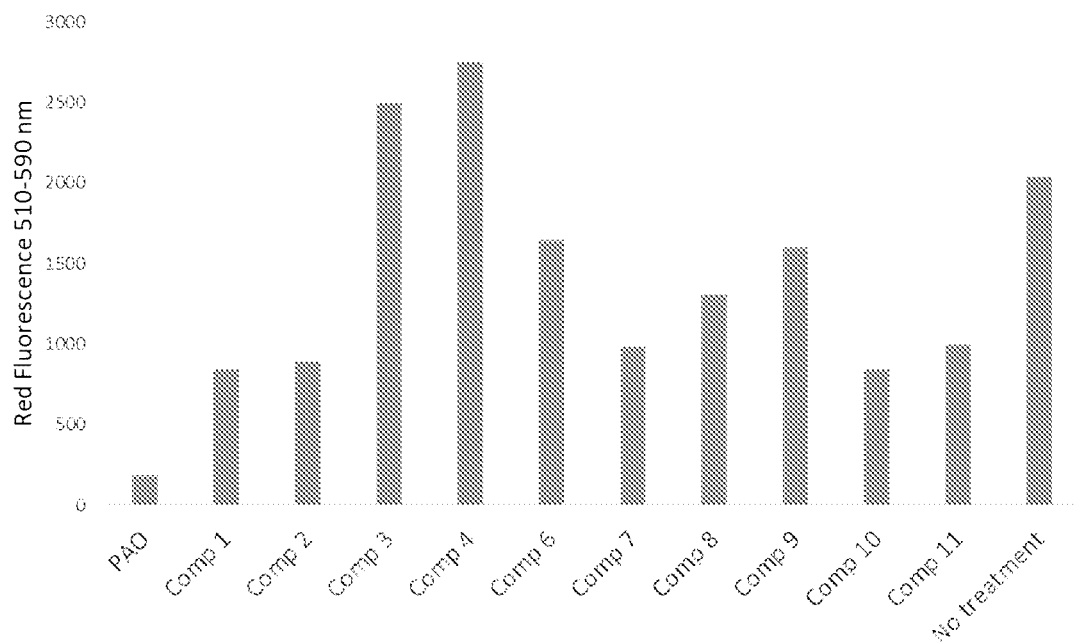
FIG. 5 shows the toxicity of the compounds of the disclosure at 2 μM on tdTomato *T. cruzi* trypomastigotes and amastigotes.

Example 6: Toxicity of Compounds of the Disclosure Towards *T. cruzi* Amastigotes and Trypomastigotes at 25 μM The viability of a mixture of *T. cruzi* amastigotes and trypomastigotes after exposure to 25 μM of the compounds of the disclosure was determined. 2×10$^5$ parasites/100 μL were plated in 96-well plates. Parasites expressing tdTomato were used to assess parasite viability using fluorescence measurements. Parasites were incubated with 25 μM of the compounds of the disclosure for 48 hours at 37° C. After the incubation period, the viability of amastigotes and trypomastigotes was assessed by measuring the fluorescence intensity at 510 nm-590 nm using a Tecan plate reader, where the presence of fluorescence indicated viable amastigotes/trypomastigotes. FIG. 5 shows the toxicity of the compounds of the disclosure at 25 μM on tdTomato *T. cruzi* trypomastigotes and amastigotes. The data show that Compound 1, Compound 2, Compound 7, Compound 10, and Compound 56 were the most toxic to *T. cruzi* amastigotes and trypomastigotes at 25 μM.

Example 7: Effect of Compound 2 on Jurkat, U87, HeLa and ARPE Cell Survival

Figure 6:
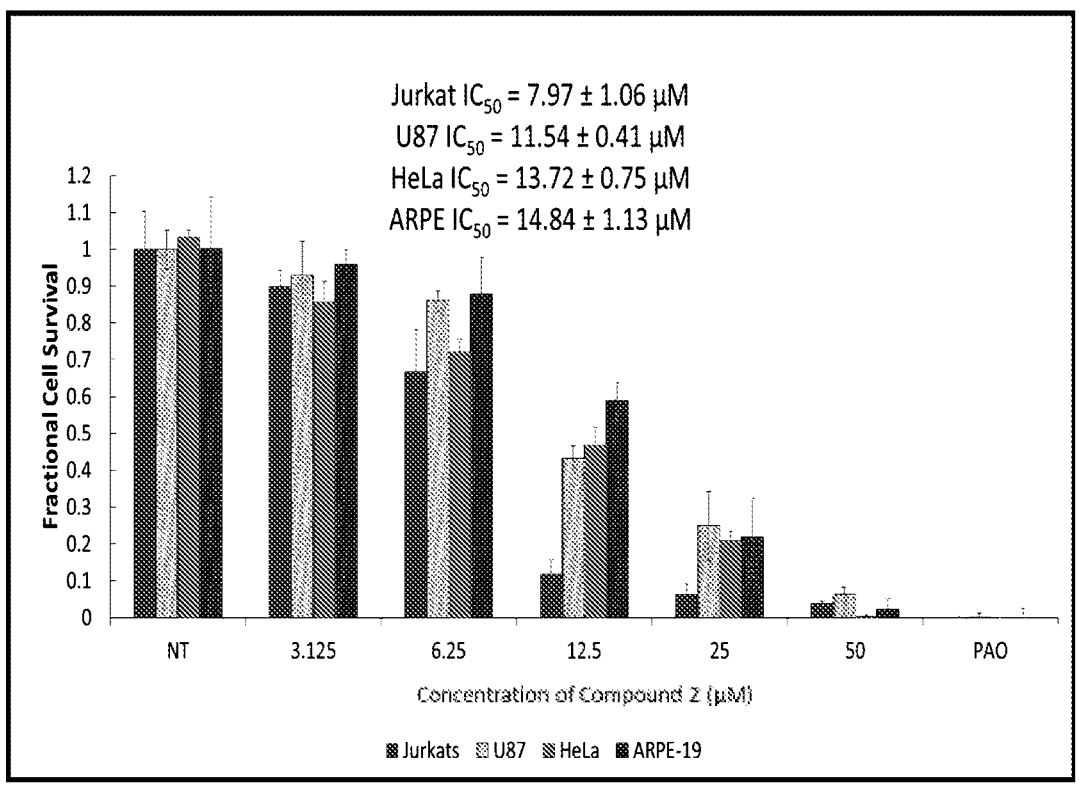
FIG. 6 shows that Compound 2 treatment affected cell survival of Jurkat, U87, HeLa and ARPE cells in a dose-dependent manner.

The GI$_{50}$ (IC$_{50}$), the concentration at which 50% cell survival is seen upon treatment with a compound, was determined for Compound 2 in Jurkat, U87, HeLa, and ARPE cells. Cells were cultured in 96-well plates and incubated with 50 μM, 25 μM, 12.5 μM, 6 μM, 3 μM, 1.5 μM, or 0 μM of Compound 2 for 48 hours at 37° C. Following the incubation period, a 3-(4,5-dimethylthiazol-2-yl)-2,5-diphenyl tetrazolium bromide (MTT) assay was performed. In brief, a 10% volume of MTT was added to each well. Cells were incubated with MTT for 2 hours, at which time cell supernatant was removed and cells were taken into 100 μL DMSO. The absorbance of cell solutions was then read at 595 nm. A decrease in absorbance indicated a decrease in cell survival. FIG. 6 shows that Compound 2 treatment affected cell survival of Jurkat, U87, HeLa and ARPE cells in a dose-dependent manner. The data show that Compound 2 resulted in an IC$_{50}$ value of 7.97±1.06 μM for Jurkat cells; IC$_{50}$ value of 11.54±0.41 μM for U87 cells; IC$_{50}$ value of 13.72±0.75 μM for HeLa cells; and IC$_{50}$ value of 14.84±1.13 μM for ARPE cells.

Example 8: Compound 2 Treatment of *T. cruzi*-Infected ARPE Cells

Four confocal dishes were prepared with 10,000 ARPE cells, which were adhered overnight at 37° C. The four dishes were ARPE control cells, non-infected but 5 μM Compound 2-treated cells, non-treated but infected cells, and infected cells treated with 5 μM Compound 2. For the infected dishes, ARPE media was removed and replaced with 2 mL of infectious amastigotes and trypomastigotes from the ARPE passaged plate. The dishes were then incubated for 2 hours at 37° C. The treated dishes were incubated with 5 μM Compound 2 for 5 days at 37° C., while untreated dishes were incubated in fresh media without Compound 2 for 5 days at 37° C. After the 5-day period, cells were washed 3 times in ARPE media and fixed with 1 mL 4% paraformaldehyde. Cells were visualized using an EVOS cell imaging system. Amastigotes appeared as small, dense, and mostly birefringent in images. The data show that amastigotes were absent in ARPE cultures treated with Compound 2 and present in non-treated cultures.

Figure 7:
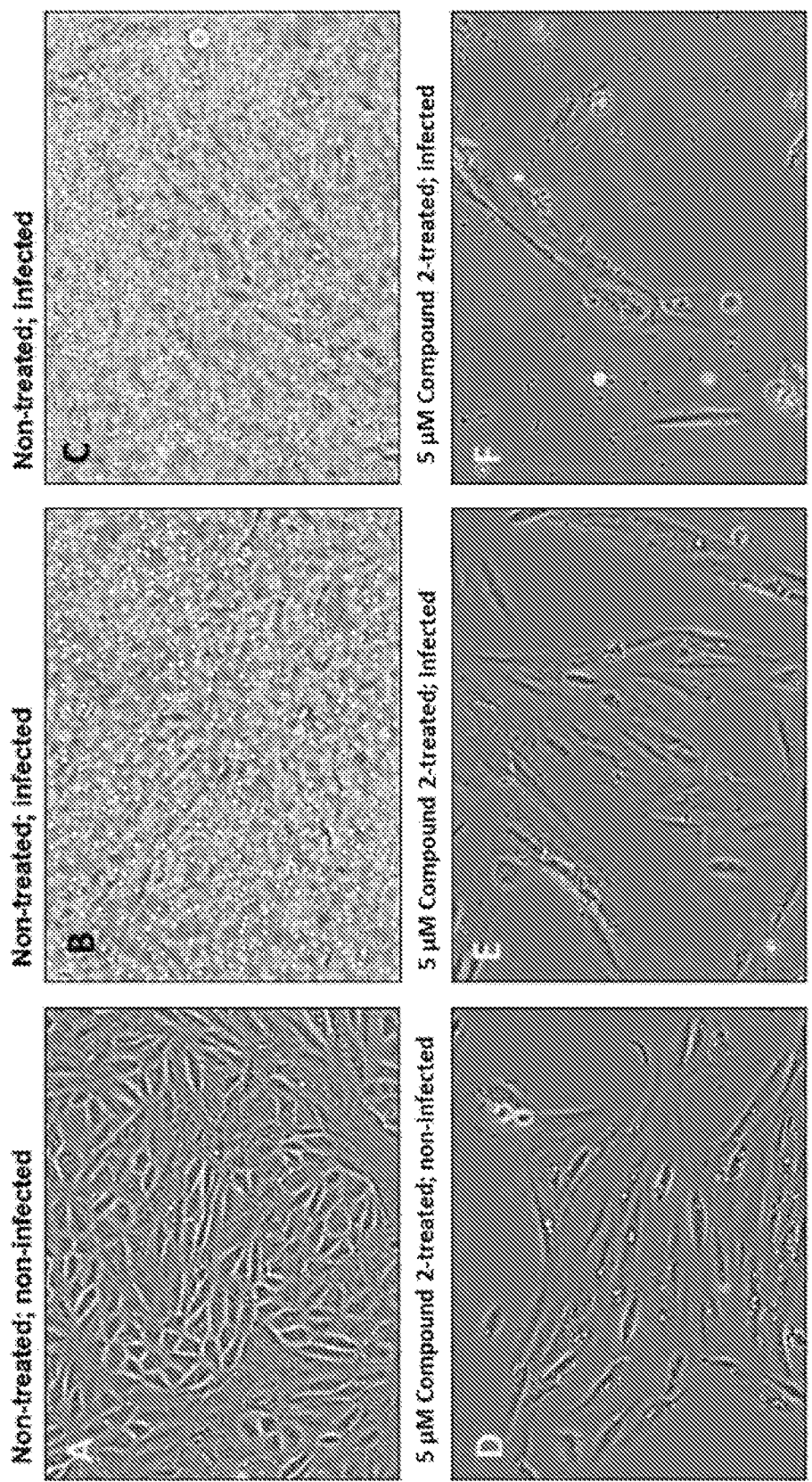
FIG. 7 PANEL A shows an image of non-treated and non-infected ARPE cells.

FIG. 7 PANEL A shows an image of non-treated and non-infected ARPE cells. FIG. 7 PANEL B and PANEL C show images of *T. cruzi*-infected ARPE cells that did not receive treatment with Compound 2. FIG. 7 PANEL D shows an image of non-infected ARPE cells treated with 5 μM Compound 2. FIG. 7 PANEL E and PANEL F show images of *T. cruzi*-infected ARPE cells treated with 5 μM Compound 2.

Figure 8:
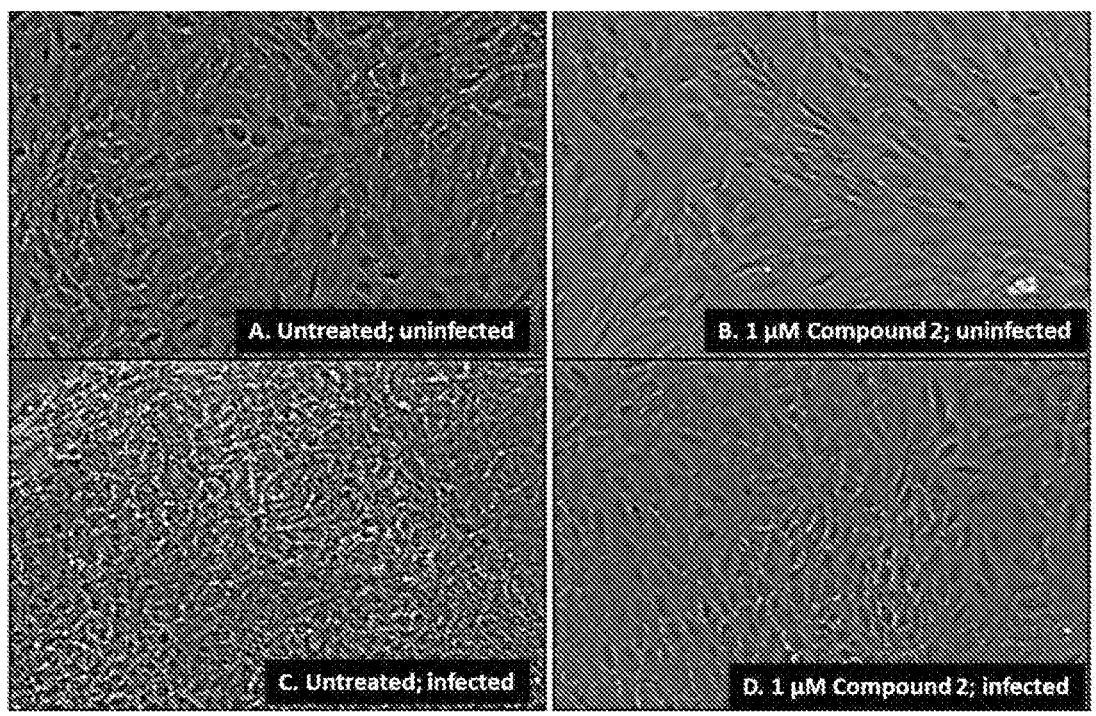
FIG. 8 PANEL A shows an image of uninfected ARPE cells that were not treated with Compound 2.

The experiment above was repeated using 1 μM Compound 2. The data show that amastigotes were absent in ARPE cultures treated with Compound 2 and present in non-treated cultures. FIG. 8 PANEL A shows an image of uninfected ARPE cells that were not treated with Compound 2. FIG. 8 PANEL B shows an image of uninfected ARPE cells treated with 1 μN4 Compound 2. FIG. 8 PANEL C shows an image of *T. cruzi*-infected ARPE cells that did not receive treatment with Compound 2. FIG. 8 PANEL D shows an image of *T. cruzi*-infected ARPE cells treated with 1 μM Compound 2.

Figure 9:
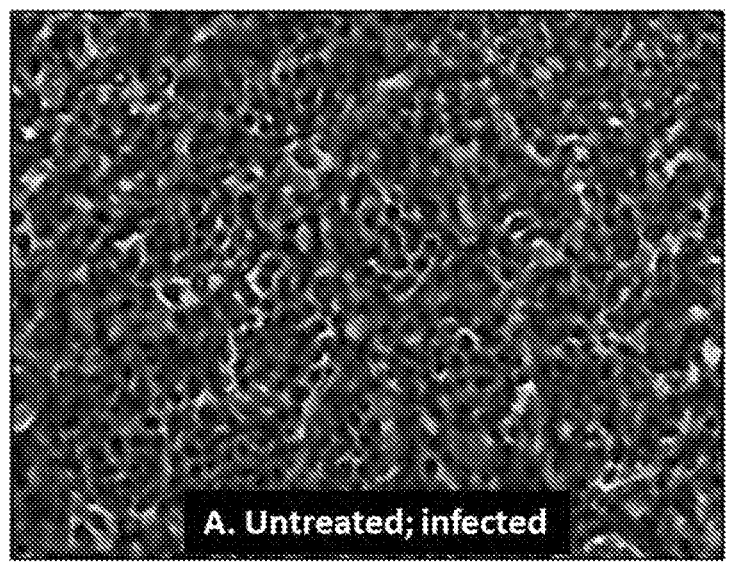
FIG. 9 PANEL A shows an image of *T. cruzi*-infected ARPE cells that were not treated with Compound 2. The image shows small, round dots, which are individual parasites.
Figure 9:
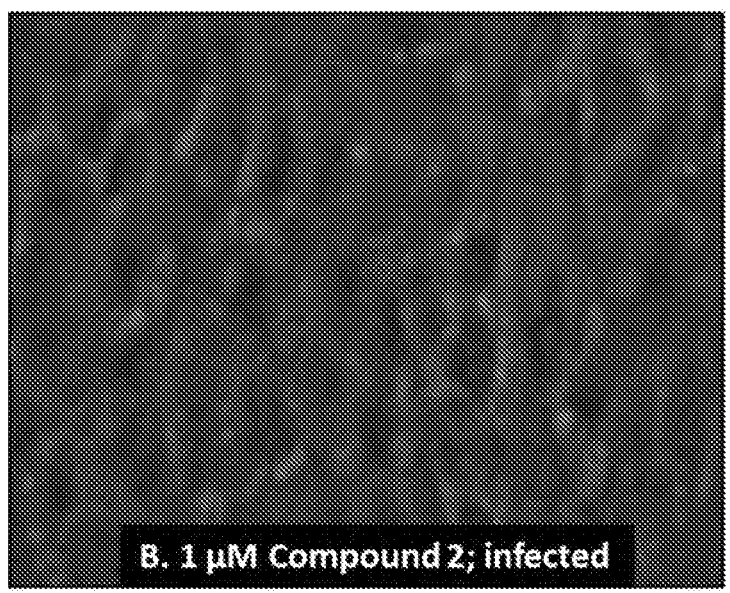

FIG. 9 PANEL A shows an image of *T. cruzi*-infected ARPE cells that were not treated with Compound 2. The image shows small, round dots, which are individual parasites. FIG. 9 PANEL B shows an image of *T. cruzi*-infected ARPE cells that were treated with 1 μN4 Compound 2.

Example 9: Viability of *T. cruzi* and ARPE Cells Following a 7-Day Incubation with Compound 2

Four confocal dishes with 10,000 ARPE cells were prepared and adhered overnight at 37° C. The four dishes were:

1) ARPE control cells; 2) non-infected cells treated with 1 µM Compound 2; 3) untreated infected cells; and 4) *T. cruzi*-infected cells treated with 1 µM Compound 2. For the infected dishes, ARPE media was removed and replaced with 2 mL of infectious amastigotes and trypomastigotes expressing tdTomato (from ARPE passaged plate). The dishes were then incubated overnight for 7 days at 37° C. The untreated dishes were incubated in fresh media without Compound 2 for 7 days at 37° C. After the 7-day incubation period, cells were washed 3 times in ARPE media and fixed with 1 mL 4% paraformaldehyde. tdTomato fluorescence, which is indicative of viable *T. cruzi*, was then observed via fluorescence microscopy.

Figure 10:
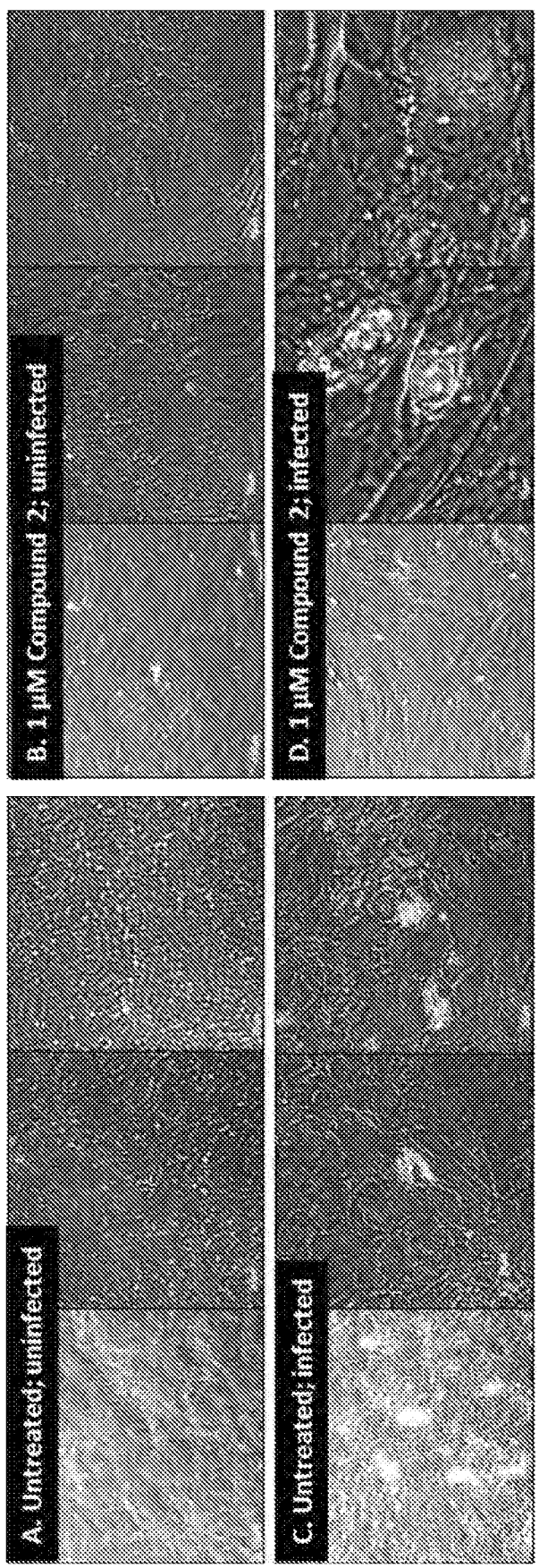
FIG. 10 PANEL A shows images of ARPE control cells that were uninfected and untreated with Compound 2.

FIG. 10 PANEL A shows images of ARPE control cells that were uninfected and untreated with Compound 2. FIG. 10 PANEL B shows images of uninfected ARPE cells treated with 1 µM Compound 2. FIG. 10 PANEL C shows images of *T. cruzi*-infected ARPE cells that were not treated with Compound 2. FIG. 10 PANEL D shows images of *T. cruzi*-infected ARPE cells treated with 1 µM Compound 2.

Figure 11:
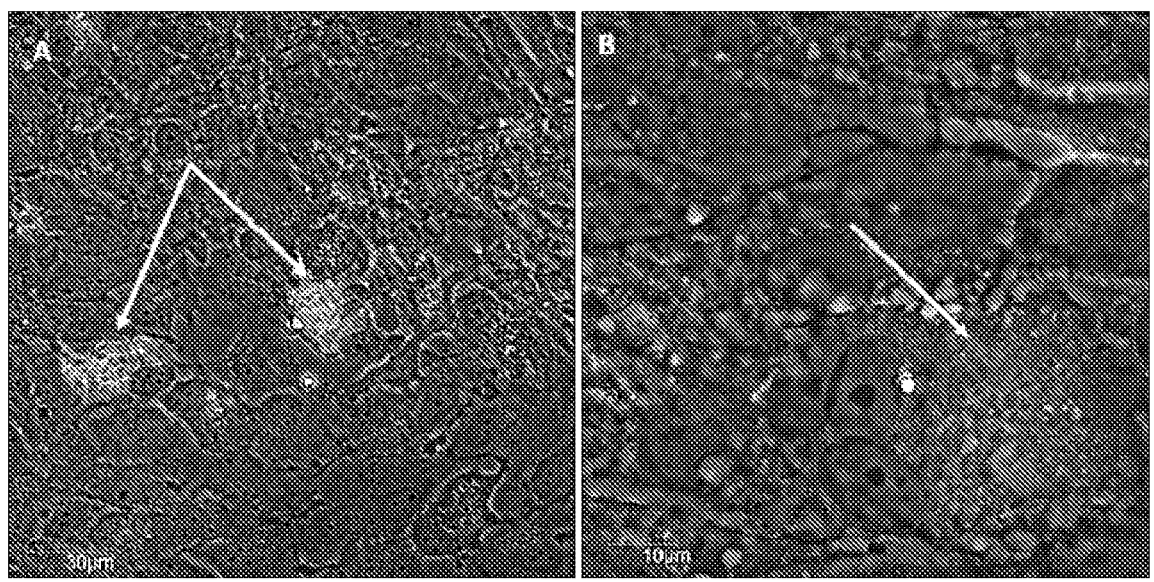
FIG. 11 PANEL A shows an image of *T. cruzi*-infected ARPE cells that were not treated with Compound 2. The arrows show intact, round amastigote *T. cruzi*-infected ARPE cells FIG. 11 PANEL B shows an image of *T. cruzi*-infected ARPE cells that were treated with 1 μM Compound 2. The arrow shows a dead *T. cruzi* parasite disintegrating after treatment with Compound 2.

FIG. 11 PANEL A shows an image of *T. cruzi*-infected ARPE cells that were not treated with Compound 2. The arrows show intact, round amastigote *T. cruzi*-infected ARPE cells FIG. 11 PANEL B shows an image of *T. cruzi*-infected ARPE cells that were treated with 1 µM Compound 2. The arrow shows a dead *T. cruzi* parasite disintegrating after treatment with Compound 2. The data show that intracellular *T. cruzi* parasites were eradicated by treatment with 1 µM Compound 2. Moreover, the images show that ARPE cells were not visibly harmed by 1 µM Compound 2 treatment.

Example 10: Repeated Treatment of *T. cruzi*-Infected Cells with Compound 2

ARPE cells were plated in confocal dishes (20,000 cells per dish) and incubated overnight at 37° C. Cells were infected with *T. cruzi* by incubating cells with *T. cruzi* amastigotes and trypomastigotes expressing tdTomato (~2× 10⁵ cells in total) for 24 hours at 37° C. Uninfected cells served as controls. Following the *T. cruzi* incubation period, extracellular parasites were removed, and the medium was replaced with DMEM/F12 culture media with or without 1 µM Compound 2. The cells were incubated further for 24 hours at 37° C. Cells were then treated two more times with fresh DMEM/F12 culture media with or without 1 µM Compound 2 and incubated for 24 hours at 37° C. Following fixation of cells in 4% paraformaldehyde, plates were imaged for tdTomato fluorescence, which is indicative of viable *T. cruzi*, such that the effects of repeated Compound 2 treatment could be compared to a single treatment with Compound 2. The data show that a single treatment with 1 µM Compound 2 resulted in only a small portion of the *T. cruzi* infection remaining in the cells, while repeated treatment eradicated the *T. cruzi* infection. Moreover, single or repeated treatment with 1 µM did not impact the morphology or overall health of the ARPE host cells.

Figure 12:
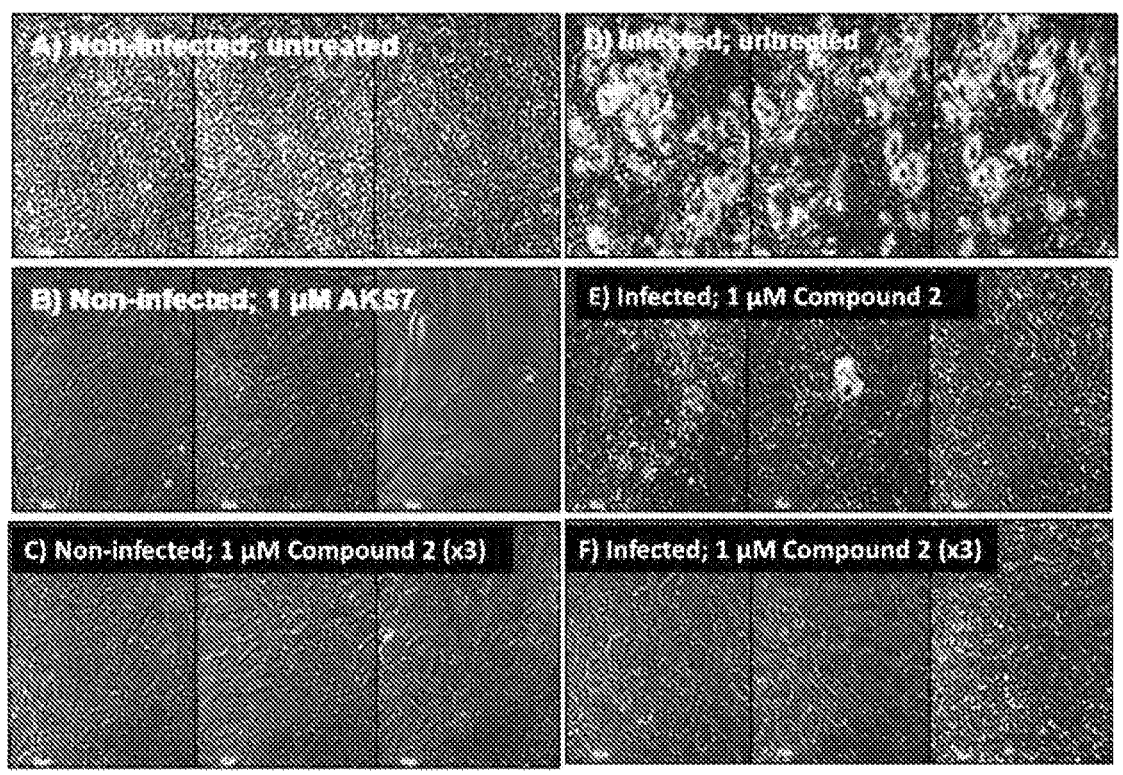
FIG. 12 PANEL A shows images of uninfected ARPE cells that did not receive treatment with Compound 2.

FIG. 12 PANEL A shows images of uninfected ARPE cells that did not receive treatment with Compound 2. FIG. 12 PANEL B shows images of uninfected ARPE cells treated with a single treatment of 1 µM Compound 2. FIG. 12 PANEL C shows images of uninfected ARPE cells treated three times with 1 µM Compound 2. FIG. 12 PANEL D shows images of *T. cruzi*-infected ARPE cells that were not treated with Compound 2. FIG. 12 PANEL E shows images of *T. cruzi*-infected ARPE cells that received a single treatment of 1 µM Compound 2. FIG. 12 PANEL F shows images of *T. cruzi*-infected ARPE cells after three treatments with 1 µM Compound 2.

Example 11: A Single Treatment with Low Micromolar Compound 2 Selectively Kills *T. cruzi*

ARPE cells were plated in confocal dishes (20,000 cells per dish) and incubated overnight at 37° C. Cells were infected with *T. cruzi* by incubating cells with *T. cruzi* amastigotes and trypomastigotes expressing tdTomato (~2× 10⁵ cells in total) for 24 hours at 37° C. before washing dishes three times with DMEM/F12 culture media. Uninfected plates served as controls. The dishes were then treated with 2 µM Compound 2 or left untreated as a control and incubated further for 5 days at 37° C. The treated dish received a single treatment of Compound 2 on day 1. Dishes were washed twice with DMEM/F12 media and fixed in 4% paraformaldehyde before being imaged using confocal microscopy. The data show that one treatment with 2 µM Compound 2 resulted in full parasite death, and no subsequent infection was observed within the 5-day incubation period post-treatment. The other Compound 2 dishes that were not incubated with *T. cruzi* a second time were used as controls. Following fixation of cells in 4% paraformaldehyde, tdTomato fluorescence of the cells was assessed using confocal microscopy. The data show that 2 µM Compound 2 eradicated intracellular *T. cruzi* and protected cells from reinfection.

Figure 13:
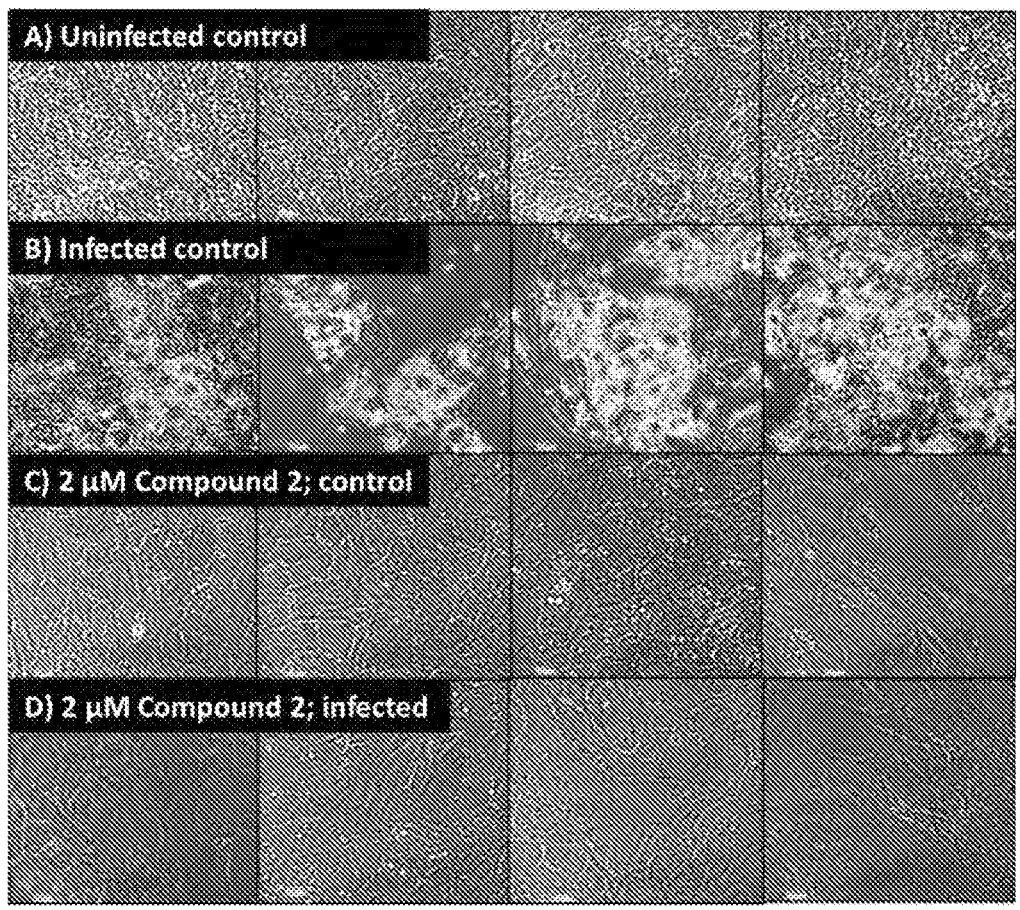
FIG. 13 ROW A shows images of uninfected ARPE cells that were used as a control.

FIG. 13 ROW A shows images of uninfected ARPE cells that were used as a control. FIG. 13 ROW B shows images of *T. cruzi*-infected ARPE cells that were used as a control. FIG. 13 ROW C shows images of uninfected ARPE cells treated with 2 µM Compound 2. FIG. 13 ROW D shows images of *T. cruzi*-infected ARPE cells treated with 2 µM Compound 2.

Example 12: Treatment of *T. cruzi*-Infected ARPE Cells with 5 µM Compound 2

ARPE cells were plated in confocal dishes (20,000 cells per dish) and incubated overnight at 37° C. Dishes were incubated with *T. cruzi* amastigotes and trypomastigotes expressing tdTomato (~2×10⁵ cells) for 48 hours at 37° C. Untreated cells served as controls. Cells were then washed 3 times with cell medium, treated with 5 µM Compound 2 or left untreated as a control and incubated further for 2 days at 37° C. The cells were then fixed in 4% paraformaldehyde, and tdTomato fluorescence of the cells was assessed using confocal microscopy. The results show that treatment with Compound 2 killed intracellular parasites, and that the parasites were eliminated by the host cell after 2 days of treatment. Many *T. cruzi* trypomastigotes and amastigotes remained visible intracellularly after 2 days, but most were crumpled and dead.

Figure 14:
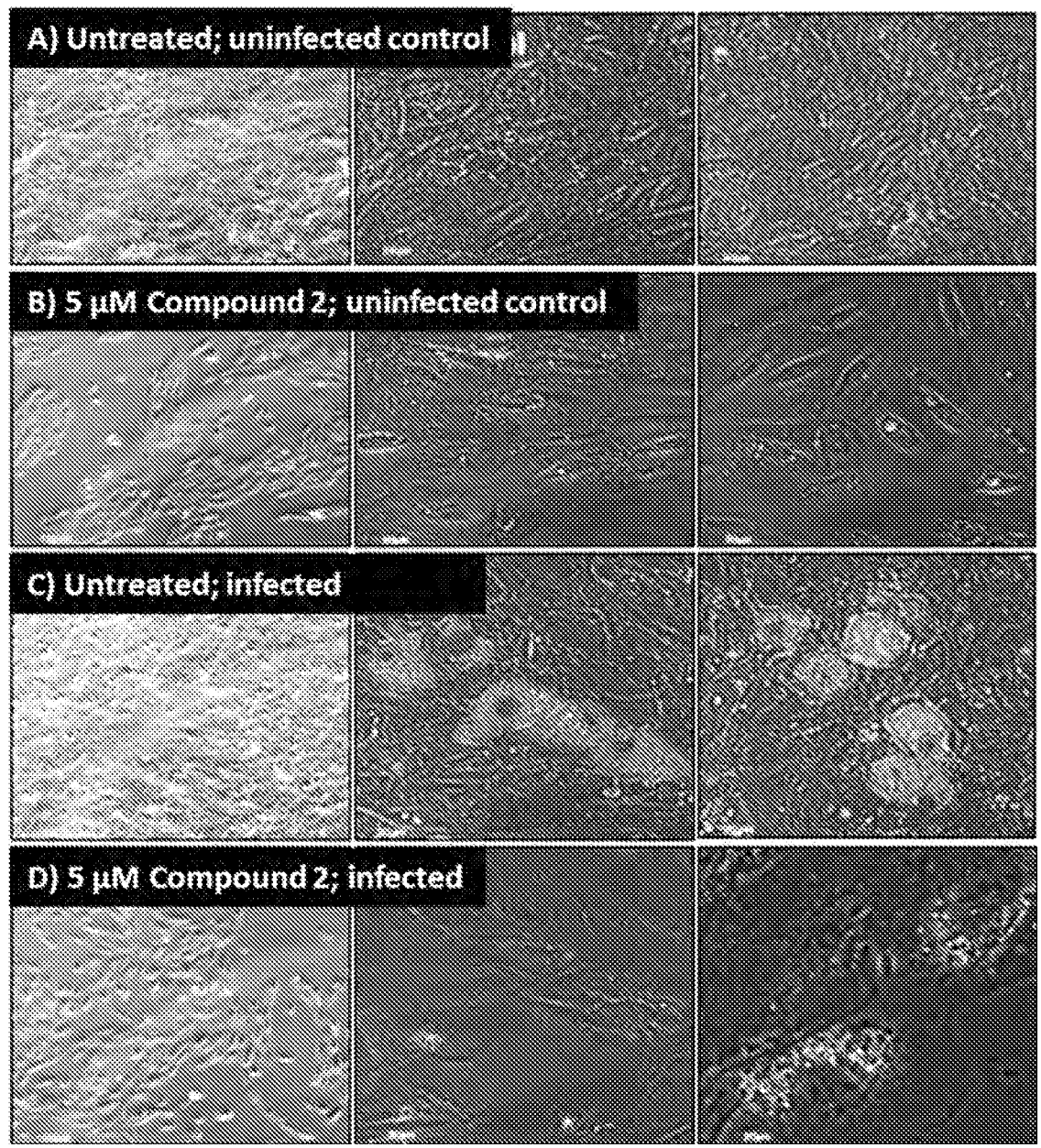
FIG. 14 ROW A shows images of uninfected ARPE cells that were not treated with Compound 2.
Figure 15:
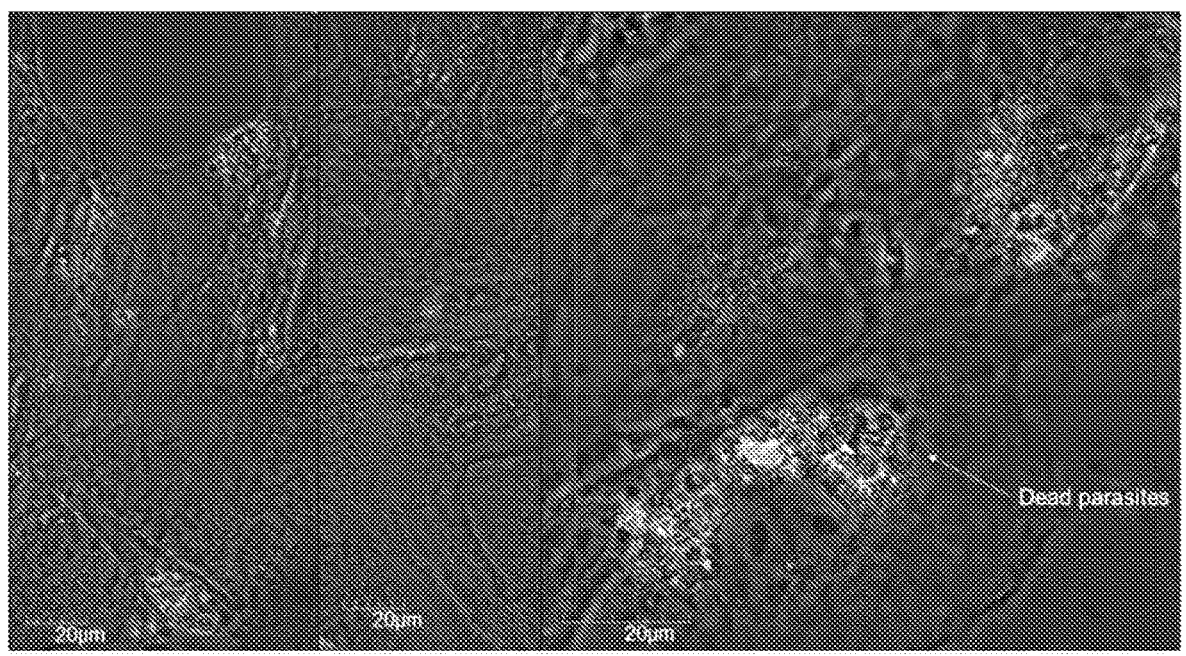
FIG. 15 shows images of dead *T. cruzi* trypomastigotes and amastigotes after treatment with 5 μM Compound 2.

FIG. 14 ROW A shows images of uninfected ARPE cells that were not treated with Compound 2. FIG. 14 ROW B shows images of uninfected cells treated with 5 µM Compound 2. FIG. 14 ROW C shows images of *T. cruzi*-infected cells that were not treated with Compound 2. FIG. 14 ROW D shows images of *T. cruzi*-infected cells that were treated with 5 µM Compound 2. FIG. 15 shows images of dead *T. cruzi* trypomastigotes and amastigotes after treatment with 5 µM Compound 2.

Example 13: Long Term Cure of ARPE Infected Cells Via Treatment with 10 µM Compound 2

About 20,000 ARPE cells were incubated with *T. cruzi* amastigotes and tryomastigotes 200,000 cells) expressing tdTomato for 24 hours to initiate an infection. Uninfected cells served as controls. Cells were washed three times with DMEM/F12 with 10% fetal bovine serum, and treated with 10 µM Compound 2, 5 µM Compound 2, or left untreated. Plates were incubated further for 2 days at 37° C. before the cells were trypsinized and split into a fresh 24-well plate. The cells were then incubated for an additional 10 days at 37° C. before being trypsinized again and split into confocal dishes for visualization 5 days later. Cells were visualized with an EVOS cell imaging system. *T. cruzi* appeared as tiny, highly refractive dots at day 12. Additionally, tdTomato fluorescence levels in cells was assessed via fluorescence imaging on day 17 using confocal microscopy.

Figure 16:
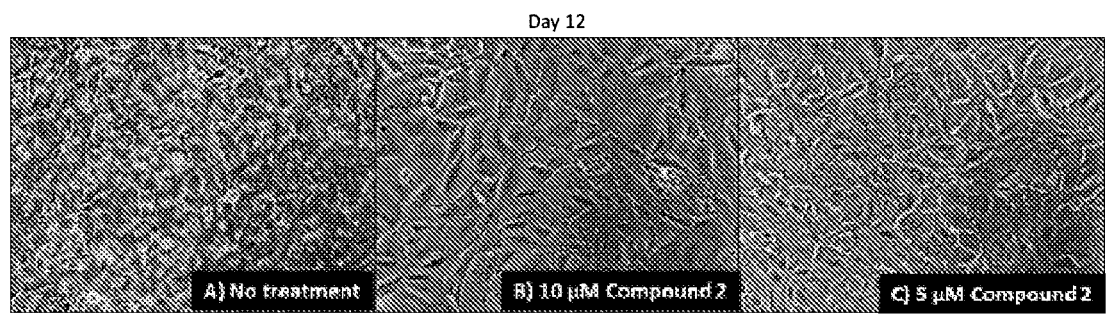
FIG. 16 PANEL A shows an image of cells that were infected with *T. cruzi* but were not treated.

FIG. 16 PANEL A shows an image of cells that were infected with *T. cruzi* but were not treated. The image shows tiny, highly refractive *T. cruzi* dots. FIG. 16 PANEL B shows an image of infected cells treated with 10 µM Compound 2. *T. cruzi* could not be seen in the infected and 10 µM Compound 2-treated cells. FIG. 16 PANEL C shows an image of infected cells treated with 5 µM of Compound 2. Small amounts of *T. cruzi* dots were observed in the pre-infected and 5 µM Compound 2-treated ARPE cells. The images did not suggest any negative effects of Compound 2 treatment on cell health. The EVOS imaging results were consistent with what was seen in fluorescence images, as no tdTomato fluorescence was observed in 10 Compound 2-treated cells. Only two *T. cruzi*-infected cell foci were found in the images of 5 Compound 2-treated cells.

Figure 17:
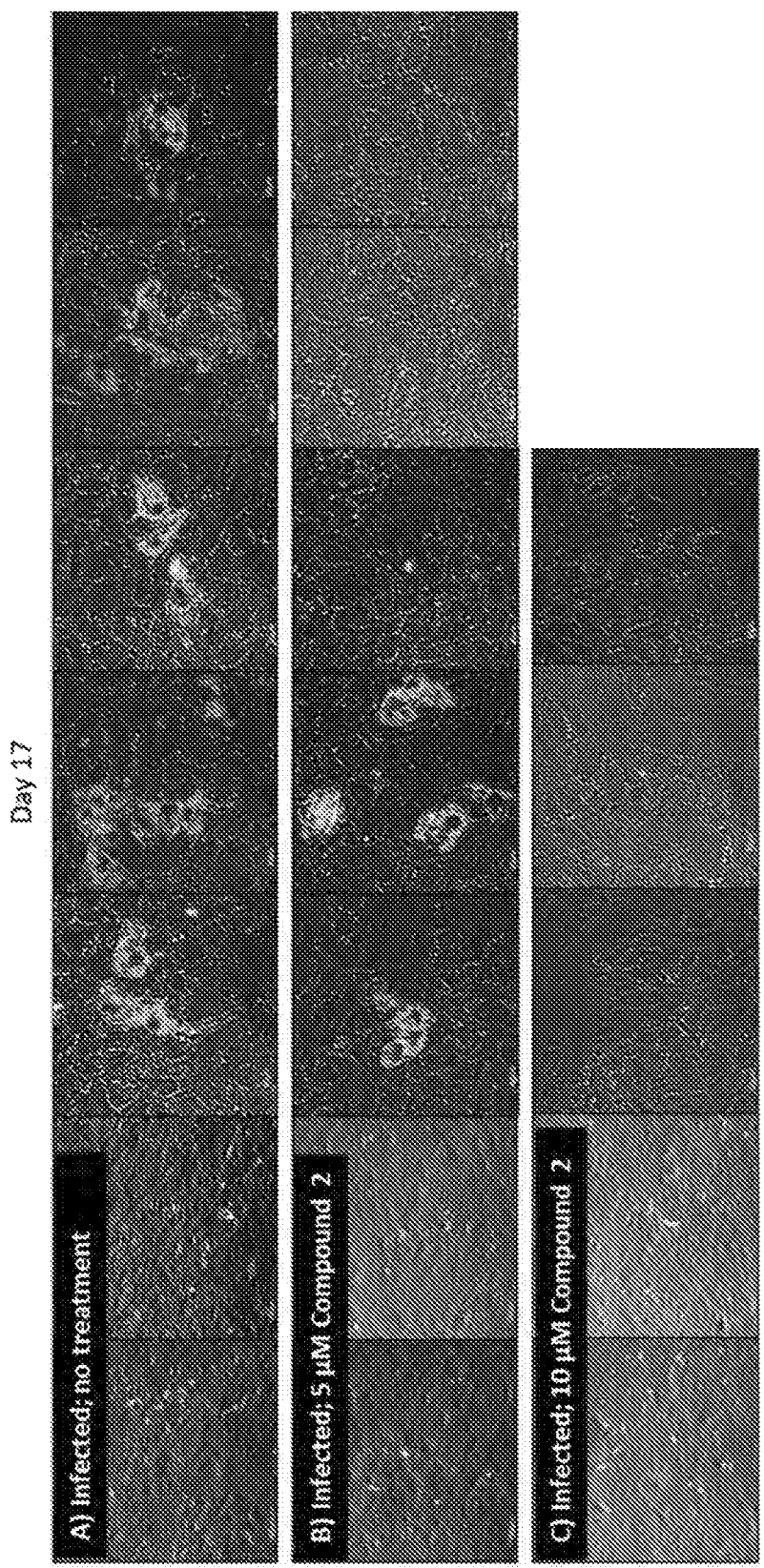
FIG. 17 ROW A shows images of *T. cruzi*-infected ARPE cells that did not receive any treatment.

FIG. 17 ROW A shows images of *T. cruzi*-infected ARPE cells that did not receive any treatment. FIG. 17 ROW B shows images of *T. cruzi*-infected ARPE cells that received treatment with 5 µM Compound 2. FIG. 17 ROW C shows images of *T. cruzi*-infected ARPE cells that received treatment with 10 µM Compound 2.

Example 14: Long Term Cure of ARPE Infected Cells Via Repeat Treatment with 2 Compound 2

ARPE cells were plated in confocal dishes (20,000 cells per dish) and incubated overnight at 37° C. Dishes were incubated with *T. cruzi* amastigotes and trypomastigotes expressing tdTomato (~2×10$^5$ cells) for 24 hours at 37° C. Uninfected plates served as controls. After *T. cruzi* incubation, parasites were removed, and plates were washed with ARPE medium. Cells were then treated with 2 µM Compound 2 or left untreated as a control and incubated further for 24 hours. Every 24 hours, the treated cells were treated again with 2 µM Compound 2. Treatment continued for a total of 4 days. After 4 days of treatment, one set of dishes was imaged for tdTomato fluorescence to assess the extent of initial *T. cruzi* infection. The remaining sets of dishes were incubated for an additional 5 days without Compound 2 present in the media to determine long term treatment efficacy.

Figure 18:
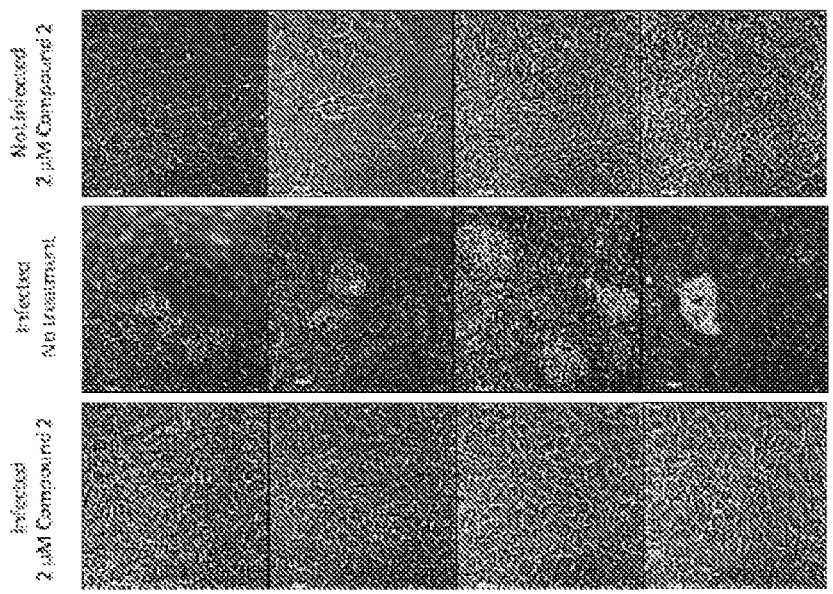
FIG. 18 PANEL A shows images of ARPE cells upon completion of 4 treatments with 2 μM Compound 2 over a period of 4 days.
Figure 18:
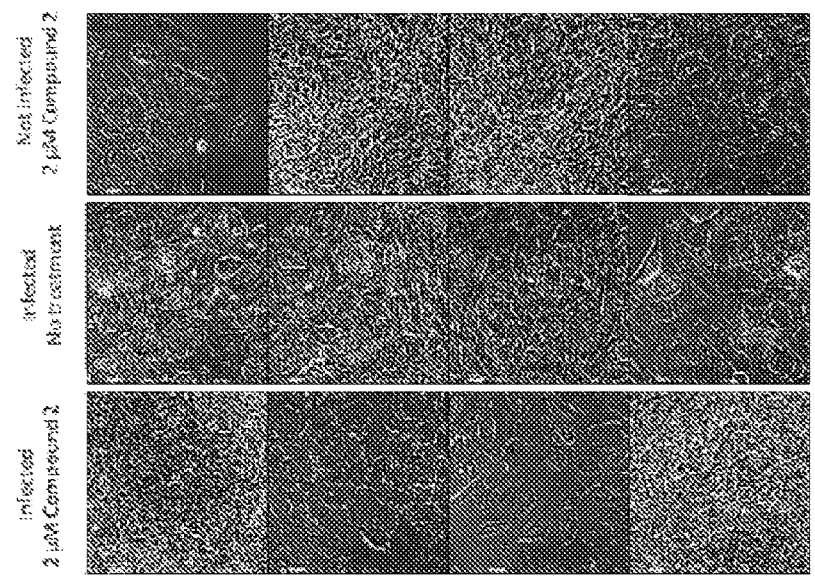

FIG. 18 PANEL A shows images of ARPE cells upon completion of 4 treatments with 2 µM Compound 2 over a period of 4 days. The first row shows images of uninfected ARPE cells treated with 2 µM Compound 2; the second row shows images of *T. cruzi*-infected ARPE cells that were not treated with Compound 2; and the third row shows images of *T. cruzi*-infected ARPE cells that were treated with 2 µM Compound 2. FIG. 18 PANEL B shows images of ARPE cells upon the completion of 4 treatments with 2 µM Compound 2 over a period of 4 days, with 5 additional days of incubation without further treatment. The first row shows images of uninfected ARPE cells treated with 2 µM Compound 2; the second row shows images of *T. cruzi*-infected ARPE cells that were not treated with Compound 2; and the third row shows images of *T. cruzi*-infected ARPE cells treated with 2 µM Compound 2. The white arrows point out the characteristic clusters of spheres within ARPE cells, which are indicative of an intracellular *T. cruzi* infection.

Figure 19:
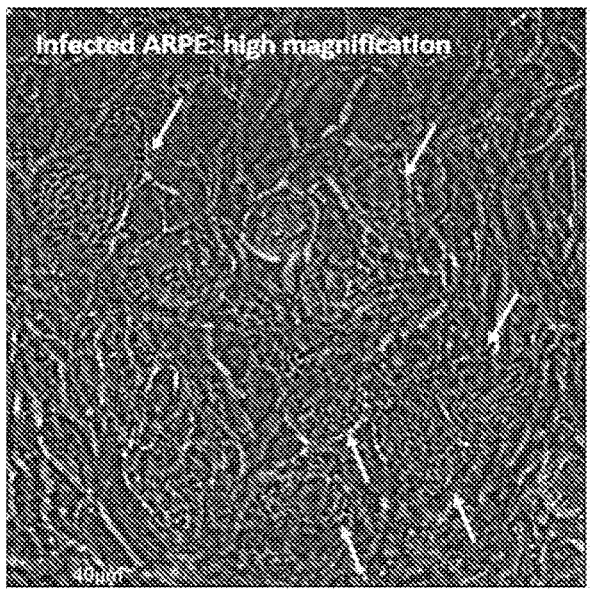
FIG. 19 PANEL A and PANEL B show high-magnification images of *T. cruzi*-infected ARPE cells.
Figure 19:
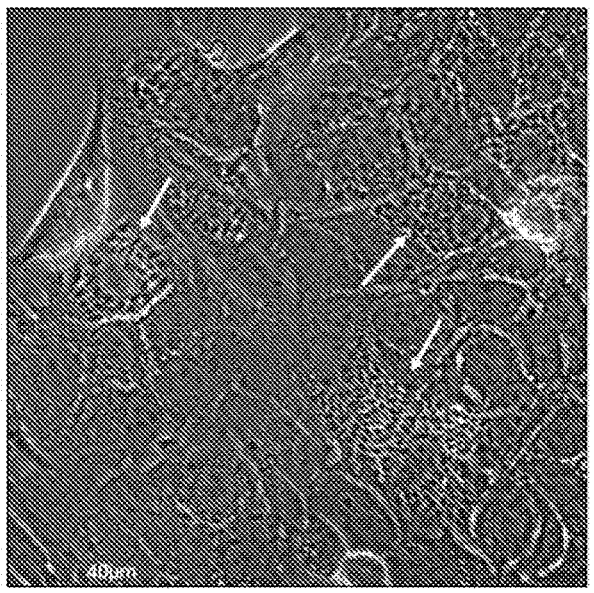
Figure 20:
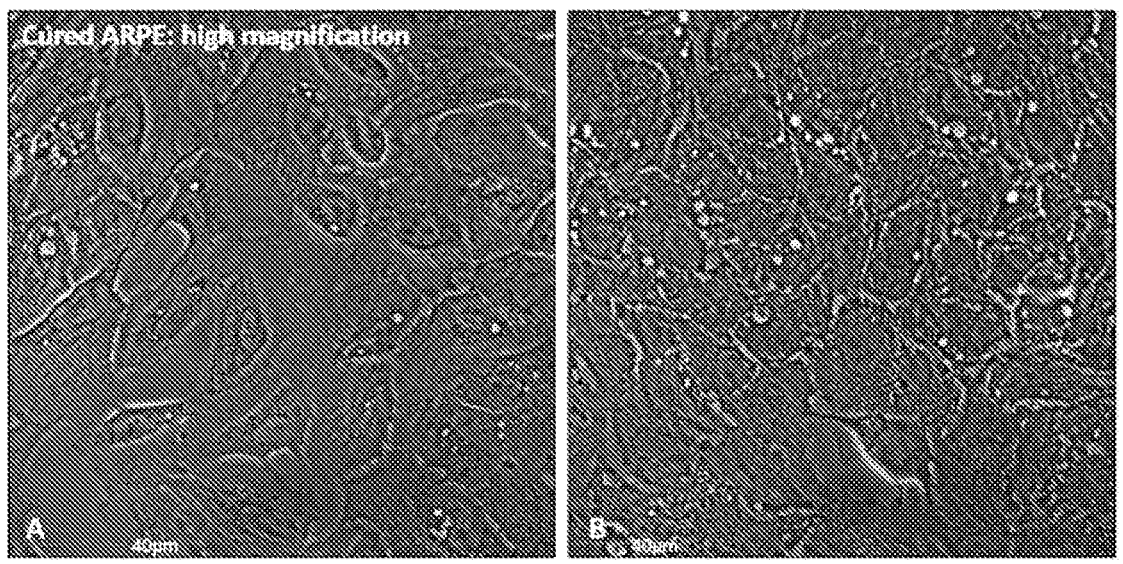
FIG. 20 PANEL A and PANEL B show high-magnification images of cured *T. cruzi*-infected ARPE cells after treatment with Compound 2.

FIG. 19 PANEL A and PANEL B show high-magnification images of *T. cruzi*-infected ARPE cells. The white arrows point out the characteristic clusters of spheres within ARPE-19 cells, which are indicative of an intracellular *T. cruzi* infection. FIG. 20 PANEL A and PANEL B show high-magnification images of cured *T. cruzi*-infected ARPE cells after treatment with Compound 2.

Example 15: 5-Day Treatment with 2 µM of Compound 2

ARPE cells were cultured (20,000 cells per plate) and incubated with *T. cruzi* amastigotes and trypomastigotes expressing tdTomato (~2×10$^5$ cells) for 24 hours at 37° C. Uninfected plates served as controls. Following infection, wells were washed three times with DMEM/F12 (10% FBS) and treated with fresh media containing a vehicle control with or without 2 Compound 2. Every 24 hours for 5 days, media was removed from the wells and replaced with fresh media with or without 2 µM Compound 2. After the final day of treatment, the Compound 2 media was replaced with media without Compound 2, and the plates were incubated for an additional 5 days without any treatment. At the end of the 5-day incubation, tdTomato fluorescence of the cells cells was assessed via fluorescence microscopy. The data show that cells exposed to daily treatment of 2 µM Compound 2 for 5 days were provided with a long-term full cure against a *T. cruzi* infection. No toxicity was observed in the non-infected, treated cells.

Figure 21:
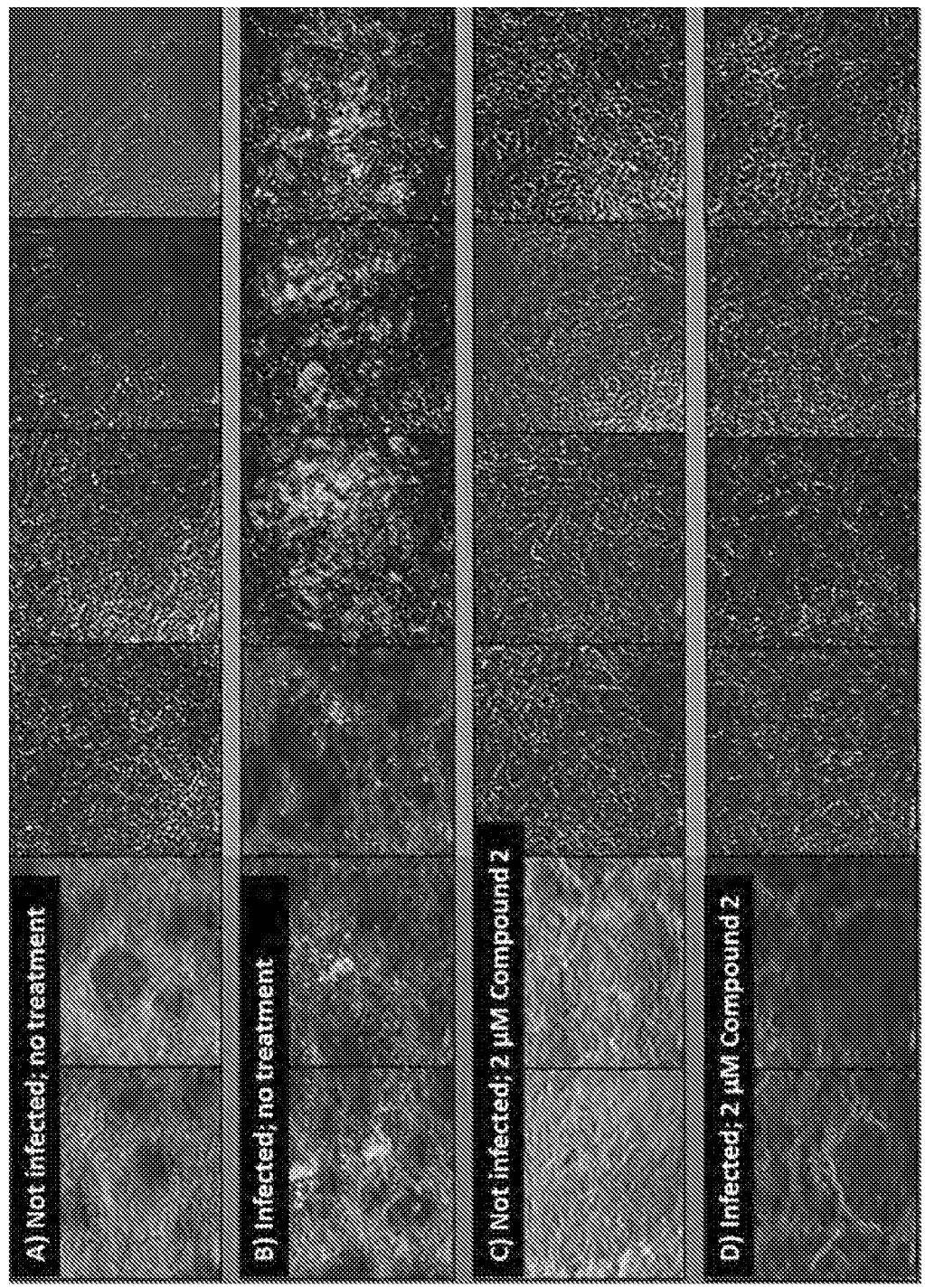
FIG. 21 ROW A shows images of uninfected ARPE cells that did not receive treatment with Compound 2.

FIG. 21 ROW A shows images of uninfected ARPE cells that did not receive treatment with Compound 2. FIG. 21 ROW B shows images of *T. cruzi*-infected ARPE cells that did not receive treatment with Compound 2. FIG. 21 ROW C shows images of uninfected ARPE cells that received treatment with 2 µM Compound 2. FIG. 21 ROW D shows images of *T. cruzi*-infected ARPE cells that were treated with 2 µM Compound 2.

Example 16: Comparing Compound 2 and Compound 7 Treatment of *T. cruzi*-Infected Cells ARPE cells were infected with *T. cruzi* transfected with CherryTomato red fluorescent protein to allow for the visualization of *T. cruzi* within cells. Infected cells and uninfected controls were then treated with vehicle control (1% DMSO), 2 µM Compound 2, or 2 Compound 7 for two days. Following the treatment period, cells were observed under a microscope for CherryTomato fluorescence.

Figure 22:
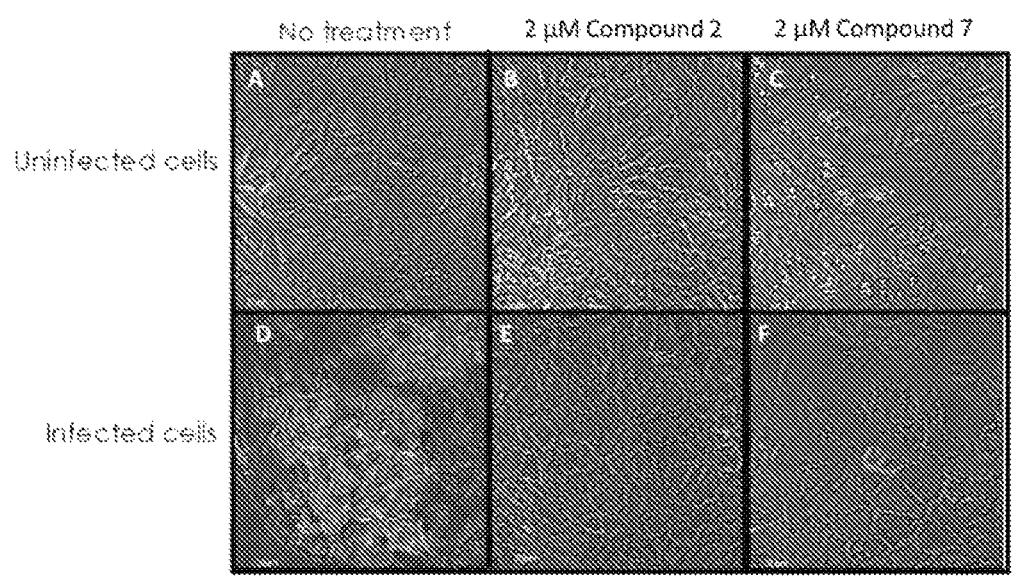
FIG. 22 PANEL A shows an image of uninfected ARPE that did not receive treatment with Compound 2 or Compound 7.

The data show that treatment with Compound 2 or Compound 7 eradicated *T. cruzi*. FIG. 22 PANEL A shows an image of uninfected ARPE that did not receive treatment with Compound 2 or Compound 7. FIG. 22 PANEL B shows an image of uninfected ARPE cells treated with 2 µM Compound 2. FIG. 22 PANEL C shows an image of uninfected ARPE cells treated with 2 µM Compound 7. FIG. 22 PANEL D shows an image of *T. cruzi*-infected ARPE cells that did not receive treatment with Compound 2 or Compound 7. FIG. 22 PANEL E shows an image of *T. cruzi*-infected ARPE cells treated with 2 µM Compound 2. FIG. 22 PANEL F shows an image of *T. cruzi*-infected ARPE cells treated with 2 µM Compound 7.

Example 17: Compound 2 and Compound 7 Selectively Eliminate *T. cruzi*

ARPE cells were plated in confocal dishes (20,000 cells per dish) and incubated overnight at 37° C. Dishes were incubated with *T. cruzi* amastigotes and trypomastigotes expressing tdTomato (~2×10$^5$ cells) for 24 hours at 37° C., before washing off the un-internalized, extracellular parasites three times with DMEM/F12 media. Uninfected dishes served as controls. The dishes were then treated with vehicle control (no treatment), 2 µM Compound 2, or 2 µM Compound 7 on day 1. The dishes were then incubated further for 2 days at 37° C. Cells were then fixed in 4% paraformaldehyde, and tdTomato fluorescence in cells was assessed via confocal microscopy.

Figure 23:
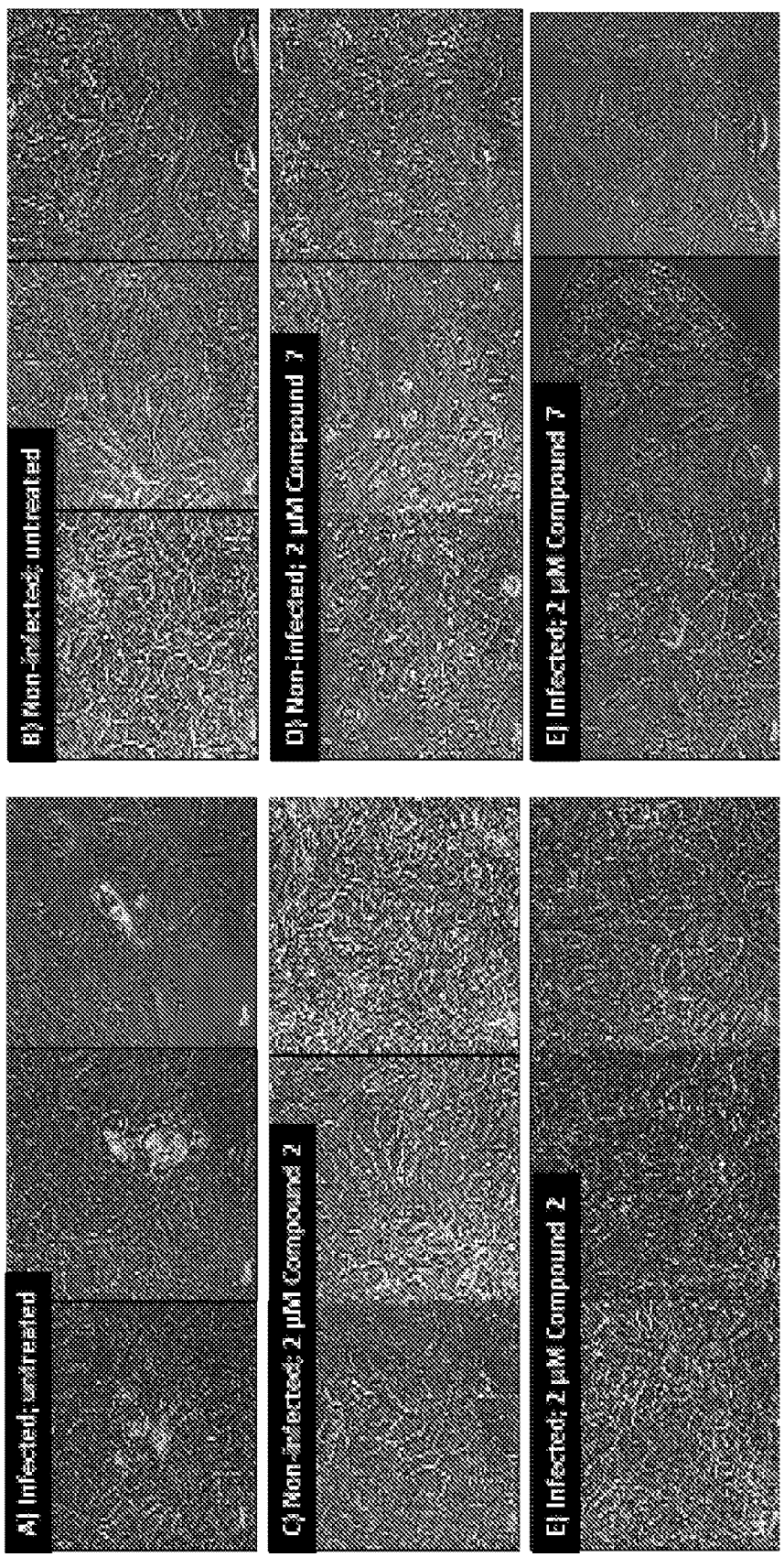
FIG. 23 ROW A shows images of *T. cruzi*-infected ARPE cells that were not treated with Compound 2 or Compound 7.

FIG. 23 ROW A shows images of *T. cruzi*-infected ARPE cells that were not treated with Compound 2 or Compound 7. FIG. 23 ROW B shows images of uninfected ARPE cells that were not treated with Compound 2 or Compound 7. FIG. 23 ROW C shows images of uninfected ARPE cells that were treated with 2 µM Compound 2. FIG. 23 ROW D shows images of uninfected ARPE cells that were treated with 2 µM Compound 7. FIG. 23 ROW shows images of *T. cruzi*-infected ARPE cells that were treated with 2 µM Compound 2. FIG. 23 ROW F shows images of *T. cruzi*-infected ARPE cells that were treated with 2 µM Compound 7. The results show that a single dose of 2 µM Compound 2 or Compound 7 killed intracellular *T. cruzi* and protected the cells from re-infection. ARPE cells treated with 2 µM of Compound 2 or Compound 7 had no *T. cruzi* intracellular amastigotes or much lower rates of *T. cruzi* intracellular amastigotes.

Example 18: Treatment of *T. cruzi*-Infected ARPE Cells with Various Concentrations of Compound 7

2×10$^4$ ARPE cells (ARPE-19; ATCC CRL-2302) were plated in individual confocal dishes and incubated at 37° C. for 16 hours to allow for cell adherence. The following dishes were prepared: 1) ARPE non-treated control cells; 2) non-infected but treated with either 5 µM, or 2.5 µM Compound 7; 3) non-treated but infected cells; and 4) infected cells treated with 5 µM, 2.5 µM, or 1 µM Compound 7. Designated dishes were incubated with ~2,×10$^6$ *T. cruzi*/mL for 24 hours at 37° C. to allow for internalization of parasites. *T. cruzi* parasites expressed tdTomato to allow for visualization of parasites within cells. After the 24-hour *T. cruzi* incubation, extracellular parasites were removed from dishes, and cells were washed three times with cell culture media (10% fetal bovine serum; 1% penicillin/streptomycin). Designated cells were then incubated with 5 µM, 2.5 or 1 µM Compound 7 for 3 days at 37° C. Cells were then fixed in 2% paraformaldehyde, and tdTomato fluorescence of the cells was assessed via confocal microscopy.

Figure 24:
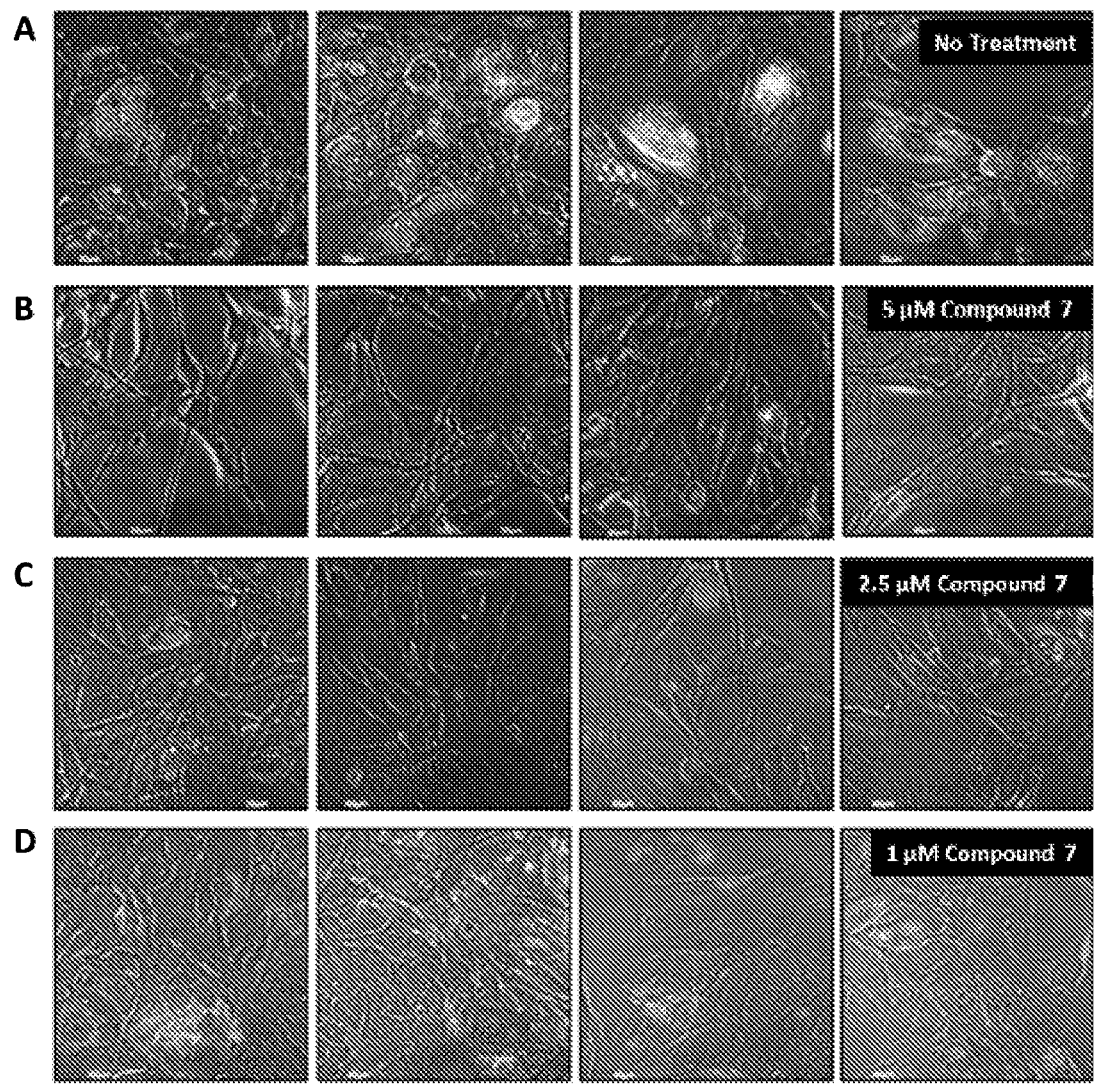
FIG. 24 ROW A shows images of *T. cruzi*-infected ARPE cells that did not receive treatment with Compound 7.

FIG. 24 ROW A shows images of *T. cruzi*-infected ARPE cells that did not receive treatment with Compound 7. FIG. 24 ROW B shows images of *T. cruzi*-infected ARPE cells that were treated with 5 µM Compound 7. FIG. 24 ROW C shows images of *T. cruzi*-infected ARPE cells that were treated with 2.5 µM Compound 7. FIG. 24 ROW D shows images of *T. cruzi*-infected ARPE cells that were treated with 1 µM Compound 7. The results show that *T. cruzi* was eradicated in ARPE cells treated with 5 µM Compound 7. *T. cruzi* infections in ARPE cells treated with 2.5 µM Compound 7 were minimal, and cells treated with 1 µM *T. cruzi* exhibited a decreased parasitic burden. However, cells treated with 1 µM Compound 7 were not protected from a recurring infection.

Example 19: Treatment of *T. cruzi*-Infected ARPE Cells with Compound 1

Human ARPEs were cultured and incubated with *T. cruzi* expressing tdTomato for 24 hours. Uninfected cells served as controls. Following the 24-hour *T. cruzi* incubation period, wells were washed twice with cell media and treated with 10 µM Compound 1 or left untreated as a control once per day for 2 days at 37° C. Cells were then imaged for tdTomato fluorescence.

Figure 25:
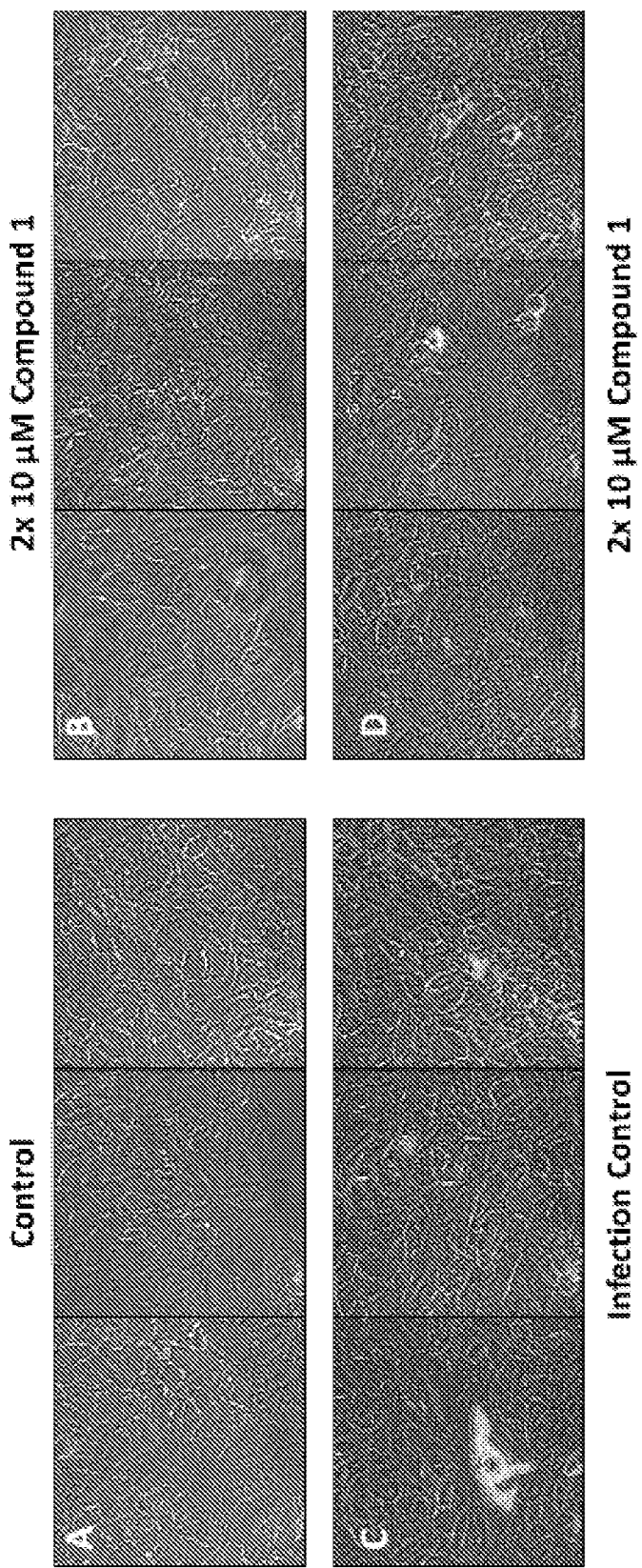
FIG. 25 ROW A shows images of uninfected human ARPE cells that were used as a control.

FIG. 25 ROW A shows images of uninfected human ARPE cells that were used as a control. FIG. 25 ROW B shows images of uninfected ARPE cells that were treated with 10 µM Compound 1. FIG. 25 ROW C shows images of *T. cruzi*-infected ARPE cells that were untreated and used as controls. FIG. 25 ROW D shows images of *T. cruzi*-infected ARPE cells that were treated with 10 µM Compound 1. The results show that treatment with Compound 1 decreased the number of intracellular parasites observed in ARPE culture. The images of uninfected cells treated with Compound 1 (FIG. 25 ROW B) and images of *T. cruzi*-infected cells treated with Compound 1 (FIG. 25 ROW D) look similar because Compound 1 successfully cleared the ARPE cells of the *T. cruzi* infection.

Example 20: Treatment of *T. cruzi*-Infected African Green Monkey Kidney Cells (VERO; ATCC CCL-81) with Compound 2 and Compound 7

2×10$^4$ VERO cells were plated in individual confocal dishes and allowed to adhere for 16 hours at 37° C. 6 dishes were prepared: 1) VERO non-treated control cells; 2) non-infected cells treated with 5 µM Compound 2; 3) non-infected cells treated with 5 µM Compound 7; 4) *T. cruzi*-infected cells that did not receive treatment; 5) *T. cruzi*-infected cells treated with 5 µM Compound 2; and 6) *T. cruzi*-infected cells treated with 5 µM Compound 7. The *T. cruzi*-infected dishes were incubated with ~2×10$^6$ *T. cruzi*/mL for 24 hours at 37° C. to allow for internalization of parasites. *T. cruzi* parasites expressed tdTomato, which allowed for visualization of parasites within cells. After the 24-hour *T. cruzi* incubation period, extracellular parasites were removed from culture dishes. The cells were washed 3 times with cell culture media (10% fetal bovine serum; 1% penicillin/streptomycin). Designated plates were then incubated with 5 µM Compound 2 or 5 µM Compound 7 for 5 days at 37° C. Cells were then fixed in 2% paraformaldehyde and tdTomato fluorescence in cells was assessed via confocal microscopy.

Figure 26:
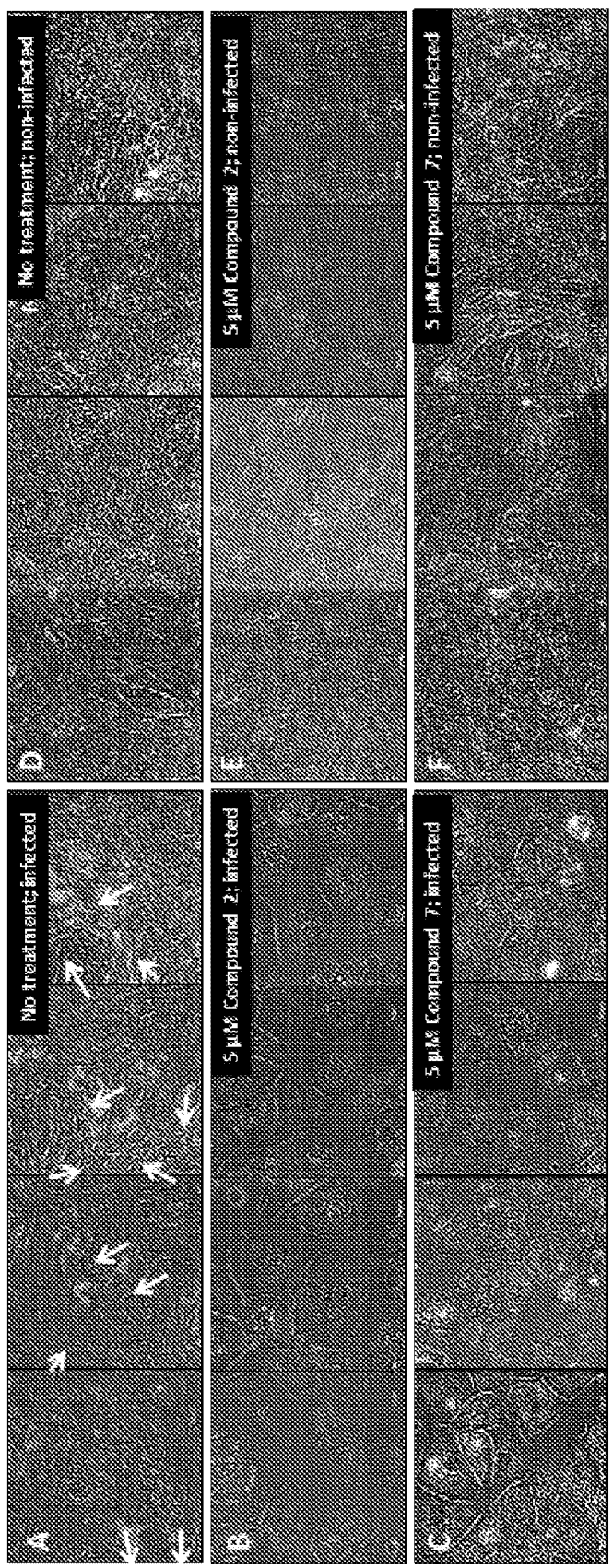
FIG. 26 ROW A shows images of *T. cruzi*-infected VERO cells that did not receive treatment with Compound 2 or Compound 7.

FIG. 26 ROW A shows images of *T. cruzi*-infected VERO cells that did not receive treatment with Compound 2 or Compound 7. FIG. 26 ROW B shows images of *T. cruzi*-infected VERO cells that were treated with 5 µM Compound 2. FIG. 26 ROW C shows images of *T. cruzi*-infected VERO cells that were treated with 5 µM Compound 7. FIG. 26 ROW D shows images of uninfected VERO cells that were not treated with Compound 2 or Compound 7. FIG. 26 ROW E shows images of uninfected VERO cells that were treated with 5 µM Compound 2.

FIG. 26 ROW F shows images of uninfected VERO cells that were treated with 5 µM Compound 7. The results show that treatment with 5 µM Compound 2 or 5 µM Compound 7 for 5 days resulted in the eradication of *T. cruzi* infection in VERO cells.

Example 21: Effect of Nifurtimox Treatment on *T. cruzi* Epimastigotes, Amastigotes, and Trypomastigotes

*T. cruzi* epimastigotes, amastigotes, or trypomastigotes were plated at 2×10$^5$ cells per well in a 96 well plate. Plated epimastigotes were prepared in LIT1029 medium, while amastigotes and trypomastigotes were collected after being passaged in ARPE cells. *T. cruzi* cells were treated with 0 µM, 0.39 µM, 0.78 µM, 1.56 µM, 3.125 µM, 6.25 µM, 12.5 µM, 25 µM, 50 µM, or 100 µM of nifurtimox for 48 hours at 37° C. After treatment with nifurtimox, *T. cruzi* viability was assessed via an ATP assay. An increase in RLU indicated the presence of ATP and viable cells.

Figure 27:
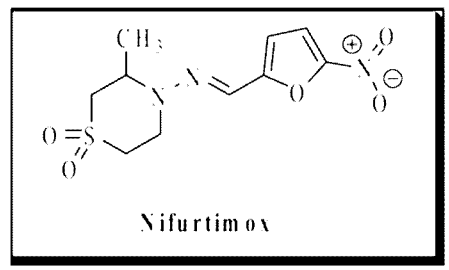
FIG. 27 PANEL A shows the effect of nifurtimox on *T. cruzi* epimastigotes.
Figure 27:
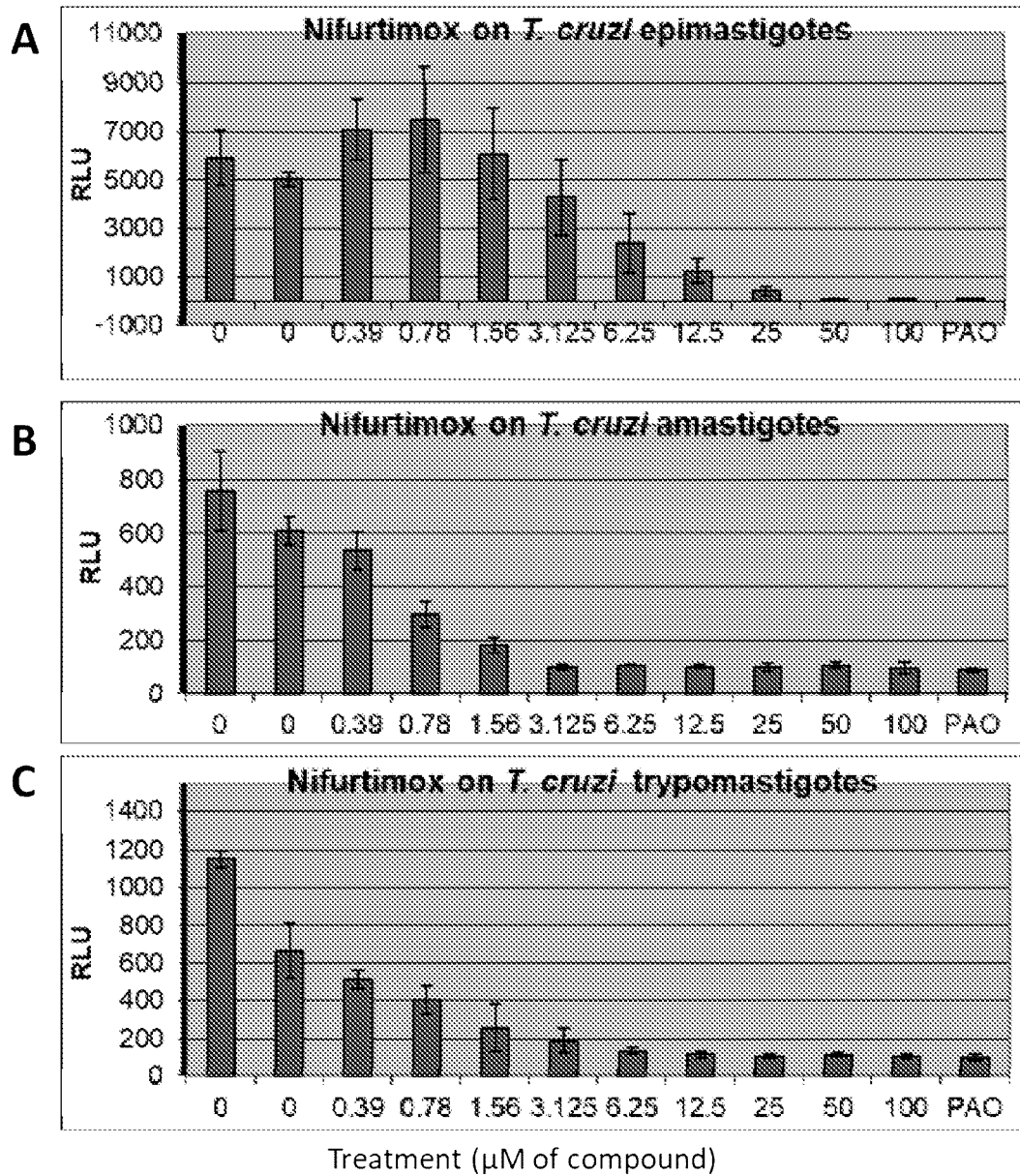

FIG. 27 PANEL A shows the effect of nifurtimox on *T. cruzi* epimastigotes. FIG. 27 PANEL B shows the effect of nifurtimox on *T. cruzi* amastigotes. FIG. 27 PANEL C shows the effect of nifurtimox on *T. cruzi* trypomastigotes. The results show that the MIC of nifurtimox was 25 µM in epimastigotes, 3.12 µM in amastigotes, and 6.25 µM in trypomastigotes.

Example 22: Effect of Benznidazole Treatment on *T. cruzi* Epimastigotes, Amastigotes, and Trypomastigotes

*T. cruzi* epimastigotes, amastigotes, or trypomastigotes were plated at 2×10$^5$ cells per well in a 96 well plate. Plated epimastigotes were prepared in LIT1029 medium, while amastigotes and trypomastigotes were collected after being passaged in ARPE cells. *T. cruzi* cells were treated with 0 µM, 0.39 µM, 0.78 µM, 1.56 µM, 3.125 µM, 6.25 µM, 12.5 µM, 25 µM, 50 µM, or 100 µM of benznidazole for 48 hours at 37° C. After treatment with benznidazole, *T. cruzi* viability was assessed via an ATP assay. An increase in RLUs indicated the presence of ATP and viable cells.

Figure 28:
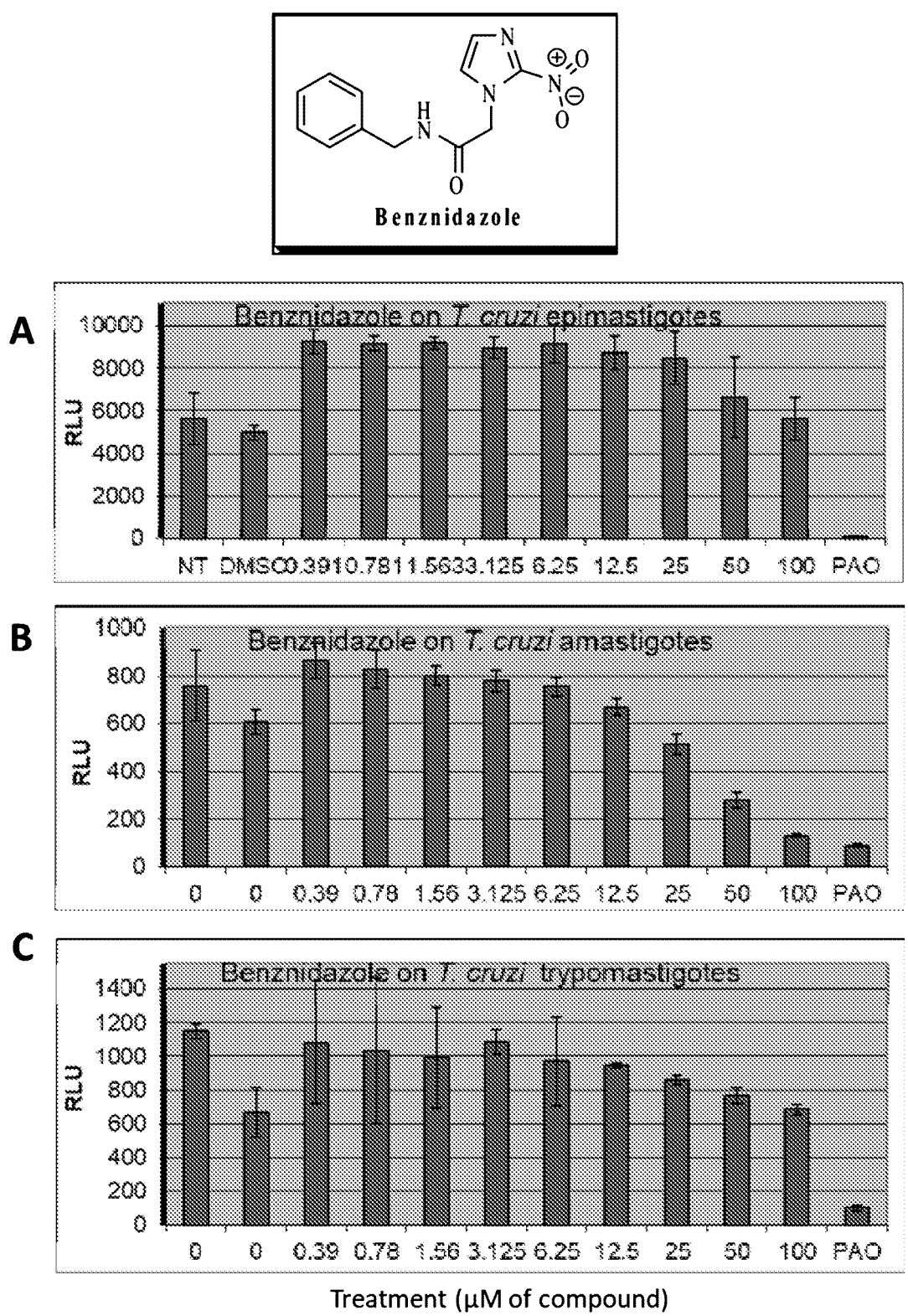
FIG. 28 PANEL A shows the effect of benznidazole on *T. cruzi* epimastigotes.

FIG. 28 PANEL A shows the effect of benznidazole on *T. cruzi* epimastigotes. FIG. 28 PANEL B shows the effect of benznidazole on *T. cruzi* amastigotes. FIG. 28 PANEL C shows the effect of benznidazole on *T. cruzi* trypomastigotes. The results show that the MIC of benznidazole was >100 µM in epimastigotes, 100 µM in amastigotes, and >100 µM in trypomastigotes.

The ability of benznidazole treatment to clear *T. cruzi* infection in ARPE cells was also assessed. ARPE cells were cultured (20,000 cells per plate) and incubated with *T. cruzi* amastigotes and trypomastigotes expressing tdTomato (~2×10$^5$ cells) for 24 hours at 37° C. Uninfected plates served as controls. Following infection, wells were washed three times with DMEM/F12 (10% FBS), and cells were incubated with fresh media with or without 2 benznidazole for 2 days at 37° C. At the end of this 2-day incubation, tdTomato fluorescence in cells was assessed via confocal microscopy.

Figure 29:
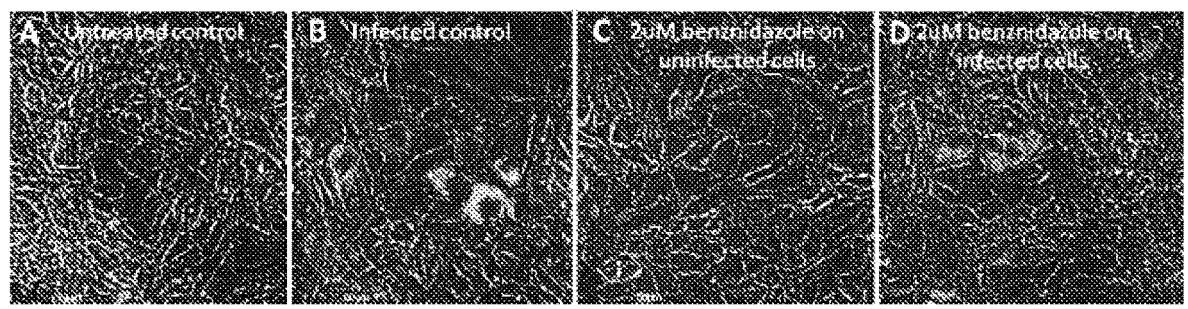
FIG. 29 PANEL A shows an image of uninfected ARPE cells used as a control.

FIG. 29 PANEL A shows an image of uninfected ARPE cells used as a control. FIG. 29 PANEL B shows *T. cruzi*-infected ARPE cells used as a control. FIG. 29 PANEL C shows uninfected ARPE cells treated with 2 µM benznidazole. FIG. 29 PANEL D shows *T. cruzi*-infected ARPE cells treated with 2 µM benznidazole. The data show that ARPE cells that were pre-infected with *T. cruzi* and then treated with 2 µM benznidazole for 2 days were not cleared from *T. cruzi* infection.

Example 23: Treatment of *T. gondii*-Infected ARPE Cells

ARPE cells were cultured at confluency in a 24 well plate. Cells were incubated with *T. gondii* (ATCC PRA-310) for 1 hour at 37° C. to allow for *T. gondii* internalization. After the 1-hour *T. gondii* incubation period, extracellular *T. gondii* was removed from culture and cells were washed 3 times with cell media. Cells were then treated with 1, 2, or 5 µM Compound 2 for 4 days at 37° C. Cells were visualized using an EVOS cell imaging system.

Figure 30:
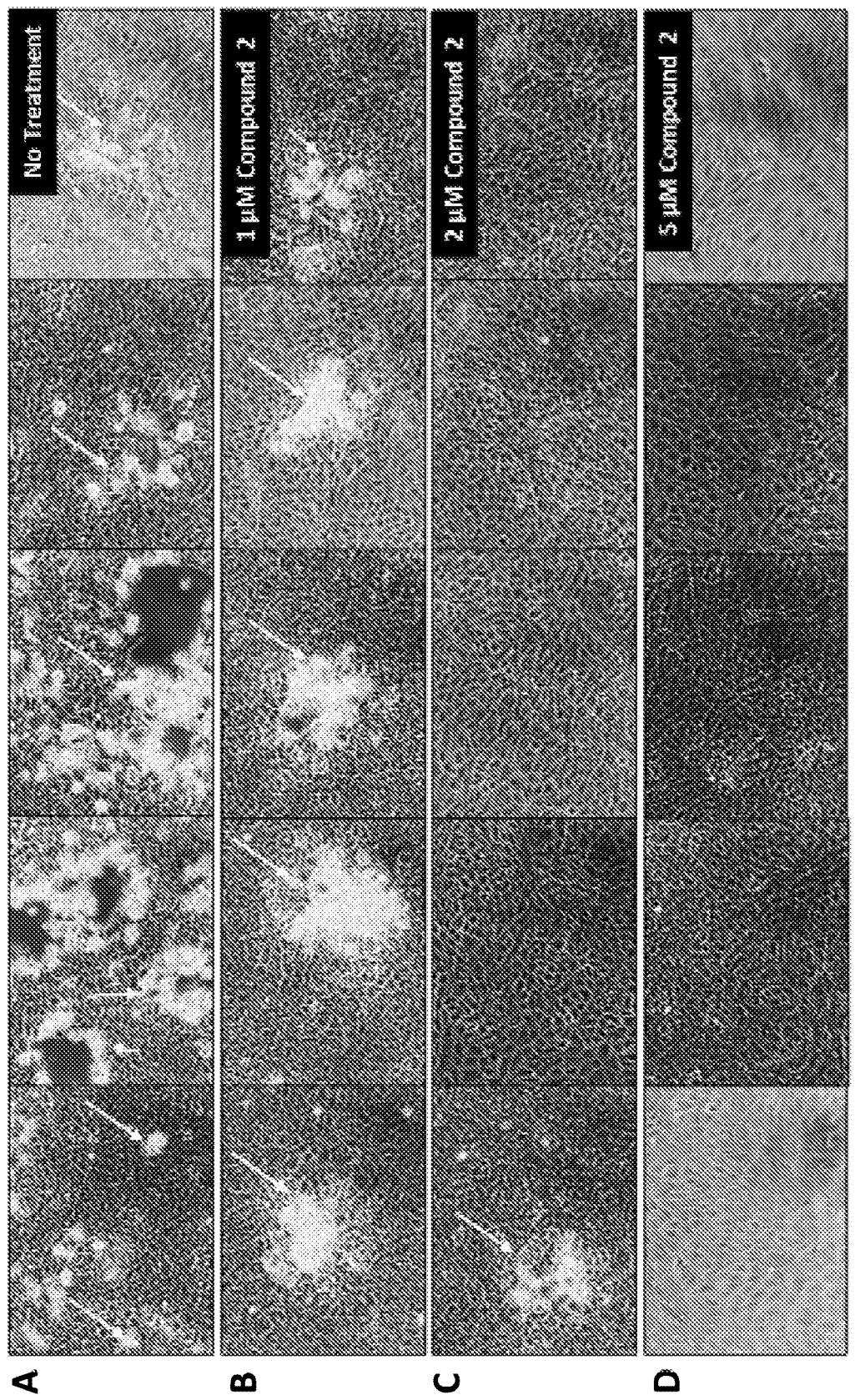
FIG. 30 ROW A shows images of *T. gondii*-infected ARPE cells that were not treated with Compound 2.

FIG. 30 ROW A shows images of *T. gondii*-infected ARPE cells that were not treated with Compound 2. FIG. 30 ROW B shows *T. gondii*-infected ARPE cells treated with 1 Compound 2. FIG. 30 ROW C shows *T. gondii*-infected ARPE cells treated with 2 Compound 2. FIG. 30 ROW D shows *T. gondii*-infected ARPE cells treated with 5 Compound 2. The data show that treatment with 2 or 5 µM Compound 2 resulted in clearance of *T. gondii* from ARPE cells. *T. gondii* appears as small, dense, and mostly birefringent in the presented images.

The effect of a 3-day Compound 2 treatment on *T. gondii*-infected ARPE cells was also investigated. 2×10$^4$ ARPE cells were infected with ~1×10$^6$ *T. gondii* parasites as described in the above paragraph. Cells were then incubated with 5 µM Compound 2 for 3 days at 37° C. Following incubation with Compound 2, cells were washed 3 times in cell media, fixed with 4% paraformaldehyde, stained with DAPI, and visualized with confocal microscopy.

Figure 31:
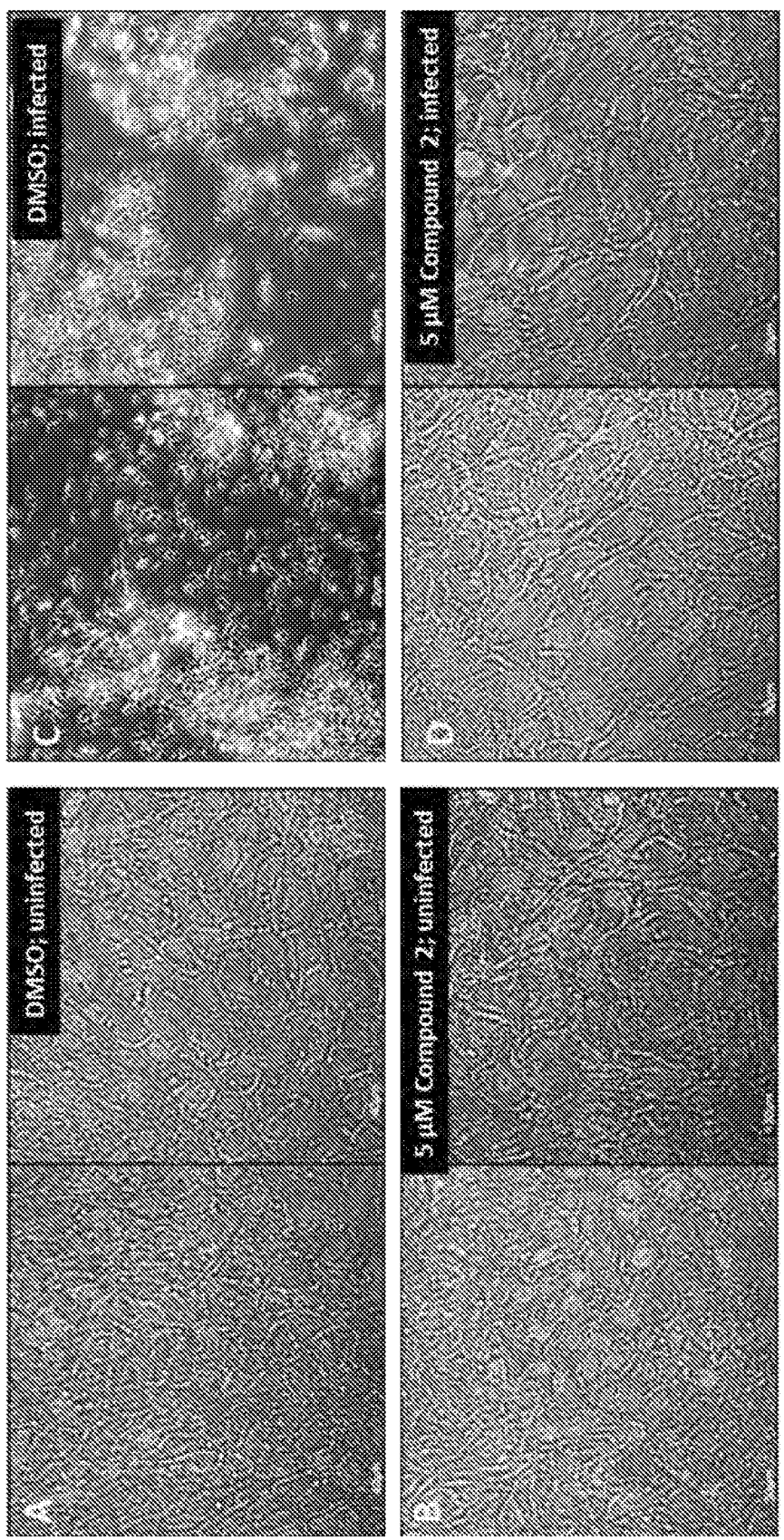
FIG. 31 PANEL A shows images of uninfected ARPE cells that were treated with DMSO for 3 days.

FIG. 31 PANEL A shows images of uninfected ARPE cells that were treated with DMSO for 3 days. FIG. 31 PANEL B shows images of uninfected ARPE cells that were treated with 5 µM Compound 2 for 3 days. FIG. 31 PANEL C shows images of *T. gondii*-infected ARPE cells that were treated with DMSO for 3 days. FIG. 31 PANEL D shows images of *T. gondii*-infected ARPE cells that were treated with 5 µM Compound 2 for 3 days. The data show that a 3-day treatment with 5 µM Compound 2 cleared ARPE cells of *T. gondii* infection. *T. gondii*-infected cells appear as pale clusters in confocal images.

Figure 32:
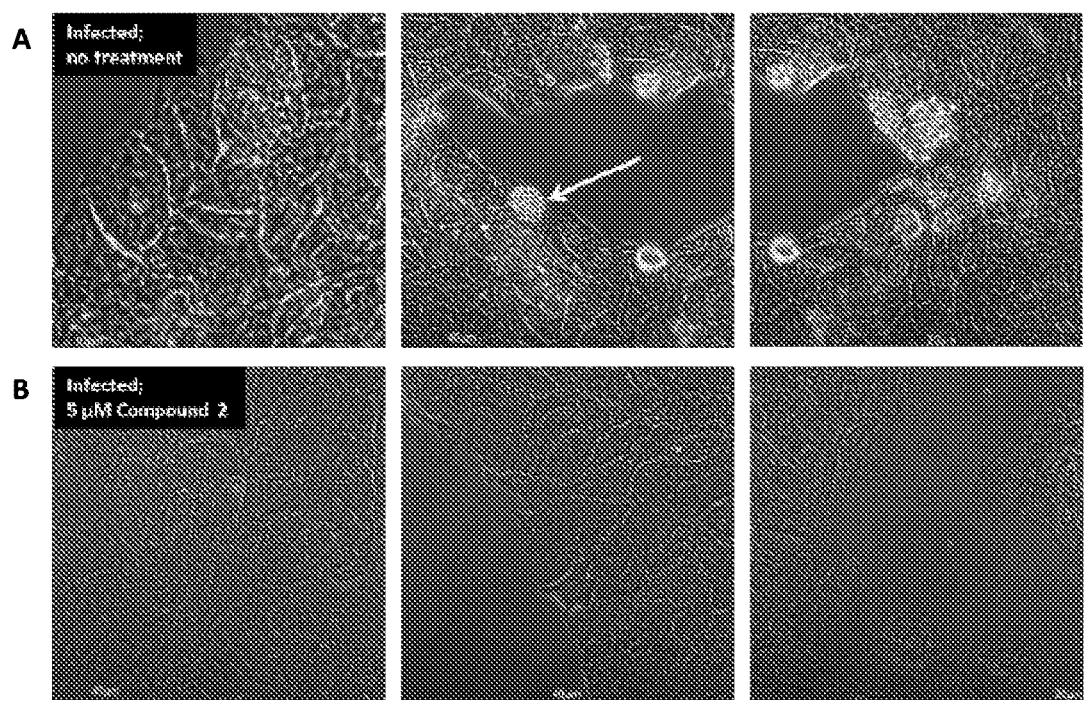
FIG. 32 ROW A shows images of *T. gondii*-infected ARPE cells that were not treated and incubated for 5 days.

FIG. 32 ROW A shows images of *T. gondii*-infected ARPE cells that were not treated and incubated for 5 days. FIG. 32 ROW B shows images of *T. gondii*-infected ARPE cells that were treated with 5 µM Compound 2 for 5 days. The data show that a 5-day treatment with 5 µM Compound 2 cleared ARPE cells of *T. gondii* infection. *T. gondii*-infected cells appear as pale clusters in confocal images.

Example 24: Treatment of *P. falciparum*-Infected Red Blood Cells with Compounds of the Disclosure Blood samples infected with *P. falciparum* (isolate 3D7) were diluted to 1% parasitemia and 2% hematocrit values and treated with 50 µM Compound 2, 5 µM Compound 2, 2.5 µM Compound 2, 50 µM Compound 7, 5 µM Compound 7, 2.5 µM Compound 7, 50 µM Compound 1, 5 µM Compound 1, 50 µM Compound 3, 5 µM Compound 3, 50 µM Compound 4, 5 µM Compound 4, 50 µM Compound 5, 5 µM Compound 5, 50 µM Compound 6, 5 µM Compound 6, 50 µM Compound 7, 5 µM Compound 7, 50 µM Compound 8, 5 µM Compound 8, 50 µM Compound 9, 5 µM Compound 9, 50 µM Compound 10, 5 µM Compound 10, 50 µM Compound 11, or 5 µM Compound 11 for 72 hours. Treatment with the anti-malarial drug chloroquine served as a positive control. After compound treatment, red blood cells were lysed, and parasite survival was determined with a SYBR Green assay. A decrease in mean relative fluorescence indicates higher compound efficacy because SYBR green binds to DNA in uncompromised P. falciparum and releases fluorescence.

Figure 33:
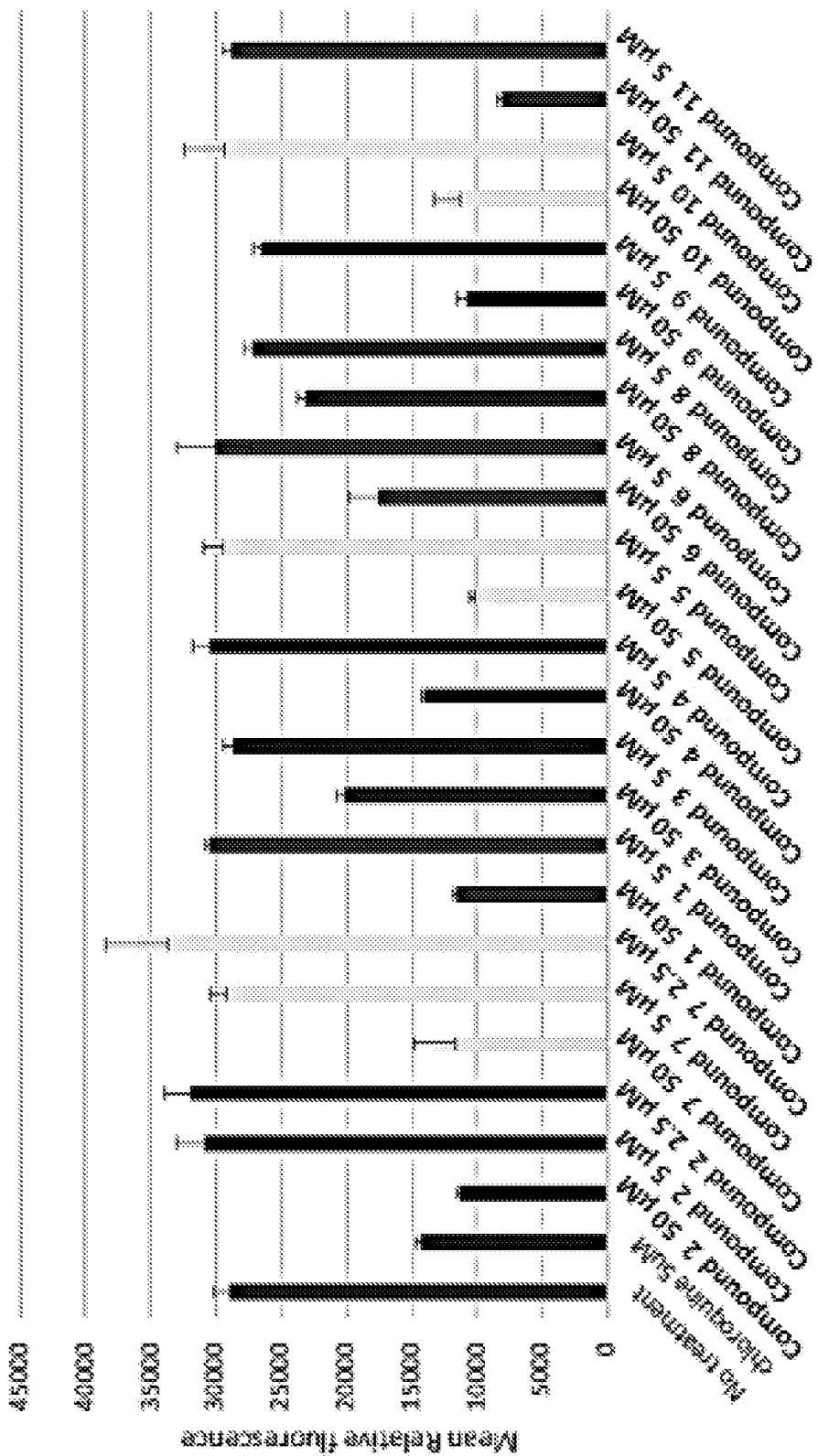
FIG. 33 shows the mean relative fluorescence values of compounds of the disclosure at concentrations ranging from 2.5 µM to 50 µM.

FIG. 33 shows the mean relative fluorescence values of various compounds of the disclosure at concentrations ranging from 2.5 μM to 50 μM.

Blood samples infected with P. falciparum (isolate 3D7) were diluted to 1% parasitemia and 2% hematocrit values and treated with varying concentrations of different compounds of the disclosure for 72 hours. After treatment with the compounds of the disclosure, the red blood cells were lysed, and parasite survival was determined with a SYBR green assay. A decrease in mean relative fluorescence indicates higher compound efficacy because SYBR green binds to DNA in uncompromised P. falciparum and releases fluorescence.

Figure 34:
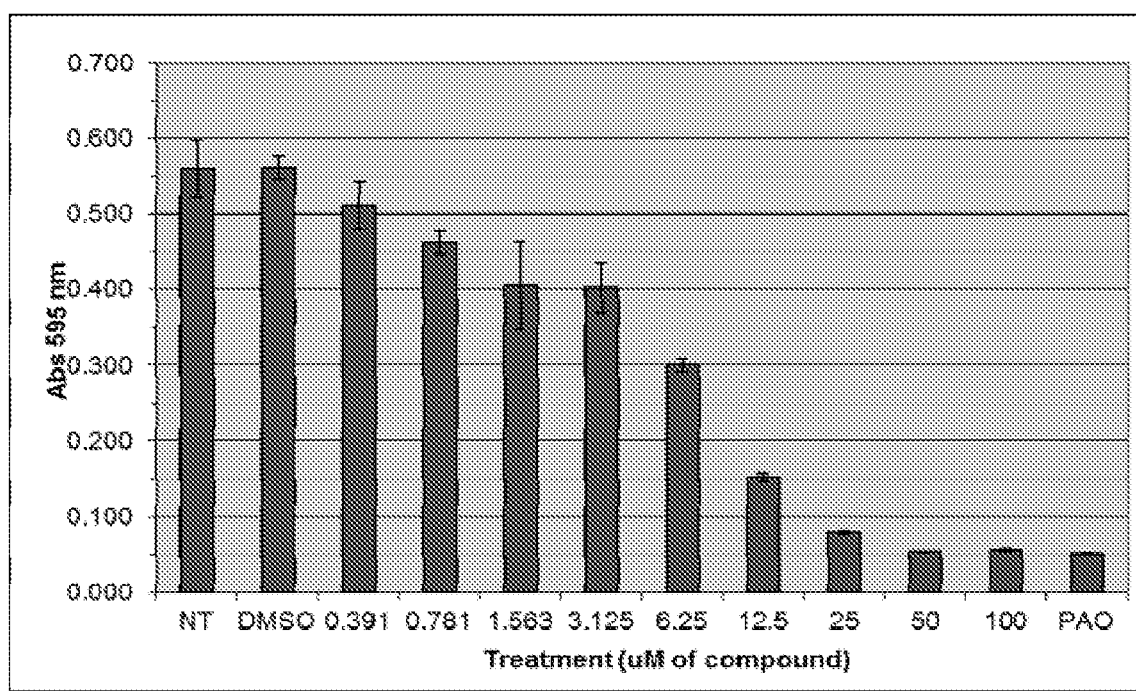
FIG. 34 shows the *P. falciparum* dose response to Compound 2 in *P. falciparum*-infected red blood cells.

FIG. 34 shows the P. falciparum dose response to Compound 2 in P. falciparum-infected red blood cells.

Example 25: Treatment of L. major Promastigotes with Compound 2 and Compound 5

$5 \times 10^5$ L. major promastigotes were treated with vehicle control (DMSO), 5 Compound 2, 5 μM Compound 5, 50 μM Compound 2, 50 μM Compound 5, or 5 miltefosine (MTF) for 48 hours at 24° C. Promastigote viability was then assessed via a propidium iodide flow cytometry assay. Propidium iodide is only taken up by dead cells, and the presence of fluorescence in a promastigote sample reflects compound efficacy.

Figure 35:
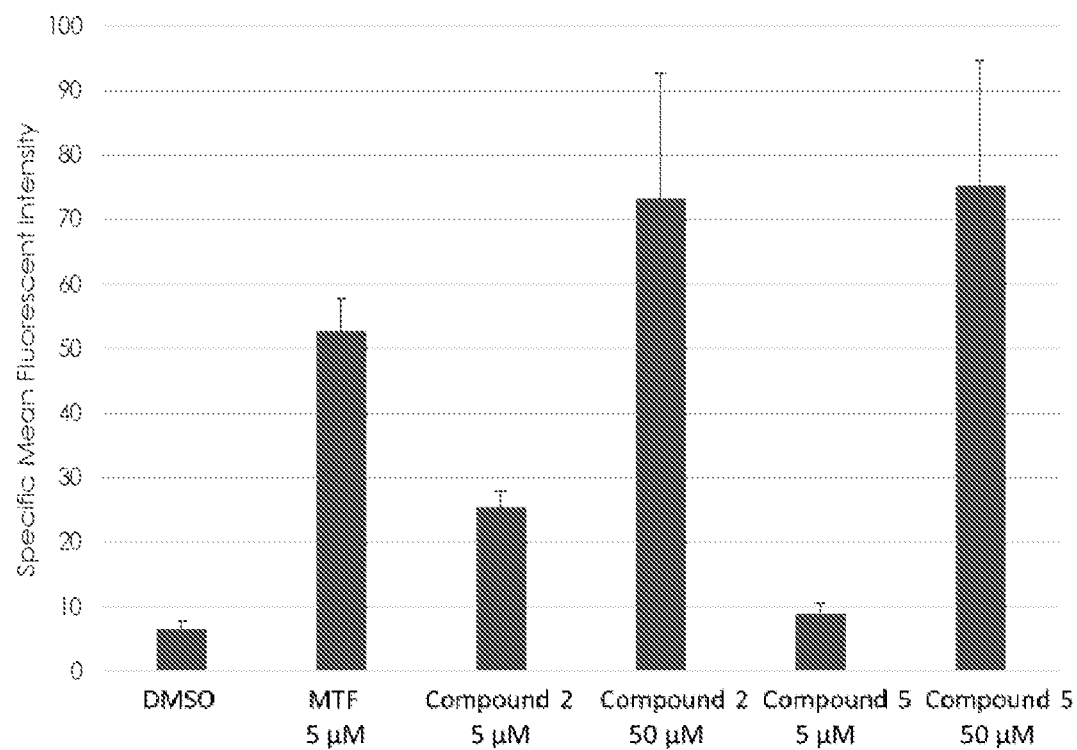
FIG. 35 shows the effect of varying concentration of Compound 2 and Compound 5 on *L. major* promastigote survival.

FIG. 35 shows the effect of varying concentration of Compound 2 and Compound 5 on L. major promastigote survival. An increase in specific mean fluorescence intensity indicates higher compound efficacy. The data show that Compound 2 and Compound 5 had higher efficacy than MTF or the vehicle control at concentrations of 50 μM.

Example 26: Treatment of L. major Promastigotes with Various Compounds of the Disclosure $1 \times 10^5$ L. major promastigotes, seeded in wells of 96-well plates, were treated with vehicle control (DMSO), 5 μM MTF, or 5 μM or 50 μM of Compound 1, Compound 3, Compound 4, Compound 6, Compound 7, Compound 8, Compound 9, or Compound 11 for 48 hours at 24° C. At the end of the treatment period, 75 μL of 5×SYBR Green/5% Triton X-100 was added to each well and incubated with promastigotes for 30 minutes. Wells were then excited with 487 nm light, and SYBR Green fluorescence from each well was detected at 528 nm. SYBR green binds to DNA in uncompromised promastigotes and releases fluorescence. A decrease in mean RFUs indicates an increased compound efficacy.

Figure 36:
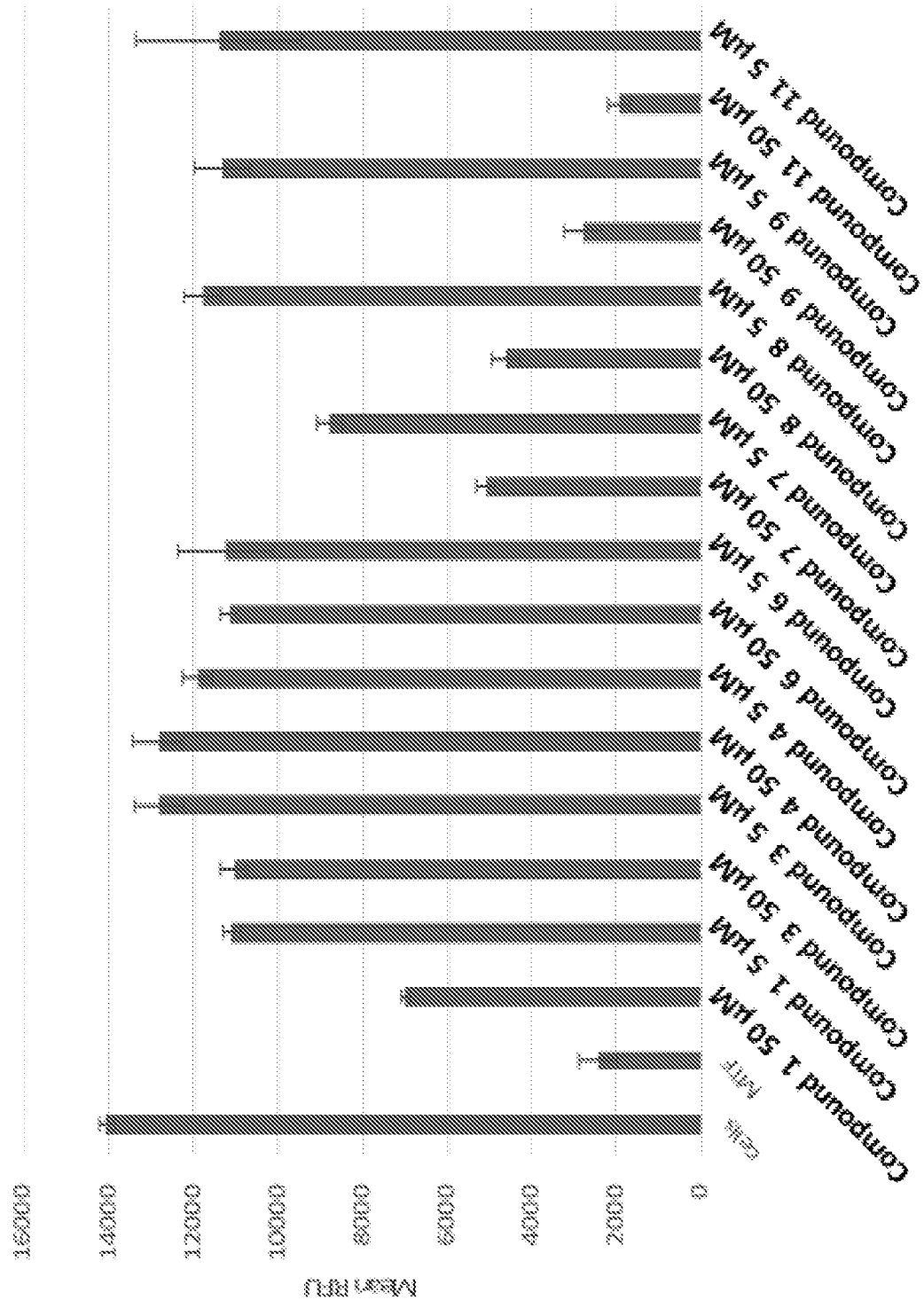
FIG. 36 shows the effects of compounds of the disclosure at different concentrations on *L. major* promastigote survival.

FIG. 36 shows the effects of various compounds of the disclosure at different concentrations on L. major promastigote survival.

Example 27: Treatment of L. major-Infected Monocyte-Derived Macrophages with Miltefosine or Compounds of the Disclosure Human peripheral blood mononuclear cells (PBMC) were plated onto polylysine-coated glass slides in 24-well plates and allowed to differentiate towards monocyte-derived macrophages (MDMs). Non-adherent cells were removed 48-hours post plating. Adherent monocytes were left to further differentiate for another 48 hours to MDMs. Following the completion of the differentiation period, MDMs were treated with vehicle control (DMSO), 5 miltefosine (MTF), or 10 μM of Compound 1, Compound 3, Compound 4, Compound 6, Compound 7, Compound 8, Compound 9, Compound 10, or Compound 11 for 48 hours.

Figure 37:
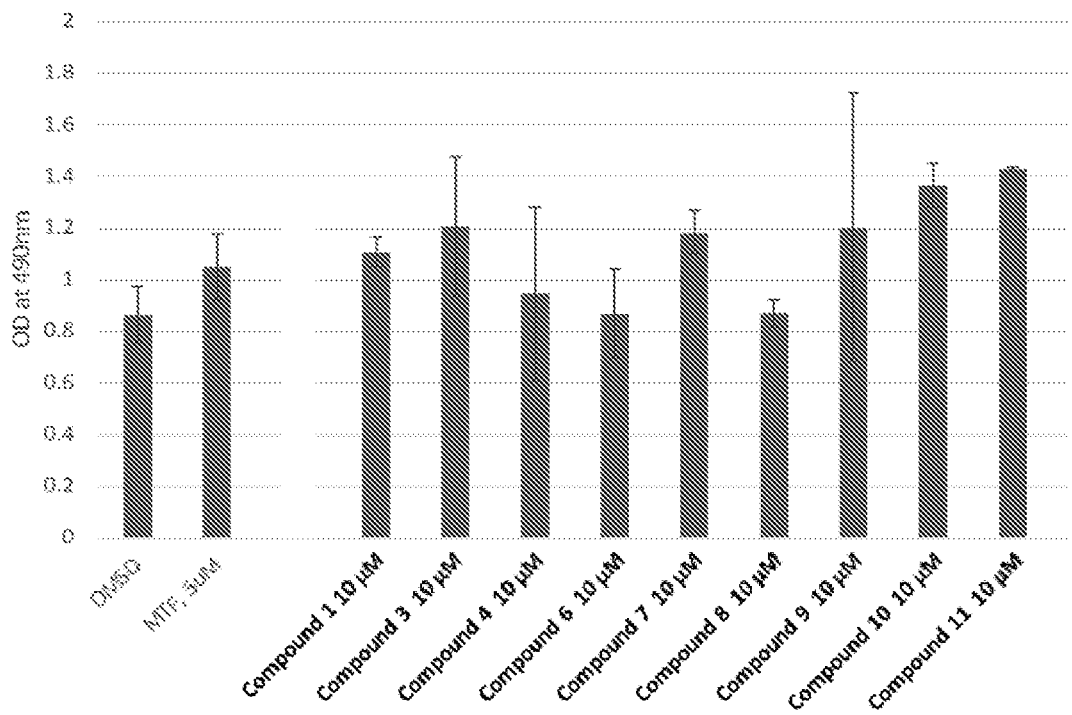
FIG. 37 shows MTT assay data demonstrating that MTF and compounds of the disclosure were not toxic to PBMC cells.

FIG. 37 shows MTT assay data demonstrating that MTF and the compounds of the disclosure were not toxic to PBMC cells.

Figure 38:
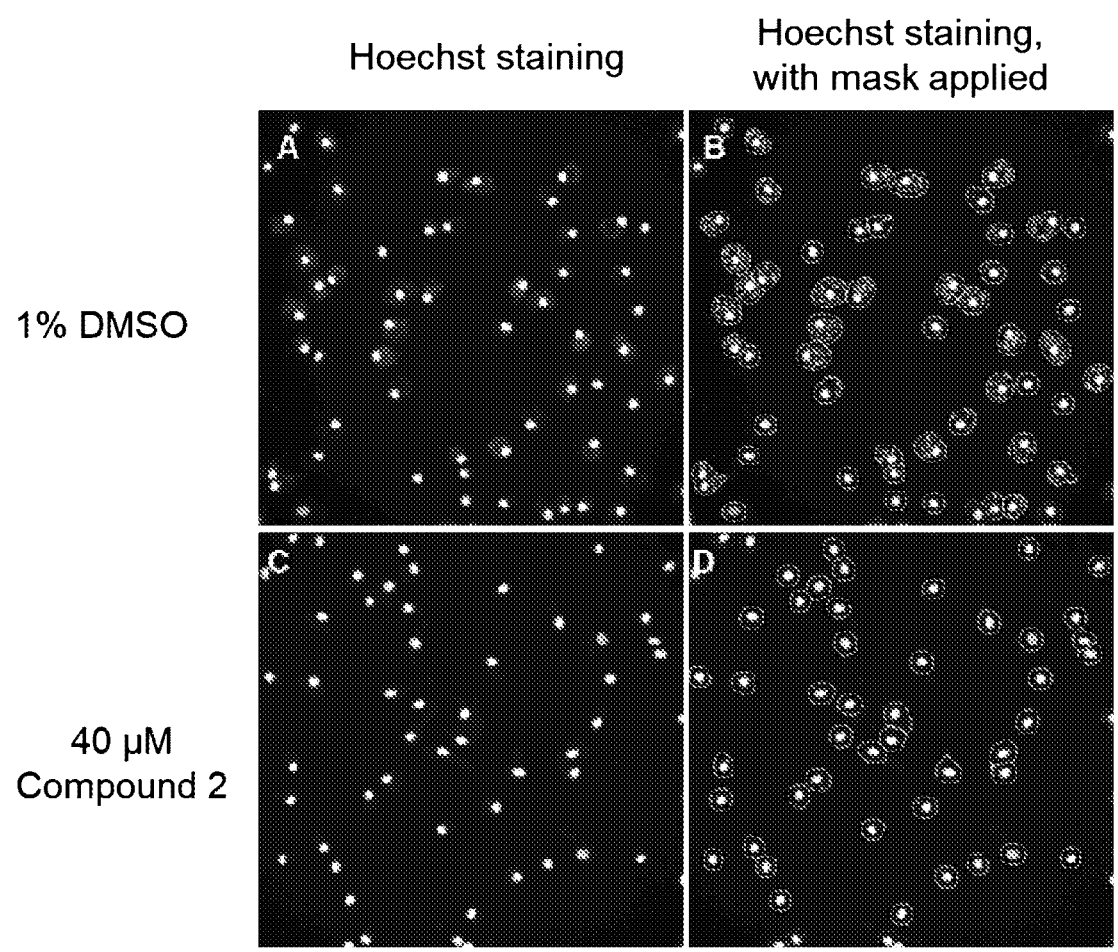
FIG. 38 PANEL A shows a micrograph image of *L. major*-infected PBMC cells treated with 1% DMSO.

FIG. 38 PANEL A shows a micrograph image of L. major-infected PBMC cells treated with 1% DMSO. FIG. 38 PANEL B shows a micrograph image of L. major-infected PBMC cells treated with 1% DMSO and treated with Hoechst staining. FIG. 38 PANEL C shows a micrograph image of L. major-infected PBMC cells treated with 40 μM Compound 2. FIG. 38 PANEL D shows a micrograph image of L. major-infected PBMC cells treated with 40 μM Compound 2 and Hoechst staining.

Figure 39:
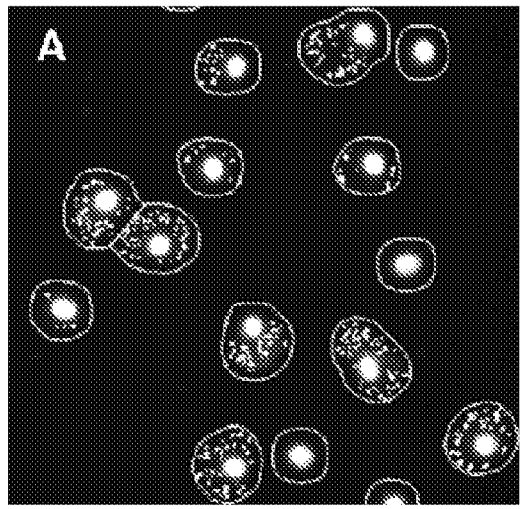
FIG. 39 PANEL A shows a magnified image of *L. major*-infected PBMC cells treated with 1% DMSO and treated with Hoechst staining.
Figure 39:
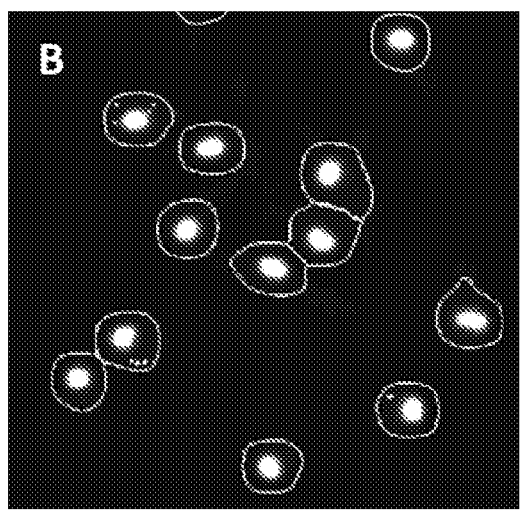

FIG. 39 PANEL A shows a magnified image of L. major-infected PBMC cells treated with 1% DMSO and treated with Hoechst staining. FIG. 39 PANEL B shows a magnified image of L. major-infected PBMC cells treated with 40 μM Compound 2 and Hoechst staining. The images show that treatment of L. major-infected PBMC cells decreases the number of parasites/PBMC cell (tiny specks in the cytoplasm).

Following an analogous differentiation, infection, and treatment procedure as described above, the number of parasites per cell was counted using a CellInsight CX7 High-Content Screening Platform.

Figure 40:
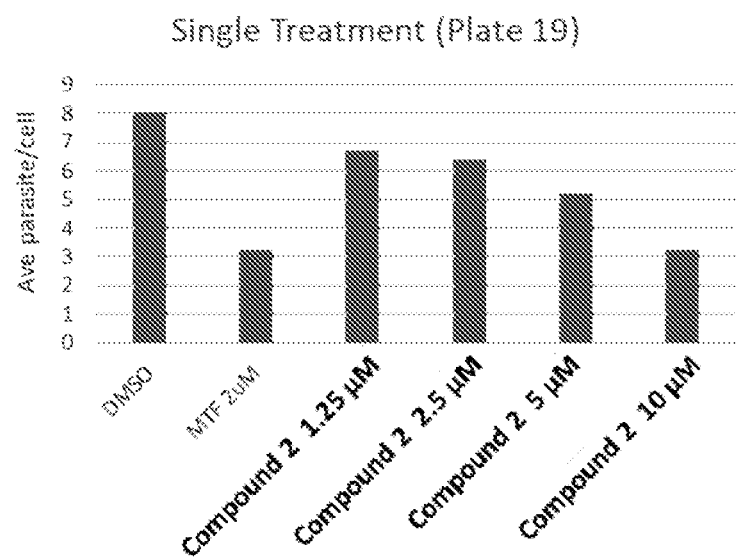
FIG. 40. PANEL A shows the outcome from a single treatment at the shown concentration.
Figure 40:
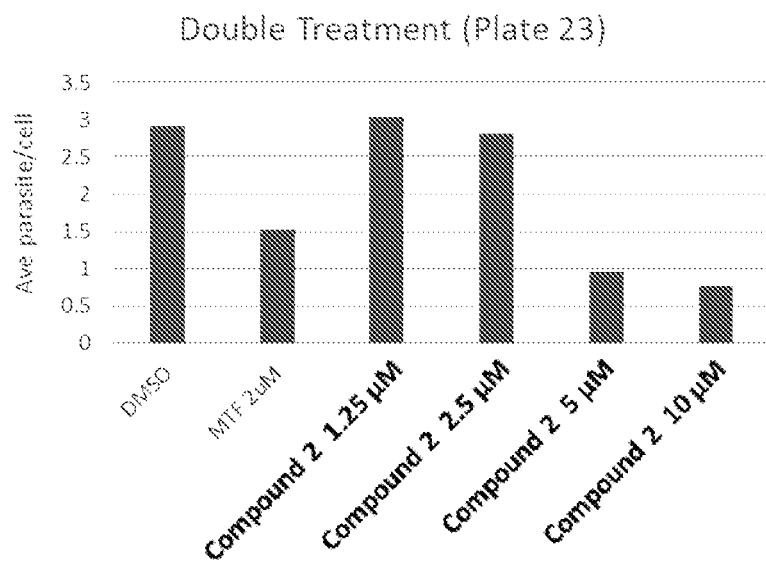

FIG. 40. PANEL A shows the outcome from a single treatment at the shown concentration. FIG. 40. PANEL B shows the outcome of a double treatment (media removed after 24 hours and replaced with media containing the same concentration of shown drug for an additional 24 hours). The results show that there was a concentration-dependent decrease in the number of parasites per cell.

Example 28: Compound 2 Treatment of Macrophages Infected with T. cruzi

Macrophages derived by differentiation of THP-1 cells with phorbol myristate acetate were plated in confocal dishes (about 5,000 cells per dish) and incubated overnight at 37° C. Dishes were incubated with T. cruzi amastigotes and trypomastigotes expressing tdTomato (~$2 \times 10^5$ cells) for 24 hours at 37° C. Uninfected plates served as controls. After the 24-hour T. cruzi incubation period, parasites were removed, and medium was re-plated with DMEM/F12 culture media with 2 μM Compound 2 (or left untreated as a control) for 7 days at 37° C. Following fixation of cells in 4% paraformaldehyde, tdTomato fluorescence (which is indicative of viable T. cruzi) in cells was then assessed via confocal microscopy.

Figure 41:
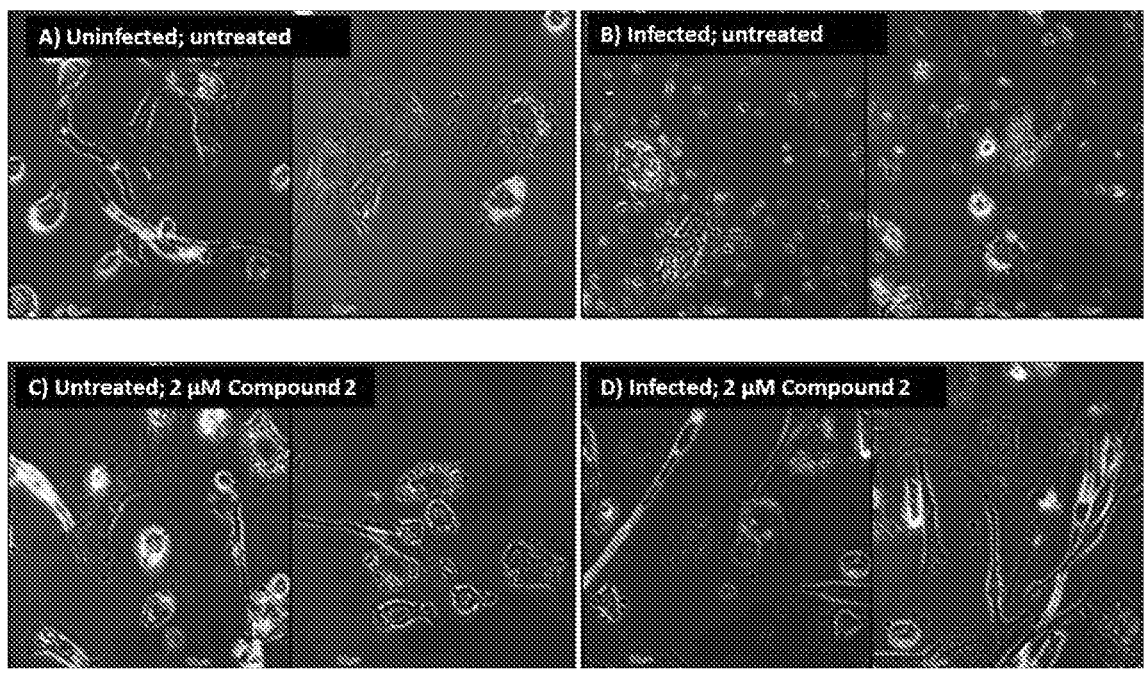
FIG. 41 PANEL A shows images of uninfected THP-1 cells that were untreated.

FIG. 41 PANEL A shows images of uninfected THP-1 cells that were untreated. FIG. 41 PANEL B shows images of uninfected THP-1 cells treated with 2 μM Compound 2. FIG. 41 PANEL C shows images of T. cruzi-infected THP-1 cells that were untreated. FIG. 41 PANEL D shows images of T. cruzi-infected THP-1 cells that were treated with 2 μM Compound 2. The results show that treatment with 2 μM Compound 2 prevented intracellular proliferation of T. cruzi.

Example 29: Treatment of L. major-Infected MDMs with Compound 2 and Compound 7

Human MDMs were cultured on glass slides and incubated with metacyclic L. major for 24 hours to allow for internalization of parasites. After the 24-hour *L. major* incubation period, extracellular parasites were removed from the culture. 24 hours after the removal of extracellular parasites, infected cells were treated with vehicle control (DMSO), 5 µM MTF, 1 µM Compound 2, 5 µM Compound 2, 10 µM Compound 2, 2 µM Compound 7, or 20 µM Compound 7. Following treatment, the cells were fixed with 2% paraformaldehyde and subsequently stained with the DNA stain Hoechst 33342. The stained cover slips were transferred onto glass slides, and quantitative cell bioimaging was utilized to determine the number of amastigotes per 500 cells using a CellInsight CX5 High Content screening platform.

Figure 42:
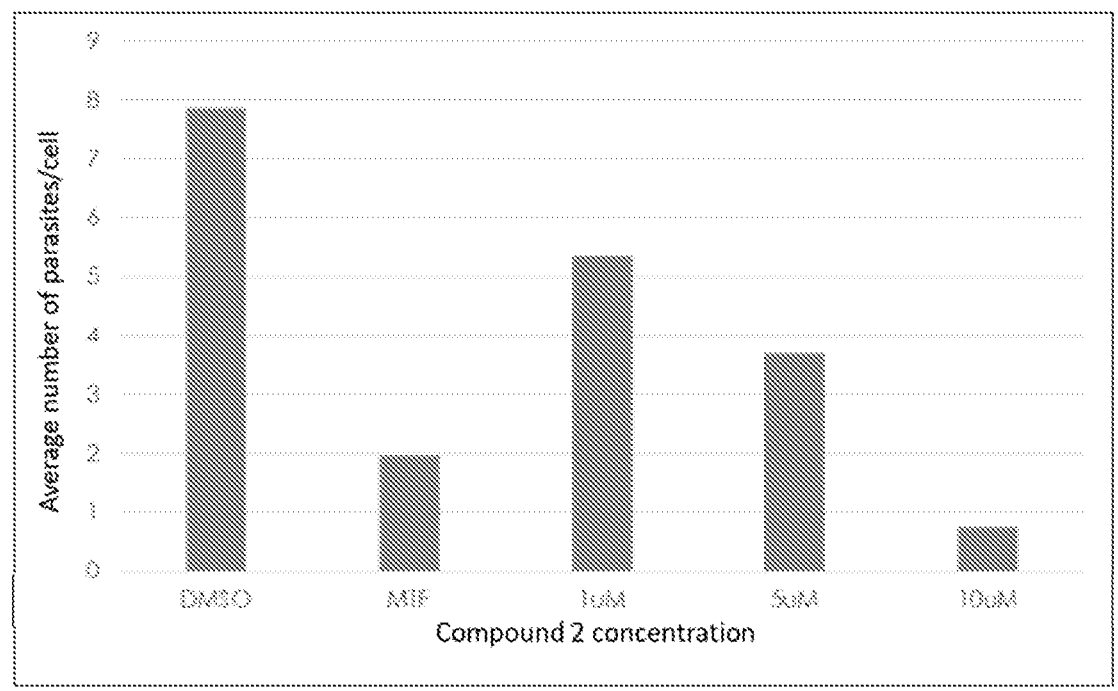
FIG. 42 shows that Compound 2 treatment decreased the total number of parasites per cell in a dose dependent manner.
Figure 43:
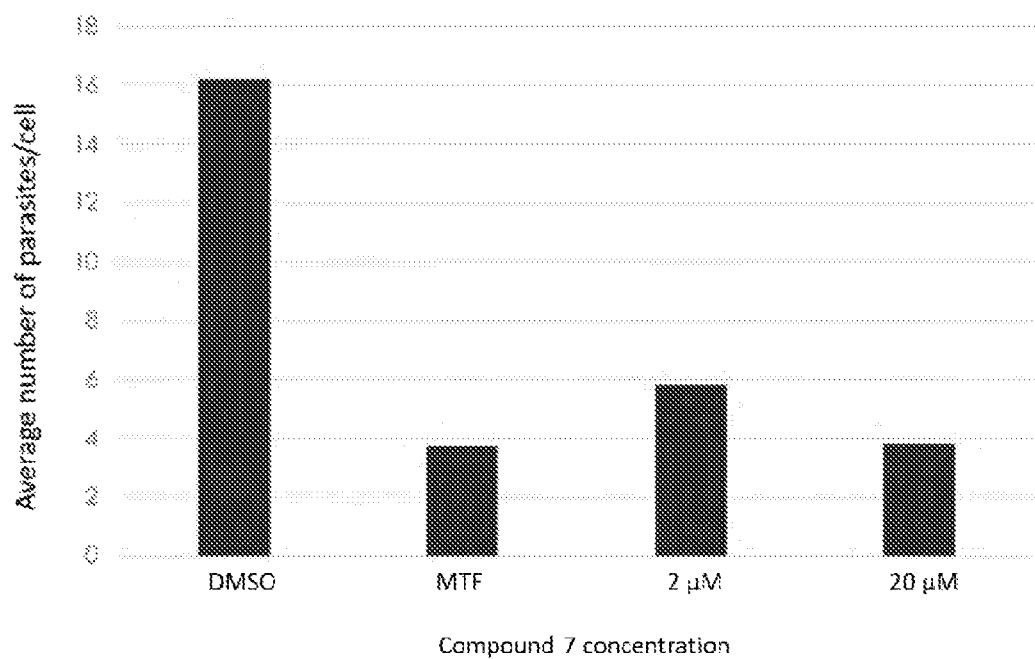
FIG. 43 shows that Compound 7 treatment decreased the number of parasites per cell.

FIG. 42 shows that Compound 2 treatment decreased the total number of parasites per cell in a dose dependent manner. FIG. 43 shows that Compound 7 treatment decreased the number of parasites per cell.

Embodiments

The following non-limiting embodiments provide illustrative examples of the invention, but do not limit the scope of the invention.

Embodiment 1. A method of treating an infection, the method comprising: administering to a subject in need thereof a therapeutically-effective amount of a compound of the formula:

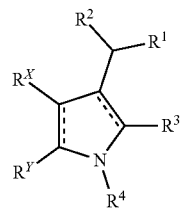

wherein:
each ≡≡≡ is independently a single bond or a double bond,
$R^1$ is cyano, an imine group, an acyl group, a carboxylic acid group, a carboxaldehyde group, an ester group, an amide group, a hydrazide group, a hydroxamic acid group, a hydroxamic acid ester group, a thioester group, or a thioacid group, any of which is substituted or unsubstituted;
each $R^2$ and $R^3$ is independently cyano, an imine group, an acyl group, alkyl, alkenyl, alkynyl, a carboxylic acid group, a carboxaldehyde group, an ester group, an amide group, a hydrazide group, a hydroxamic acid group, a hydroxamic acid ester group, a thioester group, a thioacid group, aryl, arylalkyl, heterocyclyl, cycloalkyl, cycloalkenyl, or heteroaryl, any of which is substituted or unsubstituted;
$R^4$ is an imine group, an acyl group, an acyloxy group, alkyl, alkenyl, alkynyl, an alkoxy group, an ether group, a carboxylic acid group, a carboxaldehyde group, an ester group, an amide group, a hydrazide group, a hydroxamic acid group, a hydroxamic acid ester group, a thioether group, a thioester group, a thioacid group, aryl, aryloxy, arylalkyl, arylalkoxy, heterocyclyl, cycloalkyl, cycloalkenyl, or heteroaryl, any of which is substituted or unsubstituted, or hydrogen; and $R^X$ and $R^Y$ together with the atoms to which $R^X$ and $R^Y$ are bound form a ring that is substituted or unsubstituted, or a pharmaceutically-acceptable salt thereof.

Embodiment 2. The method of embodiment 1, wherein $R^X$ and $R^Y$ together with the atoms to which $R^X$ and $R^Y$ are bound form a 6-membered or 7-membered ring that is substituted or unsubstituted.

Embodiment 3. The method of embodiment 1 or 2, wherein $R^X$ and $R^Y$ together with the atoms to which $R^X$ and $R^Y$ are bound form a 6-membered ring that is unsubstituted.

Embodiment 4. The method of embodiment 1 or 2, wherein $R^X$ and $R^Y$ together with the atoms to which $R^X$ and $R^Y$ are bound form a benzo ring, a [2,1]naphtho ring, a [3,2]naphtho ring, or a [4,3]naphtho ring, any of which is substituted or unsubstituted.

Embodiment 5. The method of any one of embodiments 1-4, wherein $R^1$ is cyano, an amide group, a hydrazide group, a hydroxamic acid group, or a hydroxamic acid ester group, any of which is substituted or unsubstituted.

Embodiment 6. The method of any one of embodiments 1-5, wherein each $R^2$ and $R^3$ is independently alkyl, aryl, arylalkyl, heterocyclyl, cycloalkyl, cycloalkenyl, or heteroaryl, any of which is substituted or unsubstituted.

Embodiment 7. The method of any one of embodiments 1-6, wherein $R^4$ is alkyl that is substituted or unsubstituted, or hydrogen.

Embodiment 8. The method of any one of embodiments 1-7, wherein the compound is of the formula:

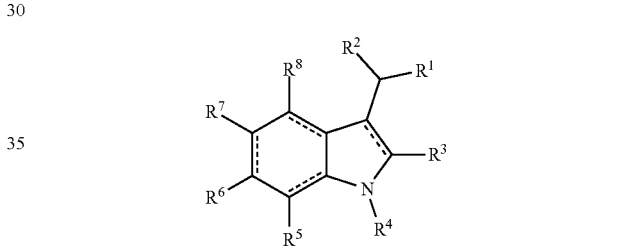

wherein:
each ≡≡≡ is independently a single bond or a double bond;
$R^4$ is an imine group, an acyl group, alkyl, alkenyl, alkynyl, aryl, arylalkyl, cycloalkyl, cycloalkenyl, heterocyclylalkyl, heterocyclylalkenyl, heteroaryl, or heteroarylalkyl, any of which is substituted or unsubstituted, or hydrogen;
each $R^5$, $R^6$, $R^7$, and $R^8$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, or heteroaryl, any of which is substituted or unsubstituted, or halogen or hydrogen; or each $R^5$ and $R^6$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, or heteroaryl, any of which is substituted or unsubstituted, or halogen or hydrogen, and $R^7$ and $R^8$ together with the atoms to which $R^7$ and $R^8$ are bound form a 6-membered ring that is substituted or unsubstituted; or each $R^5$ and $R^8$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, or heteroaryl, any of which is substituted or unsubstituted, or halogen or hydrogen, and $R^6$ and $R^7$ together with the atoms to which $R^6$ and $R^7$ are bound form a 6-membered ring that is substituted or unsubstituted; or each $R^7$ and $R^8$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, or heteroaryl, any of which is substituted or unsubstituted, or halogen or hydrogen, and $R^5$ and $R^6$ together with the atoms to which $R^5$ and $R^6$ are bound form a 6-membered ring that is substituted or unsubstituted.

Embodiment 9. The method of any one of embodiments 1-8, wherein $R^1$ is cyano, an amide group, a hydrazide group, a hydroxamic acid group, or a hydroxamic acid ester group, any of which is substituted or unsubstituted.

Embodiment 10. The method of any one of embodiments 1-9, wherein each $R^2$ and $R^3$ is independently alkyl, aryl, arylalkyl, cycloalkyl, cycloalkenyl, or heteroaryl, any of which is substituted or unsubstituted.

Embodiment 11. The method of any one of embodiments 1-10, wherein $R^4$ is substituted or unsubstituted alkyl, or hydrogen.

Embodiment 12. The method of any one of embodiments 1-11, wherein $R^4$ is methyl, ethyl, n-propyl, or n-butyl.

Embodiment 13. The method of any one of embodiments 8-12, wherein each $R^5$, $R^6$, $R^7$, and $R^g$ is independently hydroxyl, sulfhydryl, nitro, cyano, alkyl, alkenyl, alkynyl, an alkoxy group, an ether group, or an amine group, any of which is substituted or unsubstituted, or halogen or hydrogen.

Embodiment 14. The method of any one of embodiments 8-12, wherein $R^5$ and $R^6$ together with the atoms to which $R^5$ and $R^6$ are bound form a 6-membered ring that is unsubstituted, and wherein each $R^7$ and $R^8$ is hydrogen.

Embodiment 15. The method of any one of embodiments 1-14, wherein the compound is of the formula:

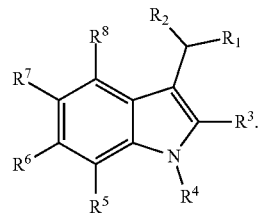

Embodiment 16. The method of any one of embodiments 1-15, wherein $R^1$ is —CN, —C(=O)N($R^{w1}$)O$R^{w2}$, or —C(=O)N($R^{w1}$)$R^{w2}$, wherein each $R^{w1}$ and $R^{w2}$ is independently alkyl, alkenyl, alkynyl, aryl, arylalkyl, cycloalkyl, cycloalkenyl, heterocyclyl, or heteroaryl, any of which is substituted or unsubstituted, or hydrogen.

Embodiment 17. The method of embodiment 16, wherein each $R^{w1}$ and $R^{w2}$ is independently hydrogen or alkyl.

Embodiment 18. The method of any one of embodiments 1-17, wherein $R^1$ is —CN, —C(=O)NHOH, —C(=O)NHOMe, or —C(=O)NH$_2$.

Embodiment 19. The method of any one of embodiments 1-18, wherein $R^2$ is alkyl, alkenyl, alkynyl, aryl, arylalkyl, cycloalkyl, cycloalkenyl, heterocyclyl, or heteroaryl, any of which is substituted or unsubstituted.

Embodiment 20. The method of any one of embodiments 1-19, wherein $R^2$ is substituted or unsubstituted aryl.

Embodiment 21. The method of any one of embodiments 1-20, wherein $R^2$ is substituted or unsubstituted phenyl.

Embodiment 22. The method of any one of embodiments 1-21, wherein $R^2$ is phenyl substituted with an alkoxy group, halogen, an alkylamino group, or an alkyl group.

Embodiment 23. The method of any one of embodiments 1-21, wherein $R^2$ is unsubstituted phenyl.

Embodiment 24. The method of any one of embodiments 1-5, 7-9, or 11-23, wherein $R^3$ is alkyl, alkenyl, alkynyl, aryl, arylalkyl, cycloalkyl, cycloalkenyl, heterocyclyl, or heteroaryl, any of which is substituted or unsubstituted.

Embodiment 25. The method of any one of embodiments 1-24, wherein $R^3$ is alkyl or aryl, each of which is unsubstituted or substituted.

Embodiment 26. The method of any one of embodiments 1-25, wherein $R^3$ is methyl, phenyl, naphthalen-1-yl or naphthalen-2-yl.

Embodiment 27. The method of any one of embodiments 1-11 or 13-26, wherein $R^4$ is hydrogen, or substituted or unsubstituted alkyl.

Embodiment 28. The method of any one of embodiments 1-11 or 13-27, wherein $R^4$ is hydrogen, methyl, ethyl, n-propyl, or n-butyl.

Embodiment 29. The method of any one of embodiments 8-28, wherein each $R^5$, $R^6$, $R^7$, and $R^g$ is independently hydroxyl, sulfhydryl, nitro, cyano, alkyl, alkenyl, alkynyl, an alkoxy group, an ether group, or an amine group, any of which is substituted or unsubstituted, or halogen or hydrogen.

Embodiment 30. The method of any one of embodiments 8-12 or 14-28, wherein each $R^7$ and $R^8$ is hydrogen, and $R^5$ and $R^6$ together with the atoms to which $R^5$ and $R^6$ are bound form a 6-membered ring that is unsubstituted.

Embodiment 31. The method of any one of embodiments 8-13 or 15-29, wherein each $R^5$, $R^6$, $R^7$, and $R^g$ is hydrogen.

Embodiment 32. The method of any one of embodiments 8-12 or 15-28, wherein each $R^7$ and $R^8$ is hydrogen, and $R^5$ and $R^6$ together with the atoms to which $R^5$ and $R^6$ are bound form a 6-membered ring that is substituted.

Embodiment 33. The method of any one of embodiments 1-13, 15-21, 23-29, or 31, wherein the compound is of the formula:

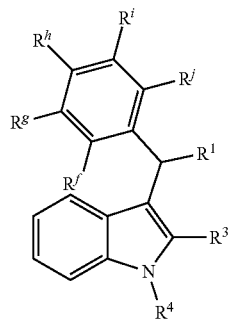

wherein:
R$^f$ is hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclyl, heteroaryl, any of which is substituted or unsubstituted, or halogen or hydrogen;

each R$^g$ and R$^h$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclyl, or heteroaryl, any of which is substituted or unsubstituted, or halogen or hydrogen, or R$^g$ and R$^h$ together with the atoms to which R$^g$ and R$^h$ are bound optionally form a 6-membered ring that is substituted or unsubstituted; and each R$^i$ and R$^j$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclyl, or heteroaryl, any of which is substituted or unsubstituted, or halogen or hydrogen, or R$^i$ and R$^j$ together with the atoms to which R$^i$ and R$^j$ are bound optionally form a 6-membered ring that is substituted or unsubstituted.

Embodiment 34. The method of any one of embodiments 1-13, 15-21, 23-29, 31, or 33, wherein R$^3$ is alkyl, cycloalkyl, heterocyclyl, aryl, or heteroaryl, each of which is substituted or unsubstituted.

Embodiment 35. The method of any one of embodiments 1-13, 15-21, 23-29, 31, 33, or 34 wherein R$^3$ is alkyl or aryl, each of which is substituted or unsubstituted.

Embodiment 36. The method of any one of embodiments 1-13, 15-21, 23-29, 31, or 33-35, wherein R$^3$ is methyl, phenyl, naphthalen-1-yl or naphthalen-2-yl.

Embodiment 37. The method of any one of embodiments 1-11, 13, 15-21, 23-29, 31, or 33-36, wherein R$^4$ is hydrogen, or substituted or unsubstituted alkyl.

Embodiment 38. The method of any one of embodiments 1-11, 13, 15-21, 23-29, 31, or 33-37, wherein R$^4$ is hydrogen, methyl, ethyl, n-propyl, or n-butyl.

Embodiment 39. The method of any one of embodiments 1-11, 13, 15-21, 23-29, 31, or 33-38, wherein each R$^f$, R$^g$, R$^h$, R$^i$, and R$^j$ is independently hydroxyl, sulfhydryl, nitro, cyano, alkyl, alkenyl, alkynyl, an alkoxy group, an alkylamino group, an ether group, or an amine group, any of which is substituted or unsubstituted, or halogen or hydrogen.

Embodiment 40. The method of any one of embodiments 1-11, 13, 15-21, 23-29, 31, or 33-39, wherein each R$^f$, R$^g$, R$^h$, R$^i$, and R$^j$ is hydrogen.

Embodiment 41. The method of any one of embodiments 1-29, 31, or 33-40, wherein the compound is of the formula:

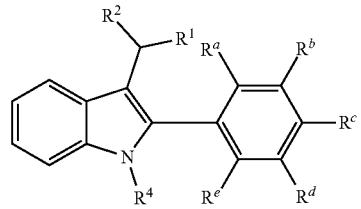

wherein:
R$^a$ is hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclyl, or heteroaryl, any of which is substituted or unsubstituted, or halogen or hydrogen;

each R$^b$ and R$^c$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclyl, or heteroaryl, any of which is substituted or unsubstituted, or halogen or hydrogen, or R$^b$ and R$^c$ together with the atoms to which R$^b$ and R$^c$ are bound optionally form a 6-membered ring that is substituted or unsubstituted; and each R$^d$ and R$^e$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclyl, or heteroaryl, any of which is substituted or unsubstituted, or halogen or hydrogen, or $R^d$ and $R^e$ together with the atoms to which $R^d$ and $R^e$ are bound optionally form a 6-membered ring that is substituted or unsubstituted.

Embodiment 42. The method of any one of embodiments 1-29, 31, or 33-41, wherein $R^1$ is —CN, —C(=O)N($R^{w1}$)O$R^{w2}$, or —C(=O)N($R^{w1}$)$R^{w2}$, wherein each $R^{w1}$ and $R^{w2}$ is independently alkyl, alkenyl, alkynyl, aryl, arylalkyl, cycloalkyl, cycloalkenyl, heterocyclyl, or heteroaryl, any of which is substituted or unsubstituted, or hydrogen.

Embodiment 43. The method of any one of embodiments 1-29, 31, or 33-42, wherein $R^2$ is alkyl, alkenyl, alkynyl, aryl, arylalkyl, cycloalkyl, cycloalkenyl, heterocyclyl, or heteroaryl.

Embodiment 44. The method of any one of embodiments 1-29, 31, or 33-43, wherein each $R^a$, $R^b$, $R^c$, $R^d$, and $R^e$ is independently hydroxyl, sulfhydryl, nitro, cyano, alkyl, alkenyl, alkynyl, an alkoxy group, an alkylamino group, an ether group, or an amine group, any of which is substituted or unsubstituted, or halogen or hydrogen.

Embodiment 45. The method of any one of embodiments 1-29, 31, or 33-44, wherein each $R^a$, $R^b$, $R^c$, $R^d$, and $R^e$ is hydrogen.

Embodiment 46. The method of any one of embodiments 1-29, 31, or 33-43, wherein $R^d$ and $R^e$ together with the atoms to which $R^d$ and $R^e$ are bound form a 6-membered ring that is unsubstituted.

Embodiment 47. The method of any one of embodiments 1-29, 31, or 33-40, wherein $R^b$ and $R^c$ together with the atoms to which $R^b$ and $R^c$ are bound form a 6-membered ring that is unsubstituted.

Embodiment 48. The method of any one of embodiments 1-29, 31, or 33-47, wherein $R^4$ is hydrogen, or substituted or unsubstituted alkyl.

Embodiment 49. The method of any one of embodiments 1-29, 31, or 33-48, wherein $R^4$ is hydrogen, methyl, ethyl, n-propyl, or n-butyl.

Embodiment 50. The method of any one of embodiments 1-13, 15-29, 31, or 33-49, wherein the compound is of the formula:

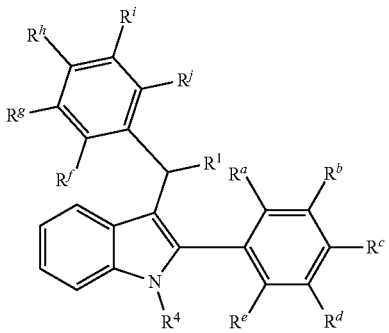

wherein:
$R^f$ is hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclyl, or heteroaryl, any of which is substituted or unsubstituted, or halogen or hydrogen;

each $R^g$ and $R^h$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclyl, or heteroaryl, any of which is substituted or unsubstituted, or halogen or hydrogen, or $R^g$ and $R^h$ together with the atoms to which $R^g$ and $R^h$ are bound optionally form a 6-membered ring that is substituted or unsubstituted; and each $R^i$ and $R^j$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an alkylamino group an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclyl, or heteroaryl, any of which is substituted or unsubstituted, or halogen or hydrogen, or $R^i$ and $R^j$ together with the atoms to which $R^i$ and $R^j$ are bound optionally form a 6-membered ring that is substituted or unsubstituted.

Embodiment 51. The method of embodiment 50, wherein each $R^a$, $R^b$, $R^c$, $R^d$, $R^e$ $R^f$, $R^g$, $R^h$, $R^i$, and $R^j$ is independently hydroxyl, sulfhydryl, nitro, cyano, alkyl, alkenyl, alkynyl, an alkoxy group, an alkylamino group, an ether group, or an amine group, any of which is substituted or unsubstituted, or hydrogen.

Embodiment 52. The method of embodiment 50 or 51, wherein each $R^a$ $R^d$, $R^e$ $R^f$, $R^g$, $R^h$, $R^i$, and $R^j$ is independently hydroxyl, sulfhydryl, nitro, cyano, alkyl, alkenyl, alkynyl, an alkoxy group, an ether group, or an amine group, any of which is substituted or unsubstituted, or halogen or hydrogen, and $R^b$ and $R^c$ together with the atoms to which $R^b$ and $R^c$ are bound form a 6-membered ring that is substituted or unsubstituted.

Embodiment 53. The method of any one of embodiments 50-52, wherein $R^b$ and $R^c$ together with the atoms to which $R^b$ and $R^c$ are bound form a 6-membered ring that is unsubstituted.

Embodiment 54. The method of embodiment 50 or 51, wherein each $R^a$, $R^b$, $R^c$, $R^f$, $R^g$, $R^h$, $R^i$, and $R^j$ is independently hydroxyl, sulfhydryl, nitro, cyano, alkyl, alkenyl, alkynyl, an alkoxy group, an ether group, or an amine group, any of which is substituted or unsubstituted, or halogen or hydrogen; and $R^d$ and $R^e$ together with the atoms to which $R^d$ and $R^e$ are bound form a 6-membered ring that is substituted or unsubstituted.

Embodiment 55. The method of embodiment 50 or 54, wherein $R^d$ and $R^e$ together with the atoms to which $R^d$ and $R^e$ are bound form a 6-membered ring that is unsubstituted.

Embodiment 56. The method of any one of embodiments 50-55, wherein $R^4$ is hydrogen or substituted or unsubstituted alkyl.

Embodiment 57. The method of any one of embodiments 50-56, wherein $R^4$ is hydrogen, methyl, ethyl, n-propyl, or n-butyl.

Embodiment 58. The method of any one of embodiments 1, 8, 15, or 33, wherein the compound is of the formula:

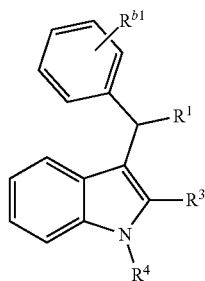

wherein:

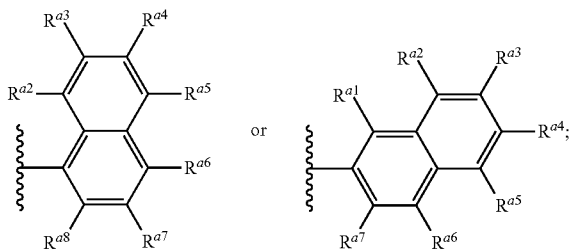

$R^3$ is methyl, phenyl,
wherein each $R^{b1}$, $R^{a1}$, $R^{a2}$, $R^{a3}$, $R^{a4}$, $R^{a5}$, $R^{a6}$, $R^{a7}$ and $R^{a8}$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclyl, or heteroaryl, any of which is substituted or unsubstituted, or halogen or hydrogen.

Embodiment 59. The method of embodiment 58, wherein each $R^{b1}$, $R^{a1}$, $R^{a2}$, $R^{a3}$, $R^{a4}$, $R^{a5}$, $R^{a6}$, $R^{a7}$ and $R^{a8}$ is independently hydroxyl, sulfhydryl, nitro, cyano, alkyl, alkenyl, alkynyl, an alkoxy group, an alkylamino group, an ether group, or an amine group, any of which is substituted or unsubstituted, or halogen or hydrogen.

Embodiment 60. The method of embodiment 58 or 59, wherein each $R^{a1}$, $R^{a2}$, $R^{a3}$, $R^{a4}$, $R^{a5}$, $R^{a6}$, $R^{a7}$ and $R^{a8}$ is hydrogen.

Embodiment 61. The method of any one of embodiments 58-60, wherein $R^{b1}$ is hydrogen.

Embodiment 62. The method of any one of embodiments 58-61, wherein $R^4$ is hydrogen or substituted or unsubstituted alkyl.

Embodiment 63. The method of any one of embodiments 58-62, wherein $R^4$ is hydrogen, methyl, ethyl, n-propyl, or n-butyl.

Embodiment 64. The method of any one of embodiments 1, 8, 15, or 33, wherein the compound is of the formula:

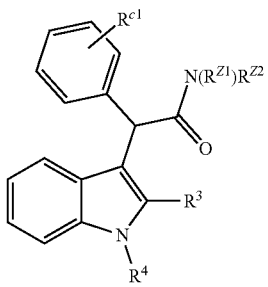

wherein:
each $R^{Z1}$ and $R^{Z2}$ is independently hydroxyl, an acyl group, an acyloxy group, alkyl, alkenyl, alkynyl, an alkoxy group, an ether group, a carboxylic acid group, a carboxaldehyde group, an ester group, an amine group, an amide group, aryl, aryloxy, arylalkyl, arylalkoxy, heterocyclyl, cycloalkyl, cycloalkenyl, heterocyclyl, or heteroaryl, any of which is substituted or unsubstituted, or hydrogen;
$R^{c1}$ is independently hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, cycloalkyl, cycloalkenyl, heterocyclyl, or heteroaryl, any of which is substituted or unsubstituted, or halogen or hydrogen.

Embodiment 65. The method of embodiment 64, wherein each $R^{Z1}$ and $R^{Z2}$ is independently hydroxyl, alkyl, alkenyl, alkynyl, an alkoxy group, an ether group, an amine group, aryl, aryloxy, arylalkyl, arylalkoxy, heterocyclyl, cycloalkyl, cycloalkenyl, heterocyclyl, or heteroaryl, any of which is substituted or unsubstituted, or hydrogen.

Embodiment 66. The method of embodiment 64 or 65, wherein each $R^{Z1}$ and $R^{Z2}$ is independently hydrogen, hydroxyl, alkyl, or an alkoxy group.

Embodiment 67. The method of any one of embodiments 64-66, wherein $R^{Z1}$ is hydrogen, and $R^{Z2}$ is hydrogen, hydroxyl, alkyl, or an alkoxy group.

Embodiment 68. The method of any one of embodiments 64-67, wherein $R^{c1}$ is hydroxyl, sulfhydryl, nitro, cyano, alkyl, alkenyl, alkynyl, an alkoxy group, an alkylamino group, an ether group, or an amine group, any of which is substituted or unsubstituted, or halogen or hydrogen.

Embodiment 69. The method of any one of embodiments 64-68, wherein $R^{c1}$ is hydrogen.

Embodiment 70. The method of any one of embodiments 64-69, wherein $R^3$ is alkyl, alkenyl, alkynyl, aryl, arylalkyl, cycloalkyl, cycloalkenyl, heterocyclyl, or heteroaryl, any of which is substituted or unsubstituted.

Embodiment 71. The method of any one of embodiments 64-70, wherein $R^3$ is alkyl, or substituted or unsubstituted aryl.

Embodiment 72. The method of any one of embodiments 64-71, wherein $R^3$ is methyl, phenyl, naphthalen-1-yl, or naphthalen-2-yl.

Embodiment 73. The method of any one of embodiments 64-72, wherein $R^4$ is alkyl that is substituted or unsubstituted or hydrogen.

Embodiment 74. The method of any one of embodiments 64-73, wherein $R^4$ is hydrogen, methyl, ethyl, n-propyl, or n-butyl.

Embodiment 75. The method of any one of embodiments 1, 8, 15, 33, 41, 50, 58, or 64, wherein the compound that is administered is of the formula:

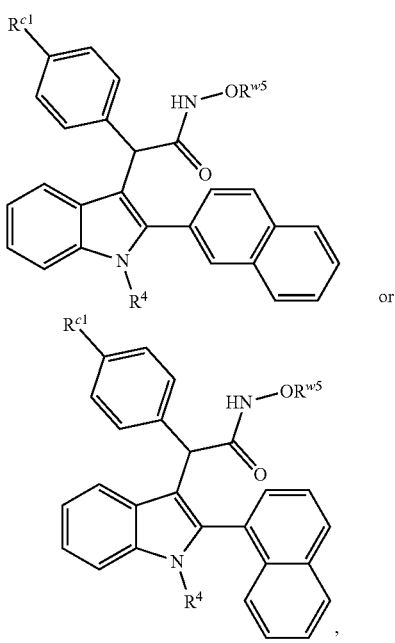

wherein:
$R^{w5}$ is hydrogen or alkyl;
$R^{c1}$ is hydrogen, alkyl, alkylamino, or alkoxy; and
$R^4$ is hydrogen or alkyl.

Embodiment 76. The method of embodiment 75, wherein $R^{w5}$ is hydrogen.

Embodiment 77. The method of embodiment 75 or 76, wherein $R^{c1}$ is hydrogen, isopropyl, —$NMe_2$, or —OMe.

Embodiment 78. The method of any one of embodiments 75-77, wherein $R^4$ is hydrogen.

Embodiment 79. The method of any one of embodiments 75-78, wherein $R^{w5}$, $R^{c1}$, and $R^4$ are hydrogen.

Embodiment 80. The method of any one of embodiments 75-77, wherein $R^{w5}$ and $R^{c1}$ are hydrogen, and $R^4$ is methyl.

Embodiment 81. The method of any one of embodiments 1, 18, 15, or 33, wherein the compound is:
N-hydroxy-2-phenyl-2-(2-phenyl-1H-indol-3-yl)acetamide;
N-hydroxy-2-(2-methyl-1H-indol-3-yl)-2-phenylacetamide;
N-hydroxy-2-(4-isopropylphenyl)-2-(2-(naphthalen-2-yl)-1H-indol-3-yl)acetamide;
N-hydroxy-2-(1-methyl-2-(naphthalen-2-yl)-1H-indol-3-yl)-2-phenylacetamide;
2-(2-(naphthalen-2-yl)-1H-indol-3-yl)-2-phenylacetonitrile;
2-(4-(dimethylamino)phenyl)-N-hydroxy-2-(2-(naphthalen-2-yl)-1H-indol-3-yl)acetamide;
N-hydroxy-2-(2-(naphthalen-2-yl)-1H-indol-3-yl)-2-phenylacetamide;
N-hydroxy-2-(2-(naphthalen-1-yl)-1H-benzo[g]indol-3-yl)-2-phenylacetamide;
N-hydroxy-2-(4-methoxyphenyl)-2-(2-(naphthalen-2-yl)-1H-indol-3-yl)acetamide;
2-(2-(naphthalen-2-yl)-1H-indol-3-yl)-2-phenylacetamide; or
2-(1-butyl-2-(naphthalen-2-yl)-1H-indol-3-yl)-N-hydroxy-2-phenylacetamide.

Embodiment 82. The method of any one of embodiments 1, 8, 15, 33, 41, 50, 58, 64, or 75, wherein the compound is of the

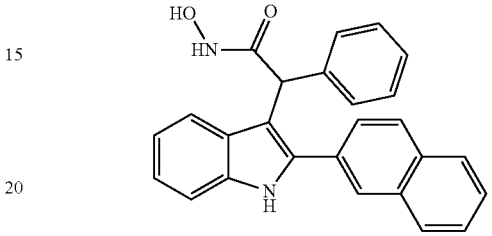

Embodiment 83. The method of any one of embodiments 1, 8, 15, 33, 41, 50, 58, 64, or 75, wherein the compound is of the formula:

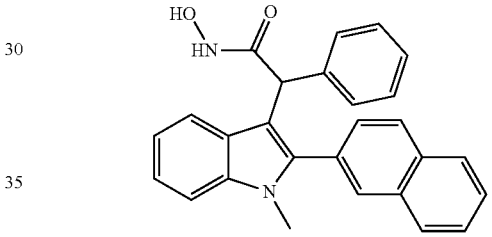

Embodiment 84. The method of any one of embodiment 1-83, wherein the infection is a parasitic infection.

Embodiment 85. The method of any one of embodiments 1-84, wherein the infection is a protozoan infection.

Embodiment 86. The method of any one of embodiments 1-85, wherein the infection is caused by *Toxoplasma gondii*.

Embodiment 87. The method of any one of embodiments 1-85, wherein the infection is caused by *Plasmodium falciparum*.

Embodiment 88. The method of any one of embodiments 1-85, wherein the infection is caused by *Leishmania major*.

Embodiment 89. The method of any one of embodiments 1-85, wherein the infection is caused by *Trypanosoma cruzi*.

Embodiment 90. The method of any one of embodiments 1-89, wherein the subject is a human subject.

Embodiment 91. The method of any one of embodiments 1-89, wherein the subject is an animal subject.

Embodiment 92. The method of any one of embodiments 1-91, wherein the administering is oral.

Embodiment 93. The method of any one of embodiments 1-91, wherein the administering is topical.

Embodiment 94. The method of any one of embodiments 1-93, wherein the therapeutically-effective amount is from about 0.01 mg/kg to about 100 mg/kg.

What is claimed is:
1. A method of treating a protozoan infection, the method comprising: administering to a subject in need thereof a therapeutically-effective amount of a compound of the formula:

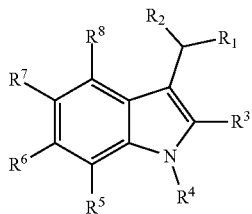

wherein:
R¹ is —CN, —C(=O)NHOH, or —C(=O)NH₂;
R² is substituted or unsubstituted phenyl;
R³ is methyl, phenyl, naphthalen-1-yl, or naphthalen-2-yl;
R⁴ is methyl, ethyl, n-propyl, n-butyl, or hydrogen; and
each R⁵, R⁶, R⁷, and R⁸ is hydrogen,
or a pharmaceutically-acceptable salt thereof.

2. The method of claim 1, wherein R⁴ is hydrogen or methyl.

3. The method of claim 1, wherein the compound is of the formula:

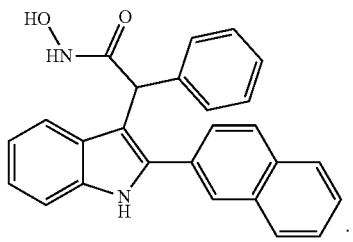 [SMILES: O=C(NO)C(c1ccccc1)c1c(-c2ccc3ccccc3c2)[nH]c2ccccc12]

4. The method of claim 1, wherein the compound is of the formula:

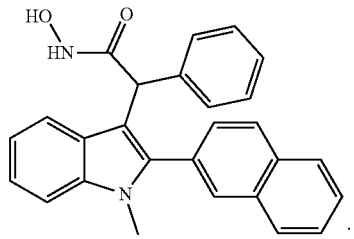 [SMILES: Cn1c(-c2ccc3ccccc3c2)c(C(C(=O)NO)c2ccccc2)c2ccccc21]

5. The method of claim 1, wherein the protozoan infection is caused by *Toxoplasma gondii*.

6. The method of claim 1, wherein the protozoan infection is caused by *Plasmodium falciparum*.

7. The method of claim 1, wherein the protozoan infection is caused by *Leishmania major*.

8. The method of claim 1, wherein the protozoan infection is caused by *Trypanosoma cruzi*.

9. The method of claim 1, wherein the subject is a human subject.

10. The method of claim 1, wherein the administering is topical.

11. The method of claim 1, wherein the therapeutically-effective amount is from about 0.01 mg/kg to about 100 mg/kg.

* * * * *